(12) United States Patent
Deaton et al.

(10) Patent No.: US 11,160,838 B2
(45) Date of Patent: Nov. 2, 2021

(54) **ANTIFUNGAL AND ANTIMICROBIAL USES OF *BACILLUS SUBTILIS* CONTAINING COMPOSITIONS**

(71) Applicant: Deerland Enzymes, Inc., Kennesaw, GA (US)

(72) Inventors: John Deaton, Kennesaw, GA (US); Ana Maria Cuentas, Woodstock, GA (US)

(73) Assignee: Deerland Enzymes, Inc., Kennesaw, GA (US)

( * ) Notice: Subject to any disclaimer, the term of this patent is extended or adjusted under 35 U.S.C. 154(b) by 0 days.

(21) Appl. No.: 16/989,186

(22) Filed: Aug. 10, 2020

(65) Prior Publication Data
US 2021/0145899 A1    May 20, 2021

Related U.S. Application Data

(60) Provisional application No. 62/884,903, filed on Aug. 9, 2019.

(51) Int. Cl.
| | | |
|---|---|---|
| *A61K 35/742* | (2015.01) | |
| *A61K 9/00* | (2006.01) | |
| *A61P 31/10* | (2006.01) | |
| *A61K 38/12* | (2006.01) | |
| *A61K 38/05* | (2006.01) | |
| *A61K 38/16* | (2006.01) | |
| *A61K 31/365* | (2006.01) | |
| *A61P 31/04* | (2006.01) | |
| *A61K 31/357* | (2006.01) | |
| *A61K 35/00* | (2006.01) | |

(52) U.S. Cl.
CPC .......... *A61K 35/742* (2013.01); *A61K 9/0014* (2013.01); *A61K 31/357* (2013.01); *A61K 31/365* (2013.01); *A61K 38/05* (2013.01); *A61K 38/12* (2013.01); *A61K 38/164* (2013.01); *A61P 31/04* (2018.01); *A61P 31/10* (2018.01); *A61K 2035/11* (2013.01)

(58) Field of Classification Search
None
See application file for complete search history.

(56) References Cited

U.S. PATENT DOCUMENTS

| 9,247,757 B2 | 2/2016 | Schmidt et al. |
| 9,457,054 B2 | 10/2016 | Schmidt et al. |
| 2016/0100607 A1 | 4/2016 | Schmidt et al. |

OTHER PUBLICATIONS

Brito, P.H., et al., "Genetic competence drives genome diversity in Bacillus subtilis," Genome Biology & Evolution 10: 108-124 (2018).

Chantawannakul, P., et al., "Characterization of protease of Bacillus subtilis strain 38 isolated from traditionally fermented soybean in Northern Thailand," Sci. Asia 28: 241-245 (2002).

Cheng, F., et al., "Characterization of a blend-biosurfactant of glycolipid and lipopeptide produced by Bacillus subtilis TU2 isolated from underground oil-extraction wastewater," J. Microbiology & Biotechnology 23(3): 390-396 (2013).

Chung, S., et al., Isolation and partial characterization of Bacillus subtilis ME488 for suppression of soilborne pathogens of cucumber and pepper, Applied Microbiology & Biotechnology 80:115-123 (2008).

Cusack, S., et al., "How Beneficial is the Use of Probiotic Supplements for the Aging Gut?," Aging Health 7:179 (2011) (Abstract Only).

Dunlap, C.A., et al., "Genomic analysis and secondary metabolite production in Bacillus amyloliquefaciens AS 43.3: a biocontrol antagonist of Fusarium Head Blight," Biological Control 64: 166 (2013) (Abstract Only).

Dunlap, C.A., et al., "Genomic analysis of Bacillus subtilis OH 131.1 and co-culturing with Cryptococcus flavescens for control of fusarium head blight," Plant Gene 2: 1-9 (2015).

Falardeau, J., et al., Ecological and mechanistic insights into the direct and indirect antimicrobial properties of Bacillus subtilis lipopeptides on plant pathogens, J. Chemical Ecology 39: 869-78 (2013).

Fan, H., et al., "Fengycin produced by Bacillus subtilis 9407 plays a major role in the biocontrol of apple ring rot disease," Microbiological Research 199: 89-97 (2017).

Hawlena, H., et al., "Bacteriocin-mediated interactions within and between coexisting species," Ecology & Evolution 2: 2516-2521 (2012).

Hong, H., et al., "The use of bacterial spore formers as probiotics," FEMS Microbiology Revs. 29: 813-835 (2005).

Inatsu, Y., et al., "Characterization of Bacillus subtilis strains isolated from fermented soybean foods in southeast Asia: comparison with B. subtilis (natto) starter strains," Japan Agricultural Res. Quarterly 36: 169-175 (2002).

Inatsu, Y., et al., "Characterization of Bacillus subtilis strains in Thua nao, a traditional fermented soybean food in northern Thailand," Letters in Applied Microbiology 43: 237-242 (2006).

Ji, S., et al., "Improved production of sublancin via introduction of three characteristic promoters into operon clusters responsible for this novel distinct glycopeptide biosynthesis," Microbial Cell Factories 14: 17 (2015).

Kobayashi, K., et al., "Plant methyl salicylate induces defense responses in the rhizobacterium Bacillus subtilis," Environmental Microbiology 17: 1365-1376 (2015) (Abstract Only).

(Continued)

*Primary Examiner* — Padmavathi Baskar
(74) *Attorney, Agent, or Firm* — Amin Talati Wasserman LLP; George M. Carrera, Jr.; Jonathan J. Krit

(57) ABSTRACT

Methods of treating, removing, or preventing the accumulation of bacteria, fungus, and/or yeast on a surface, and/or treating or preventing fungal, bacterial, and/or yeast infections in a mammal, with compositions containing *Bacillus subtilis* or material secreted from *Bacillus subtilis* are provided. Compositions including *Bacillus subitlis* or material secreted from *Bacillus subtilis* that can be used in methods of treating, removing, or preventing the accumulation, growth, or activity of bacteria, fungus, and/or yeast on a surface, and/or treating or preventing fungal, bacterial, and/or yeast infections in a mammal, are provided.

2 Claims, 16 Drawing Sheets

(56) References Cited

OTHER PUBLICATIONS

Lee, H., et al., "Purification and structural characterization of bacillomycin F produced by a bacterial honey isolate active against Byssochlamys fulva H25," J. Applied Microbiology 105: 663-673 (2008).

Leejeerajumnean, A., et al., "Volatile compounds in Bacillus-fermented soybeans," J. Sci Food & Agriculture 81: 525-529 (2001) (Abstract Only).

Lefevre, M., et al., "Probiotic strain Bacillus subtilis CU1 stimulates immune system of elderly during common infectious disease period: a randomized, double-blind placebo-controlled study," Immunity & Ageing 12: 24 (2015).

Moryl, M., et al., "Antimicrobial, antiadhesive and antibiofilm potential of lipopeptides synthesized by Bacillus subtilis, on uropathogenic bacteria," ACTA Biochimica Polonica 62: 725-732 (2015).

Nakamura, L.K., et al., "Relationship of Bacillus subtilis clades associated with strains 168 and W23: a proposal for *Bacillus subtilis* subsp. subtilis subsp. nov. and *Bacillus subtilis* subsp. spizizenii subsp. nov.," Int'l J. Systematic Bacteriology 49: 1211-1215 (1999).

Norris, G.E., et al., "The glycocins: in a class of their own," Current Opinion in Structural Biology 40: 112-119 (2016) (Abstract Only).

Özcengiz, G., et al., "Biochemistry, genetics and regulation of bacilysin biosynthesis and its significance more than an antibiotic," New Biotechnol. 32: 612-619 (2015) (Abstract Only).

Peypoux, F., et al., "Structure of bacillomycin F, a new peptidolipid antibiotic of the iturin group," Eur. J. Biochemistry 153: 335-340 (1985).

Qin, J., et al., "A human gut microbial gene catalogue established by metagenomics sequencing," Nature 464: 59 (2010).

Riley, M.A., et al., "Bacteriocin diversity: ecological and evolutionary perspectives," Biochimie 84: 357-364 (2002).

Rooney, A.P., et al., "Phylogeny and molecular taxonomy of the *Bacillus subtilis* species complex and description of *Bacillus subtilis* subsp. inaquosorum subsp. nov.," Int'l J. Systematic & Evolutionary Microbiology 59: 2429-2436 (2009).

Ruiz-Sanchez, E., et al., "Antifungal activity and molecular identification of native strains of Bacillus subtilis," Agrociencia 50: 133-148 (2016).

Selvam, R., et al., "Effect of Bacillus subtilis PB6, a natural probiotic on colon mucosal inflammation and plasma cytokines levels in inflammatory bowel disease," Indian J. Biochemistry & Biophysics 46: 79-85 (2009).

Sumi, H., et al., "Natto Bacillus as an oral fibrinolytic agent: nattokinase activity and the ingestion effect of Bacillus subtilis natto," Food Sci. & Tech. Res. 10:17-20 (2004).

Urano, T., et al., "The profibrolytic enzyme subtilisin NAT purified from Bacillus subtilis cleaves and inactivates plasminogen activator inhibitor type 1," J. Biological Chemistry 276: 24690-24696 (2001).

Vanittanakom, N., et al., "Fengycin-a novel antifungal lipopeptide antibiotic produced by Bacillus subtilis F-29-3," J. Antibiot. 39: 888-901 (1986).

Volpon, L., et al., "NMR structure of antibiotics plipastatins A and B from Bacillus subtilis inhibitors of phospholipase A2," FEBS Letters 485: 76-80 (2000).

Nu, L., et al., "Difficidin and bacilysin from Bacillus amyloliquefaciens FZB42 have antibacterial activity against Xanthomonasoryzae rice pathogens," Scientific Reports 5:12975 (2015).

Yi, H., et al., "Genomic insights into the taxonomic status of the three subspecies of *Bacillus subtilis*," Syst. Appl. Microbiol. 37: 95-99 (2014) (Abstract Only).

Zhu, X., et al., "Study on effect of antimicrobial lipopeptide from Bacillus subtilis against *E. coli*," J. Pure Appl. Microbiol. 7: 485-490 (2013) (Abstract Only).

ANTIFUNGAL AND ANTIMICROBIAL USES OF *BACILLUS SUBTILIS* CONTAINING COMPOSITIONS

This application claims the benefit of U.S. Provisional Application No. 62/884,903, filed on Aug. 9, 2019, which is hereby incorporated by reference in its entirety.

TECHNICAL FIELD OF THE INVENTION

The present disclosure relates to methods of treating, removing, or preventing the accumulation, growth, and/or activity of bacteria, fungus, and/or yeast on a surface, and/or treating or preventing fungal, bacterial, and/or yeast infections in a mammal, with *Bacillus subtilis*-containing composition(s). The *Bacillus subtilis*-containing composition(s) of the present disclosure can be used as probiotic supplementation.

BACKGROUND

The microbiome is the genetic material of all microbes (bacteria, fungi, protozoa, and viruses) that live on or in the human body, for a given human. Microbes outnumber human cells in a 10:1 ratio. Most microbes live in the gut, particularly the large intestine. The number of genes of all microbes in the microbiome is 200-fold that of the human genome. The microbiome may weigh as much as 2 kg. The bacteria help digest food, regulate the immune system, protect against other bacteria that cause disease, and produce vitamins (including the B vitamins 12, thiamine, and riboflavin; and Vitamin K, which is required for blood coagulation). The microbiome became generally recognized in the late 1990s. See, e.g., Marilyn Hair & Jon Sharpe, *Fast facts about the human microbiome*, CTR. FOR ECOGENETICS & ENVTL. HEALTH, UNIV. WASHINGTON (2014), incorporated by reference herein in its entirety.

The microbiome is essential for human development, immunity, and nutrition. Bacteria living in and on humans are not invaders but, rather, beneficial colonizers. Autoimmune diseases including diabetes, rheumatoid arthritis, muscular dystrophy, multiple sclerosis, and fibromyalgia are associated with dysfunctional microbiomes. Disease-causing microbes accumulate over time and change genetic activities and metabolic processes, triggering abnormal immune responses against substances and tissues that are, in fact, part of a healthy body. Autoimmune diseases appear to run in families not because of germline inheritance but, rather, by inheritance of the familial microbiome. See, e.g., Hair & Sharpe, 2014.

Humans are essentially sterile during gestation. During and after birth, however, every bodily surface, including the skin, mouth, and gut, becomes host to an enormous variety of microbes: bacterial, archaeal, fungal, and viral. Under normal circumstances, the microbes aid in food digestion and maintenance of immune systems; dysfunctional human microbiotas have been linked to conditions ranging from inflammatory bowel disease to antibiotic-resistant infections. See, e.g., X. C. Morgan & C. Huttenhower, *Chapter 12: human microbiome analysis*, 8 PLoS COMPUTATIONAL BIOLOGY e1002808 (2012), incorporated by reference herein in its entirety.

The gut microbiota is essential to human health throughout life. The gut microbiome is a vast collection of bacteria, viruses, fungi, and protozoa that colonize the gastrointestinal tract and outnumber human cells 10-fold. Exposures in early life [Mode of delivery (maternal microbes); infant diet (selective substrates); antibiotics (selective killing); probiotics (selective enrichment); and physical environment (environmental microbes)] results in colonization of gut microbiota which contributes to the development of the immune system, intestinal homeostasis, and host metabolism. Disruption of the gut microbiota is associated with a growing number of diseases. See, e.g., M. B. Azad, et al., *Gut microbiota of healthy Canadian infants: profiles by mode of delivery and infant diet at 4 months*, 185 CAN. MED. ASS'NJ. 385 (2013), incorporated by reference herein in its entirety. Recent advances in metagenomics have enhanced our understanding of the gut microbiome, suggesting that it can provide important immune and metabolic benefits to humans.

Interestingly, the intestinal microbiota affects the immune and/or inflammatory status of the host by modulating intestinal barrier function and by influencing the development of the immune response. The gut microbiome's influence on the human immune system is far-reaching and intricately designed to enable immune tolerance of dietary and environmental antigens and provide protection against potential pathogens and toxins. Several gut microbial structures that play an important role in barrier functions have been identified. The secreted protein, p40, from Lactobacilli LGG ameliorates cytokine-mediated apoptosis and disruption of the gut epithelial barrier, and flagellin from *Escherichia coli* Nissle is associated with induction of β-defensin 2 in epithelial cells. See, e.g., F. Yan, et al., *Colon-specific delivery of a probiotic-derived soluble protein ameliorates intestinal inflammation in mice through an EGFR-dependent mechanism*, 121 J. CLINICAL INVESTIGATION 2242 (2011); M. Schlee, et al., *Induction of human beta-defensin 2 by the probiotic Escherichia coli Nissle 1917 is mediated through flagellin*, 75 INFECTION & IMMUNITY 2399 (2007); each of which is incorporated by reference herein in its entirety. Gut microbiota has been shown to direct maturation of the host immune system, to play a key role in the induction of immunoglobulin ("Ig") A and germinal centers, and to drive Th1, Th17, and regulatory T cell ("Treg") development in the gut. See, e.g., S. K. Mazmanian, et al., *An immunomodulatory molecule of symbiotic bacteria directs maturation of the host immune system*, 122 CELL 107 (2005); H. L. Klaasen, et al., *Intestinal, segmented, filamentous bacteria in a wide range of vertebrate species*, 27 LABANIMAL 141 (1993); G. L. Talham, et al., *Segmented filamentous bacteria are potent stimuli of a physiologically normal state of the murine gut mucosal immune system*, 67 INFECTION & IMMUNITY 1992 (1999); H. Bauer, et al., *The response of the lymphatic tissue to the microbial flora. Studies on germfree mice*, 42 AM. J. PATHOLOGY 471 (1963); K. Atarashi, et al., *Induction of colonic regulatory T cells by indigenous Clostridium species*, 331 SCIENCE 337 (2011); V. Gaboriau-Routhiau, et al., *The key role of segmented filamentous bacteria in the coordinated maturation of gut helper T cell responses*, 31 IMMUNITY 677 (2009); I. I. Ivanov, et al., *Induction of intestinal Th17 cells by segmented filamentous bacteria*, 139 CELL 485 (2009); each of which is incorporated by reference herein in its entirety. In most individuals, the commensal-mediated induction of these different components of the immune response is beneficial for host health. However, the composition of the gut microbiota can differentially influence various immune cell populations and adversely affect autoimmune/inflammatory disease-susceptible hosts, e.g., the presence of segmented filamentous bacteria ("SFB") has been associated with a strong Th17 response and development of Th17-mediated diseases. See, e.g., Y. K. Lee, et al., *Proinflammatory T-cell responses to*

*gut microbiota promote experimental autoimmune encephalomyelitis*, 108 (Suppl. 1) PROCEEDINGS NAT'L ACAD. SCI. USA 4615 (2011); R. Stepankova, et al., *Segmented filamentous bacteria in a defined bacterial cocktail induce intestinal inflammation in SCID mice reconstituted with CD45RBhigh CD4+ T cells*, 13 INFLAMMATORY BOWEL DISEASES 1202 (2007); H. J. Wu, et al., *Gut-residing segmented filamentous bacteria drive autoimmune arthritis via T helper 17 cells*, 32 IMMUNITY 815 (2010); each of which is incorporated by reference herein in its entirety.

Interaction between the gut microbiota and host play an important role in the regulation of a multitude of physiological processes. Current evidence suggests that gut-host communication effects cognition, epithelial protection, mitochondrial function, and may shape metabolic and immune network activity. See, e.g., S. Misra & B. Medhi, *Role of probiotics as memory enhancer*, 45 INDIAN J. PHARMACOLOGY 311 (2013); A. Clark & N. Mach, *The crosstalk between the gut microbiota and mitochondria during exercise*, 8 FRONTIERS IN PHYSIOLOGY (2017); N. Mach & D. Fuster-Botella, *Endurance exercise and gut microbiota: a review*, 6 J. SPORT & HEALTH SCI. 179 (2016); each of which is incorporated by reference herein in its entirety.

As part of immune modulation because of the consumption of probiotics, systemic humoral immune responses could be induced as well. Several studies confirmed that immunoglobulins, main mediators of humoral immunity, were influenced by oral probiotic administration. See, e.g., T. S. Kemgang, et al., 2014; A. C. Ouwehand, et al., *Lactobacillus acidophilus supplementation in human subjects and their resistance to enterotoxigenic Escherichia coli infection*, 111 BRITISH J. NUTRITION 465 (2014); D. Paineau, et al., *Effects of seven potential probiotic strains on specific immune responses in healthy adults: A double-blind, randomized, controlled trial*, 53 FEMS IMMUNOLOGY & MEDICAL MICROBIOLOGY 107 (2008); K. N. Sindhu, et al., *Immune response and intestinal permeability in children with acute gastroenteritis treated with Lactobacillus rhamnosus GG: A randomized, double-blind, placebo-controlled trial*, 58 CLINICAL INFECTIOUS DISEASES 1107 (2014); each of which is incorporated by reference herein in its entirety. Tight junctions are protein structures that represent the major barrier within the intestinal paracellular pathway. Tight junctions seal the paracellular space between epithelial cells and regulate the movement of fluid, macromolecules, and leukocytes between the bloodstream and the intestinal lumen, and vice versa. See, e.g., A. Fasano, *Pathological and therapeutical implications of macro-molecule passage through the tight junction, in* TIGHT JUNCTIONS 697 (2d ed., M. Cereijido & J. Anderson, eds., CRC Press 2001), incorporated by reference herein in its entirety. Tight junctions consist of more than 50 proteins and are regarded to be key factors of GI permeability. See, e.g., D. Ulluwishewa, et al., *Regulation of tight junction permeability by intestinal bacteria and dietary components*, 141 J. NUTRITION 769 (2011), incorporated by reference herein in its entirety. Commensal and probiotic strains modulate the amount of tight junction proteins at the cell boundaries and can prevent or reverse adverse effects of pathogens. Several probiotic strains such as *Lactobacillus plantarum, Baceteroides thetaiotaomicron* ATCC29184, *Escherichia coli* Nissle 1917, *Bifidobacterium longum* SP 07/3, and *Lactobacillus rhamnosus* GG revealed beneficial impacts on tight junction and intestinal barrier function. See, e.g., H. Qin, et al., *L. plantarum prevents enteroinvasive Escherichia coli-induced tight junction proteins changes in intestinal epithelial cells*, 9 BMC MICROBIOLOGY 63 (2009); R. C. Anderson, et al., *Lactobacillus plantarum DSM 2648 is a potential probiotic that enhances intestinal barrier function*, 309 FEMS MICROBIOLOGY LETTERS 184 (2010); J. Karczewski, et al., *Regulation of human epithelial tight junction proteins by Lactobacillus plantarum in vivo and protective effects on the epithelia barrier*, 298 AM. J. PHYSIOLOGY-GASTROTINESTINAL & LIVER PHYSIOLOGY G851 (2010); S. Resta-Lenert & K. E. Barrett, *Probiotics and commensals reverse TNF-alpha-and IFN-gamma-induced dysfunction in human intestinal epithelial cells*, 130 GASTROENTEROLOGY 731 (2006); S. N. Ukena, et al., *Probiotic Escherichia coli Nissle 1917 inhibits leaky gut by enhancing mucosal integrity*, 12 PLoS ONE e1308 (2007); D. Ghadimi, et al., *Effect of natural commensal-origin DNA on toll-like receptor 9 (TLR9) signaling cascade, chemokine IL-8 expression, and barrier integrity of polarized intestinal epithelial cells*, 16 INFLAMMATORY BOWEL DISEASES 410 (2010); each of which is incorporated by reference herein in its entirety. Moreover, various dietary components like polyphenols, proteins, or amino acids are postulated to regulate epithelial permeability by modifying expression and localization of tight junction proteins in the paracellular space. See, e.g., D. Ulluwishea, et al., 2011.

The term "probiotics" can refer to live microorganisms, which when administered in adequate amounts, confer a health benefit on the host. See, e.g., FAO/WHO, *Health and Nutrition Properties of Probiotics in Food including Powder Milk with Live Lactic Acid Bacteria: Report of a Joint FAO/WHO Expert Consultation on Evaluation of Health and Nutritional Properties of Probiotics in Food including Powder Milk with Live Lactic Acid Bacteria*, Report 2001, Cordoba, Argentina, 1-4 Oct. 2001, Report No. 0254-4725, incorporated by reference herein in its entirety. *Lactobacillus* and *Bifidobacterium* are the most commonly used bacterial probiotics.

Probiotics supply benefits to their hosts primarily by supporting the proliferation of beneficial gut microflora. The intestinal microbiota is the largest source of microbial stimulation that has potential for both harmful as well as beneficial impact in human health and sickness. See, e.g., Anil Minocha, *Probiotics for Preventive Health*, 24 NUTRITION IN CLINICAL PRACTICE 227 (2009), incorporated by reference herein in its entirety. About 60-80% of immune system components can be found in the gut. As such, attention has been focused on the role of probiotics in boosting immunity to prevent or treat infections, chronic inflammatory diseases, and allergic disorders. Numerous animal studies have documented the immune-boosting properties of probiotics. It has been demonstrated that formula acidified with live *Lactococcus lactis* formula provided superior protection against pulmonary and GI bacterial colonization as well as translocation in rabbits. See, e.g., M. R. McVay, et al., *Formula fortified with live probiotic culture reduces pulmonary and gastrointestinal bacterial colonization and translocation in a newborn animal model*, 43 J. PEDIATRIC SURGERY 25 (2008), incorporated by reference herein in its entirety. When children attending child care centers take probiotics, it reduces infections, suggesting that probiotics impede the spread of infections. See, e.g., Z. Weizman, et al., *Effect of a probiotic infant formula on infections in child care centers: comparison of two probiotic agents*, 115 PEDIATRICS 5 (2005); C. W. Binns, et al., *The CUPDAY study: prebiotic probiotic milk product in 1-3-year-old children attending childcare centres*, 96 ACTA PAEDIATRICA 1646 (2007); each of which is incorporated by reference herein in its entirety. There is potential for a 20% reduction in the duration of winter infections in the elderly as a result of probiotic therapy. See, e.g., P. Turchet, et al., *Effect of fermented milk containing the probiotic*

*Lactobacillus casei DN*-114001 *on winter infections in free-living elderly subjects: a randomized, controlled pilot study*, 7 J. NUTRITION HEALTH & AGING 75 (2003), incorporated by reference herein in its entirety. Regular intake of probiotics can reduce potentially pathogenic bacteria in the upper respiratory tract, suggesting a linkage of the lymphoid tissue between the gut and the upper respiratory tract. See, e.g., U. Glück & J. O. Gebbers, *Ingested probiotics reduce nasal colonization with pathogenic bacteria (Staphylococcus aureus, Streptococcus pneumoniae, and beta-hemolytic streptococci)*, 77 AM. J. CLINICAL NUTRITION 517 (2003), incorporated by reference herein in its entirety.

Further, probiotics are reported to exert their beneficial effects by producing bacteriostatic or bactericidal agents, competitively excluding pathogenic bacteria, or regulating immunomodulatory effects. See, e.g., P. M. Sherman, et al., *Probiotics Reduce Enterohemorrhagic Escherichia coli O157:H7-and Enteropathogenic E. coli O127:H6-Induced Changes in Polarized T84 Epithelial Cell Monolayers by Reducing Bacterial Adhesion and Cytoskeletal Rearrangements*, 73 INFECTION & IMMUNITY 5183 (2005); S. C. Corr, et al., *Bacteriocin production as a mechanism for the antiinfective activity of Lactobacillus salivarius UCC* 118, 104 PROCEEDINGS NAT'L ACADEMY SCIS. 7617 (2007); M. Takahashi, et al., *The effect of probiotic treatment with Clostridium butyricum on enterohemorrhagic Escherichia coli O157:H7 infection in mice*, 41 FEMS IMMUNOLOGY & MEDICAL MICROBIOLOGY 219 (2004); K. Madsen, et al., *Probiotic bacteria enhance murine and human intestinal epithelial barrier function*, 121 GASTROENTEROLOGY 580 (2001); S. Resta-Lenert & K. E. Barrett, 2006; each of which is incorporated by reference herein in its entirety.

Furthermore, probiotics modulate the frequency of the tight junction proteins that act as a barrier in the intestinal paracellular pathway. See, e.g., John R. Kelly, et al., *Breaking down the barriers: the gut microbiome, intestinal permeability and stress-related psychiatric disorders*, 9 FRONTIERS IN CELLULAR NEUROSCIENCE 392 (2015), incorporated by reference herein in its entirety. *B. lactis* augmented formula, fed to preterm infants, resulted in decreased intestinal permeability as measured by the lactulose/mannitol ration at two, seven, and thirty days post birth. See, e.g., Z. Stratiki, et al., *The effect of a bifidobacter supplemented bovine milk on intestinal permeability of preterm infants*, 83 EARLY HUMAN DEVELOPMENT 575 (2007), incorporated by reference herein in its entirety. In a double-blinded, placebo-controlled, cross-over study *L. rahmnosus* 19070-2 and *L. reuteri* DSM 12246 were administered for six weeks to 41 children with moderate and severe atopic dermatitis, decreasing associated GI symptoms and influencing small intestinal permeability as measured by the lactulose-mannitol test. See, e.g., V. Rosenfeldt, et al., *Effect of probiotics on gastrointestinal symptoms and small intestinal permeability in children with atopic dermatitis*, 145 J. PEDIATRICS 612 (2004), incorporated by reference herein in its entirety. Some of the strongest evidence for the clinical role of probiotics comes from studies in patients with the brain-gut-axis disorder, IBS. See, e.g., K. Whelan & E. M. Quigley, *Probiotics in the management of irritable bowel syndrome and inflammatory bowel disease*, 290 CURRENT OPINION IN GASTROENTEROLOGY 184 (2013); R. Orel & T. Kamhi Trop, *Intestinal microbiota, probiotics and probiotics in inflammatory bowel disease*, 20 WORLD J. GASTROENTEROLOGY 11505 (2014); each of which is incorporated by reference herein in its entirety. A number of probiotics and commensal organisms, primarily lactic acid bacteria, have been shown to ameliorate certain IBS symptoms. See, e.g., N. Hoveyda, et al., *A systematic review and meta-analysis: probiotics in the treatment of irritable bowel syndrome*, 9 BMC GASTROENTEROLOGY 15 (2009); G. Clarke, et al., *Review article: probiotics for the treatment of irritable bowel syndrome—focus on lactic acid bacteria*, 35 ALIMENTARY PHARMACOLOGY & THERAPEUTICS 403 (2012); M. Ortiz-Lucas, et al., *Effect of probiotic species on irritable bowel syndrome symptoms: a bring up to date meta-analysis*, 105 REVISTA ESPAÑOLA DE ENFERMEDADES DIGESTIVAS 19 (2013); J. S. Yoon, et al., *Effect of multi-species probiotics on irritable bowel syndrome: a randomized, double-blind, placebo-controlled trial*, 29 J. GASTROENTEROLOGY & HEPATOLOGY 52 (2014); T. Didari, et al., *Effectiveness of probiotics in irritable bowel syndrome: updated systematic review with meta-analysis*, 21 WORLD J. GASTROENTEROLOGY 3072 (2015); each of which is incorporated by reference herein in its entirety. Some beneficial effects of probiotics on IBS symptoms may, at least, relate to the anti-inflammatory effects of particular organisms. See, e.g., L. O'Mahony, et al., *Lactobacillus and Bifidobacterium in irritable bowel syndrome: symptom responses and relationship to cytokine profiles*, 128 GASTROENTEROLOGY 541 (2005), incorporated by reference herein in its entirety. Moreover, probiotics in accordance with preclinical evidence can improve intestinal barrier function under pathological conditions in human populations. In a randomized single blind placebo controlled study, a fermented milk drink containing *Streptococcus* thermophiles, *L. bulgaricus*, *L. acidophilus*, and *B. longum* decreased small intestinal permeability, though colonic permeability was unaltered. See, e.g., J. Zeng, et al., *Clinical trial: effect of active lactic acid bacteria on mucosal barrier function in patients with diarrhea-predominant irritable bowel syndrome*, 28 ALIMENTARY PHARMACOLOGY & THERAPEUTICS 994 (2008), incorporated by reference herein in its entirety.

By enhancing intestinal barrier function, probiotics serve as preventative agents to defend against adverse effects of pathogens, promoting positive effects on digestion and immune health. See, e.g., Jurgen Karczewski, et al., 2010; M. Gleeson, et al., 2011. Certain probiotic strains have given significant and promising results in human clinical trials and experimental animal models of gastrointestinal disease. The enhancement of epithelial barrier function is one of the proposed mechanisms by which certain probiotic organisms may confer beneficial activities. See, e.g., I. Dotan & D. Rachmilewitz, *Probiotics in inflammatory bowel disease: possible mechanisms of action*, 21 CURRENT OPINION IN GASTROENTEROLOGY 426 (2005), incorporated by reference herein in its entirety. Some probiotic studies in humans have reported a decrease in intestinal permeability, whereas others have been negative or inconclusive, suggesting that this activity may depend on the probiotic strain and species as well as the target population and its resilience capacity of the intestinal mucosa. See, e.g., V. Rosenfeldt, et al., 2004; Z. Stratiki, et al., 2007; M. Gotteland, et al., *Effect of Lactobacillus ingestion on the gastrointestinal mucosal barrier alterations induced by indomethacin in humans*, 15 ALIMENTARY PHARMACOLOGY & THERAPEUTICS 11 (2001); C. E. McNaught, et al., *A prospective randomized trial of probiotics in critically ill patients*, 24 CLINICAL NUTRITION 211 (2005); each of which is incorporated by reference herein in its entirety. Evidence for probiotic effects on barrier function has also been demonstrated in rat models of chronic stress, hemorrhagic shock, and sepsis although the mechanisms have not been elucidated. See, e.g., H. L. Qin, et al., *Effect of lactobacillus on the gut microflora and barrier function of the rats with abdominal infection*, 11 WORLD J. GASTROENTEROLOGY 2591 (2005); M. Zareie, et al., *Probiotics prevent* bacterial translocation and improve intestinal barrier function in rats following chronic psychological stress, 55 GUT 1553 (2006); each of which is incorporated by reference herein in its entirety.

There is increasing evidence that probiotic supplementation, alone or in combination with other preventative agents such as prebiotics, can reduce the number, duration, and severity of acute infectious diarrhea and upper respiratory tract infections in the general population and in at-risk subgroups, such as the elderly. See, e.g., Nicholas P. West, et al., *Lactobacillus fermentum (PCC®) supplementation and gastrointestinal and respiratory-tract illness symptoms: a randomized control trial in athletes*, 10 NUTRITION J. 30 (2011); M. de Vrese & J. Schrezenmeir, *Probiotics, prebiotics, and synbiotics*, 111 ADVANCES IN BIOCHEMICAL ENGINEERING/BIOTECHNOLOGY 1 (2008); M. de Vrese, et al., *Effect of Lactobacillus gasseri PA 16/8, Bifidobacterium longum SP 07/3, B. bifidum MF 20/5 on common cold episodes: a double blind, randomized, controlled trial*, 24 CLINICAL NUTRITION 481 (2005); S. Sazawal, et al., *Efficacy of probiotics in prevention of acute diarrhea: a meta-analysis of masked, randomized, placebo-controlled trials*, 6 LANCET INFECTIOUS DISEASES 374 (2006); E. Guillemard, et al., *Consumption of a fermented dairy product containing the probiotic Lactobacillus casei DN-114001 reduces the duration of respiratory infections in the elderly in a randomised controlled trial*, 103 BRITISH J. NUTRITION 58 (2010); each of which is incorporated by reference herein in its entirety. Three studies indicated that probiotic supplementation might be useful for enhancing immunity and reducing the duration of URTIs and gastrointestinal illnesses in endurance-based athletes, whereas probiotic supplementation by commando cadets during a training and combat course had little effect on the incidence of URTIs. See, e.g., M. Gleeson, et al., 2011; R. A. Kekkonen, et al., *The effect of probiotics on respiratory infections and gastrointestinal symptoms during training in marathon runners*, 17 INT'L J. SPORT NUTRITION & EXERCISE METABOLISM 352 (2007); A. J. Cox, et al., *Oral administration of the probiotic Lactobacillus fermentum VRI-003 and mucosal immunity in endurance athletes*, 44 BRITISH J. SPORTS MEDICINE 222 (2010); E. Tiollier, et al., *Effect of a probiotics supplementation on respiratory infections and immune and hormonal parameters during intense military training*, 172 MILITARY MEDICINE 1006 (2007); each of which is incorporated by reference herein in its entirety.

Additionally, it appears that the beneficial effects of probiotics may be strain-specific, with a majority of probiotic studies investigating *Bifidobacterium* and *Lactobacillus* strains in various special groups (i.e., diabetic, obese) of the general population. Overweight Japanese adults exhibited a significantly decreased visceral fat area, body weight, body mass index ("BMI"), and waist and hip circumferences following consumption of fermented milk containing *Lactobacillus* gasseri SBT2055 ("LG2055") at 200 g/d for 12 weeks. See, e.g., Y. Kadooka, et al., *Regulation of abdominal adiposity by probiotics (Lactobacillus gasseri SBT2055) in adults with obese tendencies in a randomized controlled trial*, 64 EUR. J. CLINICAL NUTRITION 636 (2010); Y. Kadooka, et al., *Effect of Lactobacillus gasseri SBT2055 in fermented milk on abdominal adiposity in adults in a randomized controlled trial*, 110 BRITISH J. NUTRITION 1696 (2013); each of which is incorporated by reference herein in its entirety. Small, but significant, body mass and fat mass loss has been reported in individuals with obesity following consumption of some probiotic strains. See, e.g., Kristin L. Osterberg, et al., *Probiotic Supplementation Attenuates Increases in Body Mass and Fat Mass During High-Fat Diet in Healthy Young Adults*, 23 OBESITY 2364 (2015); M. Sánchez, et al., *Effect of Lactobacillus rhamnosus CGMCC1.3724 supplementation on weight loss and maintenance in obese men and women*, 111 BRITISH J. NUTRITION 1507 (2014); each of which is incorporated by reference herein in its entirety. Less body mass and fat mass gain and prevention of insulin resistance was reported in young, healthy subjects consuming a single probiotic strain during 7 days of high-fat overfeeding. See, e.g., C. J. Hulston, et al., *Probiotic supplementation prevents high-fat, overfeeding-induced insulin resistance in human subjects*, 113 BRITISH J. NUTRITION 596 (2015), incorporated by reference herein in its entirety. Rats fed a diet containing fermented skim milk supplemented with LG2055 showed a lower maximal rate of lymphatic lipid absorption compared with rats fed a diet containing non-fermented skim milk, findings which were supported by the observation of increased fecal fatty acid excretion. See, e.g., E. M. Hamad, et al., *Milk fermented by Lactobacillus gasseri SBT2055 influences adipocyte size via inhibition of dietary fat absorption in Zucker rats*, 101 BRITISH J. NUTRITION 716 (2009), incorporated by reference herein in its entirety. Japanese hypertriacylglycerolemic subjects who consumed fermented milk containing LG2055 at 200 g/d for 4 weeks demonstrated significantly decreased postprandial serum lipid concentrations after the intake of oral fat-loading test meals. See, e.g., A. Ogawa, et al., *Lactobacillus gasseri SBT2055 reduces postprandial and fasting serum non-esterified fatty acid levels in Japanese hypertriacylglycerolemic subjects*, 13 LIPIDS IN HEALTH & DISEASE 36 (2014), incorporated by reference herein in its entirety.

In recent years, whole genome sequencing and mining has revolutionized the characterization of novel bacterial strains and their potential bioactive secondary metabolites. Currently, the genomes of all the type strains of the *Bacillus subtilis* species complex have been determined and permit definitive taxonomic assignment of strains in this clade. In addition, the genomics revolution has created a plethora of sequencing data that, when combined with prediction tools, such as AntiSMASH, allow for the evaluation of known, distinct, and new bioactive metabolites in the *B. subtilis* complex. See, e.g., G. Aleti, et al., *Genome mining: prediction of lipopeptides and polyketides from Bacillus and related Firmicutes*, 13 COMPUTATIONAL & STRUCTURAL BIOTECHNOLOGY J. 192 (2015); H. Fan, et al., *Fengycin produced by Bacillus subtilis 9407 plays a major role in the biocontrol of apple ring rot disease*, 199 MICROBIOLOGICAL RESEARCH 89 (2017); each of which is incorporated by reference herein in its entirety. The major classes of antifungals synthesized by *Bacillus subtilis* species complex are the cyclic lipopeptides ("CLPs"). Strains in the *Bacillus subtilis* group have been frequently reported to make the CLPs; fengycin, surfactin, and iturin-family compounds. See, e.g., C. A. Dunlap, et al., *Genomic analysis and secondary metabolite production in Bacillus amyloliquefaciens AS 43.3: a biocontrol antagonist of Fusarium Head Blight*, 64 BIOLOGICAL CONTROL 166 (2013); C. A. Dunlap, et al., *Genomic analysis of Bacillus subtilis OH 131.1 and coculturing with Cryptococcus flavescens for control of fusarium head blight*, 2 PLANT GENE 1 (2015); each of which is incorporated by reference herein in its entirety. These CLPs are secondary metabolites produced by non-ribosomal peptide synthetases. CLPs are produced by several species if *Bacillus*, namely *Bacillus subtilis, Bacillus pumilus, Bacillus licenformis, Bacillus velezensis*, and *Bacillus amyloliquefaciens* strains. See, e.g., N. Vanittanakom, et al., *Fengycin—a novel antifungal lipopeptide antibiotic produced by Bacillus subtilis F-29-3*, 39 J. ANTI- BIOTICS 888 (1986); N. I. Kalinovskaya, et al., *Characterization of surfactin-like cyclic depsipeptides synthesized by Bacillus pumilus from ascidian Halocynthia aurantium*, 4 MARINE BIOTECHNOLOGY 179 (2002); C. Leifert, et al., *Antibiotic production and biocontrol activity by Bacillus subtilis CL27 and Bacillus pumilus CL45*, 78 J. APPLIED MICROBIOLOGY 97 (1995); F. Peypoux, et al., *Recent trends in the biochemistry of surfactin*, 51 APPLIED MICROBIOLOGY & BIOTECHNOLOGY 553 (1999); J. M. Pallazzini, et al., *Bacillus velezensis RC 218 as a biocontrol agent to reduce Fusarium head blight and deoxynivalenol accumulation in wheat: genome sequencing and secondary metabolite cluster profiles*, 192 MICROBIOLOGICAL RESEARCH 30 (2016); I. Mnif & D. Ghribi, *Review lipopeptides biosurfactants: mean classes and new insights for industrial, biomedical, and environmental applications*, 104 PEPTIDE SCI. 129 (2015); T. Stein, *Bacillus subtilis antibiotics: structures, syntheses and specific functions*, 56 MOLECULAR MICROBIOLOGY 845 (2005); each of which is incorporated by reference herein in its entirety. These three aforementioned classes differ in type of peptide cyclization, amino acid residue substitution, and fatty acid chain length and composition. See, e.g. I. Mnif & D. Ghribi, 2015; J. Falardeau, et al., *Ecological and mechanistic insights into the direct and indirect antimicrobial properties of Bacillus subtilis lipopeptides on plant pathogens*, 39 J. CHEMICAL ECOLOGY 869 (2013); incorporated by reference herein in its entirety. Fengycin was the first discovered antifungal, surfactin is one of the most powerful biosurfactants, and the iturins produce many isomers with potent, broad-spectrum antifungal activity. See, e.g., R. Maget-Dana & F. Peypoux, *Iturins, a special class of pore-forming lipopeptides: biological and physicochemical properties*, 87 TOXICOLOGY 151 (1994); E. Ruiz-Sánchez, et al., *Antifungal activity and molecular identification of native strains of Bacillus subtilis*, 50 AGROCIENCIA 133 (2016); each of which is incorporated by reference herein in its entirety. Bio-pesticides derived from *Bacillus* species are known to be efficacious against a wide range of phytopathogens. C. Cao, et al., *Biopesticide controls of plant diseases: resources and products for organic farmers in Ohio*, FACT SHEET SAG-18-10 (2010); D. R. Fravel, *Commercialization and implementation of biocontrol*, 43 ANNUAL REVIEW PHYTOPATHOLOGY 337 (2005); each of which is incorporated by reference herein in its entirety.

Surfactin, iturin, and fengycins are also considered to be antibiotics due to their broad antimicrobial activities. Bioactive properties result mostly from the CLPs' capability to disturb the structure and functions of biological membranes, leading to the increase of membrane permeability. See, e.g., O. S. Ostroumova, et al., *Surfactin activity depends on the membrane dipole potential*, 26 LANGMUIR 15092 (2010); M. Deleu, et al., *Effects of surfactin on membrane models displaying lipid phase separation*, 1828 BIOCHIMICA ET BIOPHYSICA ACTA 801 (2013); each of which is incorporated by reference herein in its entirety. These compounds modify bacterial surface hydrophobicity and affect the development of flagella, which could be the source of their anti-adhesive properties. They are also known to have a stimulating effect on the biofilm dispersion process. See, e.g., K. Paraszkiewicz & J. Długoński, *Remediation of heavy metal-contaminated soil by microbial surfactants*, 2 BIOTECHNOLOGJA 81 (2007); F. Rivardo, et al., *Anti-adhesion activity of two biosurfactants produced by Bacillus spp. prevents biofilm formation of human bacterial pathogens*, 83 APPLIED MICROBIOLOGY & BIOTECHNOLOGY 541 (2009); T. Janek, et al., *Anti-adhesive activity of the biosurfactant pseudofactin II secreted by the Arctic bacterium Pseudomonas fluorescens BD5*, 23 BMC MICROBIOLOGY 12 (2012); each of which is incorporated by reference herein in its entirety. Recently, *B. subtilis* I' la strain has been recognized as a surfactin, iturin, and fengycin co-producer. See, e.g., G. Plaza, et al., *Detection of biosurfactants in Bacillus species: genes and products identification*, 119 J. APPLIED MICROBIOLOGY 1023 (2015), incorporated by reference herein in its entirety. Simultaneous synthesis of those three biosurfactants is a unique feature due to the *Bacillus* LPs synergic mode of action.

If new methods of treating, reducing, removing, or preventing accumulation of bacteria, fungus, and/or yeast on a surface, or treating, reducing, removing, or preventing fungal, bacterial, and/or yeast infections in a human subject could be found, this would be a useful contribution to the art. Further, if new probiotic-containing composition(s) that treat, reduce, remove, or prevent accumulation of bacteria, fungus, and/or yeast on a surface, or treat, reduce, remove, or prevent fungal, bacterial, and/or yeast infections in a human subject could be found, this would also be a useful contribution to the art.

SUMMARY OF THE INVENTION

In an embodiment, a composition according to the present disclosure repels, reduces, and/or removes plant fungal pathogens.

In another embodiment, a composition according to the present disclosure repels, reduces, and/or removes fungal pathogens.

In yet another embodiment, a composition according to the present invention transports iron across cell membranes.

In yet another embodiment, a composition according to the present disclosure repels, reduces, and/or removes bacterial pathogens.

In yet another embodiment, a composition according to the present disclosure includes secreted material in a carrier.

In yet another embodiment, a composition according to the present disclosure is formulated for use as a cream, gel, or spray.

In yet another embodiment, a composition according to the present disclosure is a pharmaceutical composition.

In yet another embodiment, a composition according to the present disclosure is formulated for topical administration.

In yet another embodiment, a composition according to the present disclosure is formulated for use in medicine.

In yet another embodiment, a composition according to the present disclosure is formulated for use in a method of preventing, removing, reducing, or treating a bacterial or fungal infection.

In yet another embodiment, a composition according to the present disclosure is formulated for use in a method of preventing, removing, reducing, or treating a bacteria or fungal infection, wherein the infection is an infection of the epidermis of a mammal.

In yet another embodiment, a composition according to the present disclosure is formulated for use in a method of preventing, removing, reducing, or treating a bacterial, yeast, or fungal infection.

In yet another embodiment, a composition according to the present disclosure is formulated for use in a method of preventing, removing, reducing, or treating a bacterial, yeast, or fungal infection, wherein the infection is an infection of the epidermis of a mammal.

In yet another embodiment, a composition according to the present disclosure includes secreted material in a carrier, wherein the carrier is selected from the group consisting of an emulsion, cream, lotion, gel, oil, ointment, suspension, aerosol spray, powder, aerosol powder, and semisolid formulation.

In yet another embodiment, a composition according to the present disclosure includes secreted material in a carrier, wherein the carrier is suitable for topical application to skin or a mucous membrane of a mmal.

In yet another embodiment, a composition according to the present disclosure can include from a bout 1% to about 75% emu oil by weight.

In yet another embodiment, a composition according to the present disclosure includes secreted material in a carrier, further including an effective amount of a fructooligosaccharide.

In yet another embodiment, a composition according to the present disclosure includes secreted material in a carrier, further including an effective amount of a fructooligosaccharide, wherein the fructooligosaccharide is present in an amount of from about 10 to about 1000 milligrams per gram of composition.

In yet another embodiment, a composition according to the present disclosure includes secreted material in a carrier, further including an effective amount of a fructooligosaccharide, wherein the fructooligosaccharide is present in an amount of from about 100 to about 500 milligrams per gram of composition.

In yet another embodiment, a composition according to the present disclosure includes secreted material in a carrier, wherein the carrier can include media obtained from a culture containing a probiotic bacteria.

In yet another embodiment, a composition according to the present disclosure is formulated for use as an anti-fungal composition.

In yet another embodiment, a composition according to the present disclosure is formulated for use as an anti-bacterial composition.

In yet another embodiment, a composition according to the present disclosure includes secreted material in a carrier, wherein the carrier can include media obtained from a culture containing a probiotic bacteria, further wherein the probiotic bacteria is included in the composition in the form of spores.

In yet another embodiment, a composition according to the present disclosure includes secreted material in a carrier, wherein the carrier can include media obtained from a culture containing a probiotic bacteria, further wherein the probiotic bacteria is included in the composition in the form of a dried cell mass.

In yet another embodiment, a composition according to the present disclosure includes secreted material in a carrier, wherein the carrier can include media obtained from a culture containing a probiotic bacteria, further wherein the culture containing probiotic bacteria contains $10^3$ to $10^{12}$ viable bacteria or spores per gram of composition.

In yet another embodiment, a composition according to the present disclosure includes secreted material in a carrier, wherein the carrier can include media obtained from a culture containing a probiotic bacteria, further wherein the probiotic bacteria is a *Bacillus* spp. bacteria.

In yet another embodiment, a composition according to the present disclosure includes secreted material in a carrier, wherein the carrier can include media obtained from a culture containing a probiotic bacteria, further wherein the probiotic bacteria is a strain of *Bacillus subtilis*.

In yet another embodiment, a composition according to the present disclosure includes secreted material in a carrier, wherein the carrier can include media obtained from a culture containing a probiotic bacteria, further wherein the probiotic bacteria is *Bacillus subtilis* DE111.

In yet another embodiment, a composition according to the present disclosure includes secreted material in a carrier, wherein the carrier includes substantially no intact probiotic bacteria, lysed bacteria, or bacterial fragments.

In yet another embodiment, a composition according to the present disclosure includes an extracellular product of a probiotic bacteria in a pharmaceutically acceptable carrier suitable for topical administration to skin or a mucous membrane of a mammal.

In yet another embodiment, a composition according to the present disclosure includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria.

In yet another embodiment, a composition according to the present disclosure includes surfactin in a carrier.

In yet another embodiment, a composition according to the present disclosure includes iturin in a carrier.

In yet another embodiment, a composition according to the present disclosure includes bacillomycin in a carrier.

In yet another embodiment, a composition according to the present disclosure includes fengycin in a carrier.

In yet another embodiment, a composition according to the present disclosure includes iturin, bacillomycin, and/or fengycin in a carrier.

In yet another embodiment, a composition according to the present disclosure includes bacillibactin in a carrier.

In yet another embodiment, a composition according to the present disclosure includes bacillysin in a carrier.

In yet another embodiment, a composition according to the present disclosure includes subtilosin in a carrier.

In yet another embodiment, a composition according to the present disclosure includes sublancin in a carrier.

In yet another embodiment, a composition according to the present disclosure includes bacillysin, sublancin, and/or sublancin in a carrier.

In an embodiment, a method of preventing, removing, reducing, and/or treating a bacterial, yeast, and/or fungal infection in a mammal according to the present disclosure can include the steps of: (a) providing a composition that repels, reduces, and/or removes plant fungal pathogens; and (b) administering the composition to the mammal. The process described herein provides a method of preventing, removing, reducing, and/or treating a bacterial, yeast, and/or fungal infection in a mammal.

In another embodiment, a method of preventing, removing, reducing, and/or treating a bacterial, yeast, and/or fungal infection in a mammal according to the present disclosure can include the steps of: (a) providing a composition that repels, reduces, and/or removes fungal pathogens; and (b) administering the composition to the mammal. The process described herein provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal according to the present disclosure can include the steps of: (a) providing a composition that transports iron across cell membranes; and (b) administering the composition to the mammal. The process described herein provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal according to the present disclosure can include the steps of: (a) providing a composition that repels, reduces, and/or removes bacterial pathogens; and (b) administering the composition to the mammal. The process described herein provides a method of preventing, removing, reducing, and/or treating a bacterial, yeast, and/or fungal infection in a mammal.

In an embodiment, a method of preparing a surface according to the present disclosure can include the steps of: (a) providing a composition that repels, reduces, and/or removes plant fungal pathogens; and (b) applying the composition to the surface. The process described herein provides a method of preparing a surface.

In another embodiment, a method of preparing a surface according to the present disclosure can include the steps of: (a) providing a composition that repels, reduces, and/or removes fungal pathogens; and (b) applying the composition to the surface. The process described herein provides a method of preparing a surface.

In yet another embodiment, a method of preparing a surface according to the present disclosure can include the steps of: (a) providing a composition that transports iron across cell membranes; and (b) applying the composition to the surface. The process described herein provides a method of preparing a surface.

In yet another embodiment, a method of preparing a surface according to the present disclosure can include the steps of: (a) providing a composition that transports iron across cell membranes; and (b) applying the composition to the surface. The process described herein provides a method of preparing a surface.

In an embodiment, a method of inhibiting growth or activity of bacteria, yeast, and/or fungi on skin or a mucous membrane of a mammal according to the present disclosure can include the steps of: (a) providing a composition that repels, reduces, and/or removes plant fungal pathogens, wherein the composition includes an extracellular product of a strain of *Bacillus subtilis*; (b) administering the composition to the skin or mucous membrane of the mammal; and (c) maintaining the composition on the skin or mucous membrane of the mammal for sufficient time to inhibit the growth of the bacteria, yeast, and/or fungi. The process described herein provides a method of inhibiting growth or activity of bacteria, yeast, and/or fungi on skin or a mucous membrane of a mammal.

In another embodiment, a method of inhibiting growth or activity of bacteria, yeast, and/or fungi on skin or a mucous membrane of a mammal according to the present disclosure can include the steps of: (a) providing a composition that repels, reduces, and/or removes fungal pathogens, wherein the composition includes an extracellular product of a strain of *Bacillus subtilis*; (b) administering the composition to the skin or mucous membrane of the mammal; and (c) maintaining the composition on the skin or mucous membrane of the mammal for sufficient time to inhibit the growth of the bacteria, yeast, and/or fungi. The process described herein provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal according to the present disclosure can include the steps of: (a) providing a composition that transports iron across cell membranes, wherein the composition includes an extracellular product of a strain of *Bacillus subtilis*; (b) administering the composition to the skin or mucous membrane of the mammal; and (c) maintaining the composition on the skin or mucous membrane of the mammal for sufficient time to inhibit the growth of the bacteria, yeast, and/or fungi. The process described herein provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal according to the present disclosure can include the steps of: (a) providing a composition that repels, reduces, and/or removes bacterial pathogens, wherein the composition includes an extracellular product of a strain of *Bacillus subtilis*; (b) administering the composition to the skin or mucous membrane of the mammal; and (c) maintaining the composition on the skin or mucous membrane of the mammal for sufficient time to inhibit the growth of the bacteria, yeast, and/or fungi. The process described herein provides a method of inhibiting growth or activity of bacteria, yeast, and/or fungi on skin or a mucous membrane of a mammal.

In yet another embodiment, method of inhibiting growth or activity of bacteria, yeast, and/or fungi on skin or a mucous membrane of a mammal according to the present disclosure can include the steps of: (a) providing a composition that repels, reduces, and/or removes plant fungal pathogens, wherein the composition includes a *Bacillus* spp bacteria; (b) applying the composition to a solid surface; (c) contacting the solid surface with the composition applied thereto to skin or a mucous membrane of a mammal; and (d) maintaining contact between the solid surface with the composition applied thereto and the skin or mucous membrane of the mammal for a duration of time sufficient for inhibition of growth of bacteria, yeast, and/or fungi on the skin or mucous membrane of the mammal. The process described herein provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal according to the present disclosure can include the steps of: (a) providing a composition that repels, reduces, and/or removes fungal pathogens, wherein the composition includes a *Bacillus* spp bacteria; (b) applying the composition to a solid surface; (c) contacting the solid surface with the composition applied thereto to skin or a mucous membrane of a mammal; and (d) maintaining contact between the solid surface with the composition applied thereto and the skin or mucous membrane of the mammal for a duration of time sufficient for inhibition of growth of bacteria, yeast, and/or fungi on the skin or mucous membrane of the mammal. The process described herein provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal according to the present disclosure can include the steps of: (a) providing a composition that transports iron across cell membranes, wherein the composition includes a *Bacillus* spp bacteria; (b) applying the composition to a solid surface; (c) contacting the solid surface with the composition applied thereto to skin or a mucous membrane of a mammal; and (d) maintaining contact between the solid surface with the composition applied thereto and the skin or mucous membrane of the mammal for a duration of time sufficient for inhibition of growth of bacteria, yeast, and/or fungi on the skin or mucous membrane of the mammal. The process described herein provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal, including the steps of: (a) providing a composition that repels, reduces, and/or removes bacterial pathogens, wherein the composition includes a *Bacillus* spp bacteria; (b) applying the composition to a solid surface; (c) contacting the solid surface with the composition applied thereto to skin or a mucous membrane of a mammal; and (d) maintaining contact between the solid surface with the composition applied thereto and the skin or mucous membrane of the mammal for a duration of time sufficient for inhibition of growth of bacteria, yeast, and/or fungi on the skin or a mucous membrane of the mammal. The process described herein above provides a method of inhibiting growth or activity of bacteria, yeast, and/or fungi on skin or a mucous membrane of a mammal.

In an embodiment, an article of manufacture that prevents, removes, reduces, and/or treats a bacterial, yeast, and/or fungal infection can include: a flexible article that can be affixed to skin or a mucous membrane of a mammal; and an effective amount of a *Bacillus* spp bacteria applied to the flexible article; wherein the *Bacillus* spp bacteria effects inhibitory activity on the bacterial, yeast, and/or fungal infection that occurs adjacent to or on the skin or mucous membrane of the mammal.

In an embodiment, a method of preparing a composition that prevents, removes, reduces, and/or treats a bacterial, yeast, and/or fungal infection can include the steps of: (a) culturing *Bacillus subtilis* DE111 in media, so as to produce a composition that prevents, removes, reduces, and/or treats a bacterial, yeast, and/or fungal infection. The process described herein above provides a method of preparing a composition that prevents, removes, reduces, and/or treats a bacterial, yeast, and/or fungal infection.

DETAILED DESCRIPTION

Figure 1:
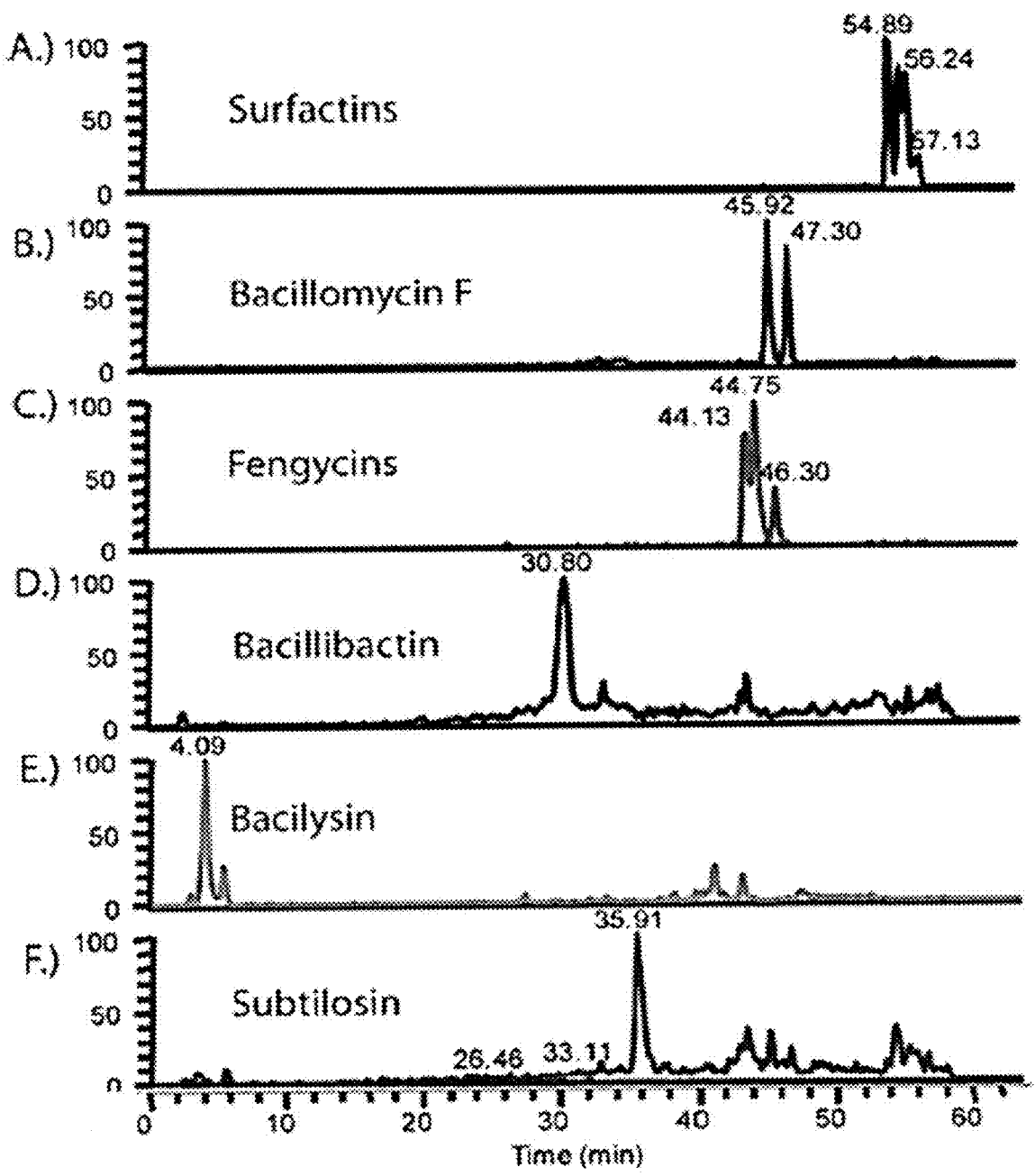
FIG. 1 depicts extracted ion-chromatograms (LC-MS) of secondary metabolites of *Bacillus subtilis* DE111. Panel A: m/z 1022-1023; 1036-1037; and 1044-1045; corresponding to surfactin [M+H]+ components. Panel B: m/z 1085-1086; 1099-1100; corresponding to bacillomycin F [M+H]+. Panel C: m/z 746-747; 753-754; 1491-1492; 1506-1507; corresponding to [M+2H]2+ and [M+H]+ fengycins. Panel D: m/z 883-884; corresponding to bacillibactin [M+H]+. Panel E: m/z 271-272; corresponding to bacillysin [M+H]+. Panel F: m/z 1135-1136; 1701-1702; corresponding to subtilosin [M+3H]3+ and [M+2H]2+.

In certain embodiments, the present invention relates to novel uses of a *Bacillus subtilis* (*B. subtilis*)-containing composition for treating, reducing, removing, or preventing accumulation of bacteria, fungus, and/or yeast on a surface, or treating, reducing, removing, preventing fungal, bacterial, and/or yeast infection in a human subject. In other embodiments, the present invention relates to (*B. subtilis*)-containing compositions(s) that treat, reduce, remove, or prevent accumulation of bacteria, fungus, and/or yeast on a surface, or treat, reduce, remove, or prevent fungal, bacteria, and/or yeast infections in a human subject.

Currently, there is a rapid growth of interest in probiotics to promote better health and well-being, which shows a substantial promise to expand the food industry into new fields. Strains from genera of *Lactobacillus* and *Bifidobacterium* species, both of which are indigenous to the human intestine, are predominantly selected for use although some other species have also been used as well. Probiotics, also termed as functional foods, are commonly found in dairy products such as yogurt and cultured milk drinks or even in the form of health supplements.

Useful bacterial strains for probiotic compositions can include, but are not limited to, *Lactobacillus plantarum*, *Bifidobacterium* bifidum, *Bifidobacterium lactis*, *Lactobacillus rhamnosus*, *Lactobacillus acidophilus*, *Bacillus coagulans*, *Bacillus subtilis*, and the like.

The *Bacillus* species are rod-shaped, spore-forming, aerobic, gram-positive bacteria that are ubiquitous in nature. There is some evidence that *Bacillus subtilis* might be a part of the normal gut flora of humans. Some human intestinal biopsy samples have shown that *Bacillus subtilis* does populate the gut in humans as normal human intestinal flora. See, e.g., Junjie Qin, et al., *A human gut microbial gene catalogue established by metagenomics sequencing*, 464 NATURE 59 (2010), incorporated by reference herein in its entirety. The *Lactobacillus* genus is extremely diverse and expanding every year. With over 230 species, it has grown into one of the biggest genera in the bacterial taxonomy. As the genus has exceeded the acceptable, "normal diversity," renaming and re-classification is inevitable wherein the genus *Lactobacillus* may be split into most likely twelve new genera. Many traditional "probiotic" species with substantiated industrial importance and starter cultures may no longer eventually be called "*Lactobacillus*." Hence, a substantial communication challenge looms ahead with respect to nomenclature. Once the International Committee on Systematics of Prokaryotes publishes new nomenclature in their official journal, the INTERNATIONAL JOURNAL OF SYSTEMATIC AND EVOLUTIONARY MICROBIOLOGY, the changes are valid and official. The manuscript that will be submitted for publication outlining the new nomenclature of the *Lactobacillus* genus will likely be ready for submission by the end of 2018. Meanwhile, there was a taxonomic subcommittee meeting in September 2018 to discuss the nomenclature changes and an (invite-only) expert LABIP workshop in October 2018 that will evaluate the science while considering the consequences for regulations, legal/IP, and industry.

*Bacillus subtilis* has been used abundantly in traditional ethnic food processing, for example, in East Asia. Natto, in particular, is a cheese-like food, processed by inoculating soaked and steamed soybeans with live *Bacillus* from rice straw. *Bacillus subtilis* is the main component in the alkaline fermentation of soybeans without salt. Protease and amylase produced by the bacteria decompose protein and insoluble sugar in the raw soybeans, thus increasing the nutritional value as well as the availability of the soybean foods. See, e.g., K. H. Steinkraus, *Fermentations in world food processing*, 1 COMPREHENSIVE REVIEWS IN FOOD SCI. & FOOD SAFETY 23 (2000), incorporated by reference herein in its entirety. Fermentation not only enriches the nutrients but also enhances the health-promoting effectiveness of soybeans. Compared with nonfermented soybeans, fermented soybeans contain significantly more isoflavone genestein, a chemopreventive agent against cancer. See, e.g., F. Fukutake, et al., *Quantification of genistein and genistin in soybeans and soybean products*, 34 FOOD & CHEMICAL TOXICOLOGY 457 (1996); M. J. Messina, et al., *Soy intake and cancer risk: a review of the in vitro and in vivo data*, 21 NUTRITION & CANCER 113 (1994); each of which is incorporated by reference herein in its entirety. Gamma-polyglutamic acid ("PGA") is the main component of the sticky, mucilagenous material in Japanese fermented soybeans (natto) and increases soluble calcium in the small intestine and thereby increases the efficacy of calcium absorption. See, e.g., H. Tanimoto, et al., *Natto mucilage containing poly-gamma-glutamic acid increases soluble calcium in the rat small intestine*, 65 BIOSCIENCE, BIOTECHNOLOGY, & BIOCHEMISTRY 516 (2001), incorporated by reference herein in its entirety. PGA also acts as dietary fiber to reduce the cholesterol level in serum. See, e.g., K. Tsuji & E. Tsuji, *Effect of Natto-feeding on cholesterol level of rats*, 44 JAPAN J. NUTRITION & DIETETICS 41 (1986), incorporated by reference herein in its entirety. Natto extract exhibits antioxidative activity, anti-tumor activity, and angiotensin-I converting enzyme inhibitory activity. See, e.g., H. Esaki, et al., *Antioxidative activity of Natto*, 37 J. JAPANESE SOC'Y FOR FOOD SCI. & TECH. 474 (1990); C. Takahashi, et al., *Possible anti-tumor-promoting activity of components in Japanese soybean fermented food, Natto: effect on gap functional intercellular communication*, 16 CARCINOGENESIS 471 (1995); A. Okamoto, et al., *Angiotensin I converting enzyme inhibitory activity of various fermented foods*, 59 BIOSCIENCE, BIOTECHNOLOGY, & BIOCHEMISTRY 1147 (1995); each of which is incorporated by reference herein in its entirety. Certain strains of *Bacillus subtilis* isolated from natto produce subtilisin NAT (formerly designated BSP, or nattokinase), which exhibits strong fibrinolytic activity. See, e.g., H. Sumi, et al., *Enhancement of the fibrinolytic activity in plasma by oral administration of natto kinase*, 84 ACTA HAEMATOLOGICA 139 (1990); M. Fujita, et al., *Thrombolytic effect of nattokinase on a chemically induced thrombosis model in rat*, 18 BIOLOGICAL & PHARM. BULLETIN 1387 (1995); each of which is incorporated by reference herein in its entirety. Subtilisin NAT-producing *Bacillus* strains have been isolated not only from natto but also from fermented soybean foods from Korea, Taiwan, and China. Dietary supplementation with natto suppresses intimal thickening and modulates the lysis of mural thrombi. See, e.g., Y. Suzuki, et al., *Dietary supplementation with fermented soybeans suppresses intimal thickening*, 19 NUTRITION 261 (2003); Y. Suzuki, et al., *Dietary supplementation of fermented soybean, natto, suppresses intimal ticking and modulates the lysis of mural thrombi after endothelial injury in rat femoral artery*, 73 LIFE SCIS. 1289 (2003); each of which is incorporated by reference herein in its entirety. Both the decrease in thrombus count and plasma euglobulin and the increase in tissue plasminogen activator are caused by oral intake of *Bacillus subtilis* BN-1 strain. See, e.g., H. Sumi, et al., *Natto Bacillus as an oral fibrinolytic agent: nattokinase activity and the ingestion effect of Bacillus subtilis natto*, 10 FOOD SCI. & TECH. RES. 17 (2004), incorporated by reference herein in its entirety. However, those two effects might partially be due to subtilisin Nat, although the mechanism for the enzyme to potentiate fibrinolysis in vivo is not yet fully understood. See, e.g., T. Urano, et al., *The profibrolytic enzyme subtilisin NAT purified from Bacillus subtilis claves and inactivates plasminogen activator inhibitor type 1*, 276 J. BIOLOGICAL CHEMISTRY 24690 (2001), incorporated by reference herein in its entirety. "Thua nao" is a traditional fermented soybean food produced in northern Thailand. See, e.g., A. Leejeerajumnean, et al., *Volatile compounds in Bacillus fermented soybean*, 81 J. SCI. FOOD & AGRICULTURE 525 (2001), incorporated by reference herein in its entirety. Typically, Thua nao is produced by first boiling and mashing soybeans, and then fermenting the soybeans in banana leaves for 2-3 days at ambient temperature. Alternatively, boiled, mashed soybeans are dried outdoors in the sun. Sun-dried Thua nao can be stored for several months at room temperature. See e.g., P. Chantawannakul, et al., *Characterization of protease of Bacillus subtilis strain 38 isolated from traditionally fermented soybean in Northern Thailand*, 28 SCI. ASIA 241 (2002), incorporated by reference herein in its entirety. Similar sun-dried fermented soybean foods are also produced in Nepal, in Yunnan province of China, and in northern Laos and Myanmar. See, e.g., Y. Inatsu, et al., *Characterization of Bacillus subtilis strains isolated from fermented soybean foods in southeast Asia: comparison with B. subtilis (natto) starter strains*, 36 JAPAN AGRICULTURAL RES. QUARTERLY 525 (2001), incorporated by reference herein in its entirety. Thua nao and other naturally fermented soybean foods are thought to harbor *Bacillus subtilis* strains, which exhibit high potential for producing enzymes such as amylase and protease, and for producing health-promoting compounds such as PGA and protease NAT. Thua nao has been demonstrated to possess a diversity of *Bacillus subtilis*. See, e.g., Y. Inatsu, et al., *Characterization of Bacillus subtilis strains in Thua nao, a traditional fermented soybean food in northern Thailand*, 43 LETTERS IN APPLIED MICROBIOLOGY 237 (2006), incorporated by reference herein in its entirety. Although the cultural history of *Bacillus subtilis* fermentation is well known, research on modern uses and consumption of *Bacillus subtilis* is comparatively very recent. Clinical trials have shown that *Bacillus subtilis* is safe for consumption, and beneficial for digestive health. *Bacillus subtilis* displays immunostimulating properties and antagonizes gastrointestinal pathogen infection by producing antimicrobial substances such as amicoumacins. See, e.g., Marie Lefevre, et al., *Probiotic strain Bacillus subtilis CU1 stimulates immune system of elderly during common infectious disease period: a randomized, double-blind placebo-controlled study*, 12 IMMUNITY & AGEING 24 (2015), incorporated by reference herein in its entirety.

The term "probiotic" means "for life" in Greek. It was first used in 1965 to name microorganisms that are beneficial to consume. The general health benefits of consuming probiotics have been shown in both animal and human studies. As a component of the human microbiome, *Bacillus subtilis* has the ability to promote gastrointestinal health, including helping its host in digestion, making it an ideal probiotic. The term "probiotic," as used herein, can refer to viable microorganisms that promote or support a beneficial balance of the autochthonous microbial population of the gut. Alternatively, probiotics can refer to "live microorganisms that may confer a health benefit on the host." These bacterial strains are becoming extremely popular, not only in alternative circles and in holistic medicine, but also within the scientific community. Scientists have discovered that the microbes that live within animal intestines are important to their health. Animal and human species can host at least 1000 different species of bacteria and fungi, and maintaining and managing the right populations of each species is essential. Therefore, maintaining intestinal flora with probiotics is a logical step. The notion of probiotics evolved from a theory first proposed by Elie Matchnikoff (Nobel laureate), who associated longevity with the consumption of fermented milk products. He postulated that the *Bacillus* present could positively modify the bacterial community structure of the colon, thus contributing to human health status. While not intending to be bound by any theory, the present disclosure is in general agreement with the current understanding of probiotics as used in foods and nutritional/dietary supplements for animals and humans. The microbial population of the intestine is a highly dynamic and complex ecosystem having an estimated $10^{14}$ microorganisms representing more than 400 bacterial species. It has many functions in humans, including providing enzymes necessary for assimilation and/or synthesis of some nutrients, as well as in detoxifying certain harmful dietary compounds. In addition, the gastrointestinal flora provides a natural barrier against pathogens and can stimulate bowel motility and the immune system. Probiotic formulations and blends should be able to recover and compete with established microflora in the colon to provide colonization and benefits for the host. For this purpose, they can use help from prebiotics such as inulin. The gut microbiome influences myriad host functions, including nutrient acquisition, immune modulation, brain development, and behavior. Although human gut microbiota are recognized to change as we age, information regarding the structure and function of the gut microbiome during childhood is limited. A study using 16S rRNA gene and shotgun metagenomics sequencing characterized the structure, function, and variation of the healthy pediatric gut microbiome in a cohort of school-aged, pre-adolescent children (ages 7-12 years). The results showed a difference in the microbiome of the children vs. adults on many strains of bacteria. Children were enriched in *Bifidobacterium* spp., *Faecalibacterium* spp., and members of the Lachnospiraceae, while adults harbored greater abundances of *Bacteroides* spp. From a functional perspective, significant differences were detected with respect to the relative abundances of genes involved in vitamin synthesis, amino acid degradation, oxidative phosphorylation, and triggering mucosal inflammation. Children's gut communities were enriched in functions which may support ongoing development, while adult communities were enriched in functions associated with inflammation, obesity, and increased risk of adiposity. See, e.g., Hollister, et al., *Structure and function of the healthy pre-adolescent pediatric gut microbiome*, 3 MICROBIOME 36 (2016), incorporated by reference herein in its entirety. Recently, probiotics therapy, evidenced by numerous randomized clinical trials ("RCTs") followed by meta analyses and Cochran reviews, has generated a great deal of renewed interest due to its significant therapeutic effect on rotavirus-associated diarrhea in children in developed countries. The most commonly used strains of probiotics belong to the genera *Lactobacillus* and *Bifidobacterium, L. rhamnosus* GG, *Saccharomyces boulardii, Bacillus clausii*, mix of *L. delbrueckii* var *bulgaricus, Streptococcus thermophiles, L. acidophilus*, and *Bifidobacterium bifidum*, or *Enterococcus faecium* SF 68. The median duration of diarrhea was significantly shorter and the frequency was lower only in those children who received mixes of four bacterial strains. See, e.g., Dutta, et al., *Randomised controlled clinical trial of Lactobacillus sporogenes (Bacillus coagulans), used as a probiotic in clinical practice, on acute watery diarrhea in children*, 16 TROPICAL MED. INT'L HEALTH 555 (2011), incorporated by reference herein in its entirety. Furthermore, the issue of the safe application of probiotics is not new or specific to older populations; however, there are aspects that are particular to this age group and that need to be addressed. As has been reviewed of late, the safety of application/consumption of a probiotic is linked to the potential vulnerability of the consumer to specific disease states. See, e.g., Rijkers, et al., *Guidance for substantiating the evidence for beneficial effects of probiotics: current status and recommendations for future research*, 140 J. NUTRITION 671S (2010), incorporated by reference herein in its entirety. Older people are by definition more likely to present "at-risk" factors, which include immune compromise, central venous catheter, impaired intestinal barrier function, or consumption of broad-spectrum antibiotics to which the probiotic is resistant. See, e.g., Boyle, et al., *Probiotic use in clinical practice: what are the risks?*, 83 J. AM. CLINICAL NUTRITION 1256 (2006), incorporated by reference herein in its entirety. Probiotics have been consumed safely for a long time by the general population, exemplified by the incidence of only one case of *lactobacillus* septicemia among 10 million consumers in France over the course of a century. See, e.g., Bernardeau, et al., *Beneficial lactobacilli in food and feed: long-term use, biodiversity and proposals for specific and realistic safety assessments*, 30 FEMS MICROBIOLOGY REVS. 487 (2006), incorporated by reference herein in its entirety.

Nevertheless, the suitability of therapeutic application of probiotics in older subjects, as distinct from consumption of foods containing probiotic bacteria, should be considered individually and focus on specific needs. Compared with younger adults, populations of older adults consume a complex array of medications, ranging from antibiotics through to pharmaceutical compounds with potential but unknown effects upon the complex bacterial community in the intestine. For example, in the first 360 subjects enrolled in the ELDERMET project, 95 subjects had consumed antibiotics in the 4 weeks prior to their baseline microbiota determination, and 98% had consumed a recognized medicinal compound. See, e.g., Rijkes, et al., 2010. Probiotics have recognized utility to mitigate the diarrheal side effects of antibiotics and to reduce the incidence of *Clostridum difficile*-associated colitis. See, e.g., Hickson, et al., *Use of probiotic Lactobacillus preparation to prevent diarrhea associated with antibiotics: randomized double blind placebo controlled trial*, 355 BMJ 80 (2007); C. M. Surawicz, et al., *Role of probiotics in antibiotic-associated diarrhea, Clostridium difficile-associated diarrhea, and recurrent Clostridium difficile*-associated diarrhea, 42 (Suppl. 2) J. CLINICAL GASTROENTEROLOGY S64 (2008); each of which is incorporated by reference herein in its entirety. Lifting the burden of infectious disease would be particularly beneficial in older populations.

Several recent comprehensive reviews have summarized the major benefits associated with probiotic consumption in older adults, and such benefits include increased levels of bifidobacteria, reduced constipation, enhanced innate immunity, and reduced inflammation. See, e.g., Pitkala, et al., *Fermented cereal with specific bifidobacteria normalizes bowel movements in elderly nursing home residents. A randomized, controlled trial*, 11 J. NUTRITION, HEALTH, & AGING 305 (2007); Gill, et al., *Enhancement of immunity in the elderly by dietary supplementation with the probiotic Bifidobacterium lactis HN019*, 74 AM. J. CLINICAL NUTRITION 833 (2001); Ouwehand, et al., *Bifidobacterium microbiota and parameters of immune function in elderly subjects*, 53 FEMS IMMUNOLOGY & MEDICAL MICROBIOLOGY 18 (2008); each of which is incorporated by reference herein in its entirety. Administration of yoghurt fermented by *L. bulgaricus* to older people (n=142; a median age of 74.5 years) significantly reduced the incidence and severity of winter colds and general upper respiratory symptoms. This improvement was accompanied by an increase in natural killer cell activity in the subjects receiving the yoghurt. See, e.g., Makino, et al., *Reducing the risk of infection in the elderly by dietary intake of yoghurt fermented with Lactobacillus delbrueckii ssp. Bulgaricus OLL1073R-1*, 104 BR. J. NUTRITION 998 (2010), incorporated by reference herein in its entirety.

Preclinical validation of beneficial effects in in vitro systems or animal models may thus be beneficial for strain selection, but obviously cannot replace human trials. Older adults as a group in society will typically span a greater range in health status (from healthy and independent to frail and dependent upon assistance). Older adults are known to have microbiota in flux that varies significantly more between individuals than in a younger adult population. These factors should be borne in mind when designing clinical trials.

Recent analyses of the microbiota of older adults in Ireland confirmed that the prevalence of the genus *Faecalibacterium* varied significantly between individuals, supporting the notion that levels of this organism might be suitable for therapeutic intervention in older people with intestinal inflammation. Administration of prebiotics, or by administering probiotics that target competing elements in the microbiota, is conceptual at this time. See, e.g., S. Cusack, et al., *How Beneficial is the Use of Probiotic Supplements for the Aging Gut?*, 7 AGING HEALTH 179 (2011), incorporated by reference herein in its entirety.

Furthermore, domesticated animals and/or pet animals can benefit from probiotics. Pet animals may include small or large domestic mammals, for example, but are not limited to, dogs, cats, horses, sheep, cows, cattle, other bovine species, pigs, goats, rabbits, and the like. Also contemplated are small rodent species, including rats, mice, hamsters, gerbils, guinea pigs, and the like.

All dogs can benefit from probiotics, which aid digestion and modulate the immune system. Probiotics produce short-chain fatty acids ("SCFAs"), which inhibit the growth and activity of harmful bacteria, such as *E. coli, Salmonella*, and *Clostridium perfringens*, as well as provide other benefits to the intestines. Human studies have documented the effectiveness of certain strains in treating diarrhea, irritable bowel syndrome, and intestinal inflammation. Probiotics used in dogs may help prevent urinary tract infections, and can even reduce allergic reactions by decreasing intestinal permeability and controlling inflammation.

Research looking at the effectiveness of probiotics in dogs is not early as extensive as research of the effectiveness in humans. Still, there are studies that suggest that probiotics can improve or maintain the health of dogs. The diseases that have been investigated so far to determine the effectiveness of probiotics in dogs are acute diarrhea and contact dermatitis (skin allergy).

Acute diarrhea in dogs is diarrhea that starts suddenly and usually resolves on its own. Probiotics have been tested on several types of acute diarrhea, specifically diarrhea caused by dietary sensitivity and diarrhea caused by the ingestion of an intestinal pathogen. In dogs with dietary sensitivity, treatment with *Lactobacillus acidophilus* in combination with the diarrhea-provoking food led to some improvement in bowel movements. Better results, however, were observed when probiotics were applied as treatments for acute diarrhea caused by a stomach virus.

Probiotic species known to benefit dogs include *Bacillus coagulans*. *Bifidobacterium animalis* has been shown to reduce the time for acute diarrhea to resolve in dogs. *Lactobacillus acidophilus* improved frequency and quality of stools in sensitive dogs. *Lactobacillus rhamnosus* strain GG ("LGG") is effective in preventing and treating diarrhea in humans, and may benefit dogs as well.

*Bifidobacterium animalis* has been studied more in detail. *Bifidobacterium animalis* was chosen for further research because initial studies showed that *Bifidobacterium animalis* had an above-average ability to bind to the gut, a characteristic often associated with beneficial bacteria. Initial studies in dogs showed that *Bifidobacterium animalis* could reduce the pathogenicity of *Salmonella typhiurium* and Clostridia *difficile*, which are bacteria known to induce acute diarrhea. And later, during a treatment study, it was found that *Bifidobacterium animalis* could help acute diarrhea resolve faster.

Dermatitis is usually caused by a skin allergy. To treat the dermatitis, one needs to address the underlying immune problems. During allergic responses, the immune system considers a normally harmless substance as a threat. In dogs with a skin allergy, contact of the allergen on the skin causes an immune reaction leading to the classic symptoms of inflammation: itching, redness, and heat. Unfortunately, dogs that develop allergies are usually genetically predisposed to the condition. This means that prevention has to happen at a young age or even when a puppy is still in the womb.

Scientists looked at the ability of *L. rhamnosus* to change the course of allergy in dogs with a genetic predisposition towards allergy. *L. rhamnosus* was given during pregnancy to the mother and to the puppies during weaning. Unfortunately, while there were some significant changes in immunological parameters, the puppies had no real improvements, but a follow-up study performed three years later in the grownup puppies showed that there were differences in the long-term. The immune system was geared towards anti-inflammatory reactions, and the dogs had less dermatitis.

Additionally, many products on the market are of dubious quality. A study testing 19 commercial pet foods, all claiming to contain probiotics, determined that none of the feeds contained what was written on the packages. Only 53% of the tested commercial pet foods contained at least one of the probiotics species listed, and 26% of the tested commercial pet foods had no live bacteria. These results would suggested that using pet food fortified with probiotics is not the wisest route for providing one's pet dog with beneficial bacteria. The recommendation would be to seek out a quality probiotic with the help of a veterinarian.

Probiotics are measured by colony forming units ("CFUs"), e.g., CFU/g or CFU/mL. Few studies have been done to determine effective dosages, but effective dosages are usually in the hundreds of millions of CFUs or higher. If probiotics are being used to help with digestion, probiotics should be taken with meals, but otherwise the probiotics may survive better if taken between meals, particularly if taken with liquids that help to dilute stomach acid and move the probiotics more quickly into the digestive tract (for example, given after the dog takes a big drink). Probiotics may be given short-term or long-term.

Several studies have revealed that some probiotics products in the market have deficiencies in the viabilities of probiotic strain(s), especially in products containing Bifidobacteria. These deficiencies in viability may be due to storage, manufacturing, or food technology setbacks, such as inappropriate packing materials that could affect probiotic stability through variations in oxygen permeability. In the past two decades, there has been renewed interest in the study of the nutritional and therapeutic aspects of the mentioned products. It is widely accepted that probiotics may exert positive influence on the host through modulation of the endogenous ecosystem and stimulation of the immune system, as well as maintenance of healthy intestinal microflora. However, research suggests that health benefits can be strain-specific and vary by amount ingested and duration administered, even in pets.

One useful *Bacillus subtilis*-containing composition is DE111® ("DE111"), available from Deerland Enzymes, Inc. (Kennesaw, Ga., United States). DE111 may include *B. subtilis* having an Accession no. NRRL B-67989 as deposited with the Agricultural Research Service Culture Collection (NRRL), an International Depositary Authority, 1815 N. University Street, Peoria, Ill., 61604, United States) under the Budapest Treaty on the International Recognition of the Deposit of Microorganisms, on Sep. 28, 2020 and accepted and found to be viable on Sep. 28, 2020, an isolated strain of *B. subtilis* subsp. *inaquosorum*.

Using in vitro assays, characterization and utilization of the antifungal and antibacterial properties of *Bacillus subtilis* DE111 is possible. Various *Bacillus subtilis* species synthesize major classes of antifungals, i.e., CLPs. The production of strong antifungal activity in vitro was observed using genome sequencing. Additionally, the production of bacillomycin F and fengycin was observed. See, infra, Example 1. These antifungals are strong inhibitor of fungal species including, but not limited to, *Alternaria alternate*, *Aspergillus niger*, *Cladosporium* spp., *Fusarium* spp., *Geotrichium candidum*, *Rhodotorula* spp., *Sordoaria fimicola*, *Trichoderma* spp., and *Zygorhynchus* spp. Experiments also showed that *Bacillus subtilis* DE111 contains four antibacterial clusters that include bacilysin, subtilosin, aurantinin, and sublancin, which are able to inhibit certain bacterial populations such as *Escherichia coli*, and yeast species including *candida*.

Using various laboratory methodologies, including whole genome sequencing, HPLC/LC-MS, and modified Kirby-Bauer tests, *Bacillus subtilis* DE111 was shown to produce potent antifungals as well as antibacterial substances. Antifungals produced included bacillomycin F and fengycin, and are efficacious against a wide range of fungal pathogens. Bacillomycin F and fengycin are also known as inhibitors of phospholipase A2, a key enzyme in inflammation response in humans. Furthermore, bacillomycin F is part of an iturin group of antibiotics. In addition to its potent antifungal properties, it has a narrow spectrum against bacteria. Fengycin inhibits filamentous fungi. Fengycin consists of two main components differing by one amino acid exchange. See, e.g., N. Vanittanokom, et al., *Fengycine—a novel antifungal lipopeptide antibiotic produced by Bacillus subtilis*: F-29-3, 39 J. ANTIBIOTICS 888 (1986), incorporated by reference herein in its entirety. Additionally, surfactins, bacillibactin, bacilysin, subtilosin, and sublancin were also observed. Surfactin has multiple functions as a powerful antibiotic. A CLP, surfactin's amphiphilic properties help surfactin to survive in both hydrophilic and hydrophobic environments. Bacilysin is a non-ribosomically produced dipeptide-based antibacterial with activity against a wide range of bacteria and some yeasts. Subtilosin belongs to the class of antibacterial compounds known as bacteriocins, which are the most common classes of antibacterials reported. Bacteriocins are thought to play an important role in microbial communities that overlap ecological niches, based in part on bacteriocins often having activity against closely related members of the population that would likely occupy the same ecological niche. Sublancin was further identified as a class of bacterials known as glycocins that are ribosomally produced.

Without being bound by theory, it is thought that these results are important, given that fungi including, but not limited to, *Alternaria alternate, Aspergillus niger, Cladosporium* spp., *Fusarium* spp., *Geotrichium candidum, Rhodotorula* spp., *Sordaria fimicola, Trichoderma* spp., and *Zygorhynchus* spp., are natural plant pathogens, and bacterial strains such as *Escherichia coli* can cause disease. However, control of such fungal and bacterial pathogens may be achieved by using *Bacillus subtilis* DE111 with probiotic properties.

The *Bacillus subtilis* DE111 strain has certain properties, which, surprisingly, have been found to make the strain well-suited for use as a probiotic. Spores of *Bacillus subtilis* are viable under a wide temperature and pH range. Without being bound by any particular theory, it is thought that the ability of *Bacillus subtilis* DE111 to form spores that protect the microbes from harsh conditions until they enter an environment ripe for germination, such as the GI tract, makes *Bacillus* particularly well-suited for use as a probiotic.

In some embodiments, the compounds and compositions of the present invention are useful in the treatment of a wide range of diseases and conditions. In certain embodiments, the compounds and compositions of the present invention are useful in the treatment and prevention of infections, including, but not limited to, bacterial, fungal, and yeast infections. In further embodiments, the compounds and compositions of the present inventions are useful in the treatment or prevention of infections including, but not limited to, *Candida* spp. infections, *Escherichia coli* infections, *Alternaria alternate* infections, *Aspergillus niger* infections, *Caldosporium* spp. infections, *Fusarium* spp. infections, *Geotrichum candidum* infections, *Rhodotorula* spp. infections, *Sordaria fimicola* infections, *Trichoderma* spp. infections, and *Zygorhynchus* spp. infections.

In embodiments of the present invention, the present invention relates to the prevention or treatment of fungal, bacterial, and yeast infections. In certain embodiments, the probiotic compositions of the present invention exhibit anti-infection (anti-infective) activity, including, but not limited to, anti-adhesion activity, or preventing the adhesion of bacteria, yeast, or fungus to cells. Thus, in certain embodiments, the compositions of the present invention are useful for the prevention or treatment of infections including, but not limited to, bacterial infections, multi-drug resistant bacterial infections, hospital-acquired bacterial functions, antibiotic-resistant bacterial infections, and gram-negative and/or gram-positive bacterial infections. In other embodiments, the compositions of the present invention are useful in the prevention of infections by species, including, but not limited to, *Candida* spp., *Escherichia coli, Alternaria alternate, Aspergillus niger, Caldosporium* spp., *Fusarium* spp., *Geotrichium candidum, Rhodotorula* spp., *Sordaria fimicola*, and the like.

Without being bound by theory, infections occur where disease-causing microorganisms invade the tissues of the body. Multiplication of such microorganisms and the toxins that they produce react with the tissues of the body, often causing immune reactions by the infected host. Infections may be caused by bacteria, viruses, fungi, and other parasites. Infections may occur via any of the tissues of the body, such as the skin, gut, alimentary canal, GI tract, or membranes. In certain embodiments, the probiotic compounds and compositions of the present invention, including, but not limited to, probiotic bacteria or lysates, can be used to treat infection of tissues other than the gut. In other embodiments, the probiotic compounds and compositions of the present invention, including, but not limited to, probiotic bacteria or lysates, can be used to treat, remove, or prevent infection of the external surface of the body, and particularly the skin. In yet other embodiments, the probiotic compounds and compositions of the present invention, including, but not limited to, probiotic bacteria or lysates, can be used in the prevention, removal, or treatment of skin infections. In certain embodiments of the present invention, infections that can be prevented, removed, or treated are infections due to bacteria, yeast, or fungi. In certain embodiments of the present invention, the probiotic compounds and compositions of the present invention can be applied separately, sequentially, or simultaneously with exposure to the infective agent. Preferably, probiotic compounds and compositions of the present invention are applied before exposure to the infective agent.

In certain embodiments of the present invention, probiotic compounds and compositions of the present invention are preferably used for the prevention of bacterial infection. In some embodiments, the probiotic compounds and compositions of the present invention are preferably administered to a subject before said subject is exposed to the infective agent. In certain embodiments, a subject to whom the probiotic compounds and compositions of the present invention can be administered may have been identified as being at risk of infection by the infective agent. A subject may be identified as being at risk of infection by an infective agent because of the environment of the subject, including, but not limited to, being situated in an environment in which the infective agent is known to exist, and/or due to the health of the subject, including, but not limited, due to the existence of an open wound, or poor immune health. In certain embodiments, the probiotic compounds and compositions of the present invention may be used in hospitals or other clinical environments in which pathogenic bacteria are known to, or suspected to, be present.

In some embodiments, a subject to whom the probiotic compounds and compositions of the present invention can be administered is about to undergo, or has recently undergone, surgery. In certain embodiments of the present invention, probiotic compounds and compositions of the present invention can be used to prevent infection of an open wound, such as a surgical incision or graft, by a pathogenic bacterium. In embodiments of the present invention, probiotic compounds and compositions of the present invention may be administered alone or in combination with other treatments, either simultaneously or sequentially, depending upon the medical condition to be treated.

In embodiments of the present invention, antibacterial and/or antifungal compositions of the present invention can be in the form of cleaning products, washes, surface coatings, or other compositions that are not suitable for medical treatment of a subjection. In certain embodiments, antibacterial and/or antifungal compositions of the present invention in the form of cleaning products, washes, surface coatings, or other compositions may be useful for removing, treating, or preventing the accumulation of bacteria, fungus, and/or yeast on a surface, or for inhibiting the action or growth of the bacteria, fungus, and/or yeast. In other embodiments, antibacterial and/or antifungal compositions of the present invention are formulated from secreted materials.

In embodiments of the present invention, antibacterial and/or antifungal compositions of the present invention can be used to treat surfaces prone to colonization or exposure to bacteria, yeast, or fungi, including, but not limited to, handrails, food preparation surfaces, kitchen surfaces or equipment, tables, sinks, toilets, or other bathroom hardware.

In embodiments of the present invention, antibacterial and/or antifungal compositions of the present invention may comprise agents in addition to the probiotic compounds and lysates of the present invention, including, but not limited to, cleaning agents, stabilizers, anionic surfactants, perfumes, chelating agents, acids, alkalis, buffers, or detergents. Such agents may facilitate or enhance the antibacterial and/or antifungal properties of the probiotic compounds and lysates of the present invention, including, but not limited to, killing or inhibiting bacteria, fungi, and/or yeast, or preventing the recolonization of a cleaned surface.

In further embodiments of the present invention, methods of preparing a surface may include applying secreted material and/or probiotic compounds of the present invention to the surface. In certain embodiments of the present invention, the methods may result in reduced colonization of the surface by pathogenic microorganisms.

In one aspect of the invention, compositions administered to patients in need thereof according to the methods of the present disclosure comprise mutants of *Bacillus subtilis* DE111 having all the identifying characteristics of *Bacillus subtilis* DE111. Such mutants may have DNA sequence identity to *Bacillus subtilis* DE111 of at least about 90%, at least about 91%, at least about 92%, at least about 93%, at least about 94%, at least about 95%, at least about 96%, at least about 97%, at least about 98%, or at least about 99%. In some embodiments, mutants are spontaneous mutants. The term "spontaneous mutant" refers to mutants that arise from *Bacillus subtilis* DE111 without the intentional use of mutagens. Such spontaneous mutants may be obtained by classical methods, such as growing the *Bacillus subtilis* DE111 strain in the presence of a certain antibiotic to which the parent is susceptible, and testing any resistant mutants for improved biological activity or, in this application, ability to improve the body composition of an individual. Other methods for identifying spontaneous mutants will be known to those of ordinary skill in the art.

All references in this application to *Bacillus subtilis* DE111 or its mutants refer to bacteria that have been isolated from nature and are grown by humans, for example, in the laboratory or under industrial conditions.

*Bacillus subtilis* DE111 cells may be present in the compositions administered to patients in need thereof according to the methods of the present disclosure as spores (which are dormant), as vegetative cells (which are growing), as transition state cells (which are transitioning from growth phase to sporulation phase) or as a combination of all of these types of cells. In some embodiments, the composition comprises mainly spores. In other embodiments, the composition comprises spores and metabolites produced by the cells during fermentation before they sporulate as described below.

Compositions administered to patients in need thereof according to the methods of the present disclosure can be obtained by culturing *Bacillus subtilis* DE111 or its mutants according to methods well known in the art. Conventional large-scale microbial culture processes include submerged fermentation, solid state fermentation, or liquid surface culture. Towards the end of fermentation, as nutrients are depleted, *Bacillus subtilis* DE111 cells begin the transition from growth phase to sporulation phase, such that the final product of fermentation is largely spores, metabolites, and residual fermentation medium. Sporulation is part of the natural life cycle of *Bacillus subtilis* DE111 and is generally initiated by the cell in response to nutrient limitation. Fermentation is configured to obtain high levels of colony forming units of *Bacillus subtilis* DE111 and to promote sporulation. The bacterial cells, spores, and metabolites in culture media resulting from fermentation may be used directly or concentrated by conventional industrial methods, such as centrifugation, tangential-flow filtration, depth filtration, and evaporation. In some embodiments, the concentrated fermentation broth is washed, for example, via a diafiltration process, to remove residual fermentation broth and metabolites.

The fermentation broth or broth concentrate can be dried with or without the addition of carriers using conventional drying processes or methods such as spray drying, freeze drying, try drying, fluidized-bed drying, drum drying, or evaporation. The resulting dry products may be further processed, such as by milling or granulation, to achieve a specific particle size or physical format. Carriers, described below, may also be added post-drying.

In embodiments in which compositions formulated separately from food or drink are administered to patients in need thereof according to the methods of the present disclosure, the concentration on a weight by weight basis (w/w) of (i) *Bacillus subtilis* DE111 or its mutants, (ii) metabolites of *Bacillus subtilis* DE111 or its mutants, or (iii) combinations of cells and metabolites in the formulated composition may be about 0.5%, about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, or about 95%. In some embodiments of compositions administered to patients in need thereof according to the methods of the present disclosure, where the concentrated formulation broth has been washed and dried without heat, such as via freeze drying, the concentration of *Bacillus subtilis* DE111 or its mutants in the final composition may be from about 90% to about 100%.

Thus, in line with the above, embodiments of the present disclosure are directed to methods of treating, removing, or preventing the accumulation of bacteria, fungus, and/or yeast on a surface, and/or treating or preventing fungal, bacterial, and/or yeast infections in a human subject, by administering to the subject a composition comprising *Bacillus subtilis* DE111, a mutant of *Bacillus subtilis* DE111, metabolites of *Bacillus subtilis* DE111 or its mutants, or combinations of *Bacillus subtilis* DE111 or a mutant and metabolites of *Bacillus subtilis* DE111 or its mutants.

Without wishing to be bound by any particular theory, it is thought that increases to beneficial bacteria may be caused by stimulating growth of such bacteria or simply by selectively decreasing pathogenic bacteria, thereby giving the beneficial bacteria more space to grow and to attach to the gut wall and/or more efficient access to nutrients and growth factors. In addition, or alternatively, beneficial bacteria may modify the virulence factors of pathogenic bacteria, thus decreasing the virulence and/or inhibiting the growth of the pathogenic bacteria. Harmful, disease-causing bacteria that may be decreased or the growth of which may be inhibited by the methods of the present disclosure include Clostridia spp. (such as *perfringens* and *dificille*), *Listeria* spp. (such as *Moncytogenes, seeligeri*, and *welshimeri*), *Salmonella* spp. (such as *enterica, arizonae, typhirium, enteridis*, and *bonglori*), *E. coli*, *Enterococcus* spp. (such as *faecalis* and *faecium*), *Camphylobacter, Aeromonas* spp., *Staphylococcus*

*aureus, Shigella dysenteria,* and *Vibrio* spp. In some embodiments, harmful, disease-causing microorganisms may be reduced by about 0.5 log, about 1 log, about 2 log, about 3 log, about 4 log, or about 5 log.

Without being bound by theory, metabolites of *Bacillus subtilis* DE111 and/or its mutants include one or more agents, secreted material, and/or extracellular products, which are secreted from *Bacillus subtilis* DE111 and/or its mutants which that are present in the culture media of *Bacillus subtilis* DE111 and/or it mutants. The metabolites of *Bacillus subtilis* DE111 and/or its mutants may inhibit the ability of the pathogenic bacteria or pathogenic fungi to infect surrounding host cells. Accordingly, the metabolites of *Bacillus subtilis* DE111 and/or its mutants according to the present disclosure are protective against pathogenic bacteria and/or fungi.

Without being bound by theory, secreted material includes matter secreted from *Bacillus subtilis* DE111 and/or its mutants and can be shown to exhibit antibacterial and/or antifungal properties that can be harnessed in a variety of compositions. The term "secreted material," as used herein, alone or in combination with other terms, unless otherwise stated, means material secreted from a probiotic bacterium. The secreted material may include a single agent or a mixture of two or more agents. The secreted material may include, but is not limited to: proteins; carbohydrates; nucleic acids; or lipids; or the secretome, which refers to all of the secreted proteins and secretory machinery of the probiotic bacterium, and may additionally encompass molecules that are not proteins, such as carbohydrates, lipids, and/or nucleic acids.

In certain embodiments of the present disclosure, compositions are described to contain secreted material "in a carrier." Without limitation, the term "carrier" can refer to a solution in which secreted material is dissolved, suspended, diluted, or admixed. In particular embodiments, the carrier may be the medium that has been in contact with the probiotic bacterium during culturing. Without being bound by theory, a medium may have changed during culturing of the probiotic bacteria, for example, by the secretion of material from the probiotic bacterium. The compositions according to embodiments of the present disclosure may include culture media in which *Bacillus subtilis* DE111 has been cultured. Media suitable for culturing probiotic bacteria are well known to those of skill in the art.

As used herein, the terms "media" and "medium," alone or in combination with other terms, unless stated otherwise, refer to and encompass any nutrient-containing liquid in which microorganisms including bacteria may be supported, kept alive, grown, and/or expanded. Media may contain the minimal nutrients to support bacterial life, and optionally other nutrients. Exemplary nutrients contained within media broth include, but are not limited to, sugar, magnesium, phosphate, phosphorous, and calcium. Media may be made to, or modified from, a combination of nutrients that is well known in the art. Media may be obtained pre-mixed from a commercial source, or may be made in-house. The probiotic bacteria according to embodiments of the present invention may have been in contact with the media for at least about 6 hours, at least about 12 hours, at least about 18 hours, at least about 24 hours, at least about 2 days, at least about 3 days, at least about 4 days, at least about 5 days, at least about 6 days, at least about 7 days, at least about 8 days, at least about 9 days, at least about 10 days, at least about two weeks, or for more than about two weeks.

The probiotic bacteria according to embodiments of the present invention may have been cultured in the media, or in contact with the media, under aerobic or anaerobic conditions. Preferably, the probiotic bacteria have been cultured under aerobic conditions.

The probiotic bacteria according to embodiments of the present invention may have been cultured in the media under conditions that facilitate growth and expansion of the probiotic bacteria. Such conditions are well known to those of skill in the art. For example, the culture may be incubated at 37° C.

In embodiments of the present invention, a composition may be sterile. As used herein, the term "sterile," alone or in combination with other terms, unless stated otherwise, refers to secreted material that has been subject to a sterilization process, such as heat, pressure, or filtration, or any combination thereof. Such sterilization processes may include, but are not limited to, autoclaving, or UV-light sterilizing. In the case of media containing secreted material, the media may have been sterilized before the probiotic bacteria were introduced and cultured, and/or after the probiotic bacteria has been removed from that media.

In certain embodiments, compositions including secreted material contains substantially no intact probiotic bacteria. In other embodiments, compositions may also be substantially free from lysed bacteria or bacterial fragments, such as bacteria that have undergone apoptosis. The intact probiotic bacteria, lysed bacteria, and/or bacterial fragments may have been separated from the secreted material. Separation may occur by any suitable means known in the art, including, but not limited to, centrifugation and/or filatration. As used herein, the term "substantially free from," alone or in combination with other terms, unless stated otherwise, means that the secreted material contains no or minimal contamination of non-secreted bacterial components, such as intact probiotic bacteria, lysed bacteria, or bacterial fragments. Accordingly, compositions may contain 100% secreted material, at least about 99% secreted material, at least about 95% secreted material, at least about 90% secreted material, at least about 85% secreted material, at least about 80% secreted material, at least about 75% secreted material, or at least about 70% secreted material. Secreted material may include additional components of non-bacterial origin, including carrier solutions, other active agents, and/or preservatives, as described herein.

Compositions according to embodiments of the present invention may be prepared by culturing a probiotic bacteria in media, separating the probiotic bacteria from the media, and preparing a composition from the media. The probiotic bacteria may be cultured under aerobic conditions. The probiotic bacteria may be cultured at a temperature above the normal temperature of the human body. The probiotic bacteria may be cultured at about 30° C., about 31° C., about 32° C., about 33° C., about 34° C., about 35° C., about 36° C., about 37° C., about 38° C., about 39° C., about 40° C., about 41° C., about 42° C., about 43° C., or about 44° C. Preferably the probiotic bacteria are cultured at about 37° C. The probiotic bacteria may be cultured in the media for about 1 day, about 2 days, or about 3 days. The probiotic bacteria, lysed bacteria, or bacterial fragments may be separated from the media by any suitable means, including centrifugation. The media may be subject to sterilization, before or after the probiotic bacteria are removed. For example, following separation of the media from the intact probiotic bacteria, lysed bacteria, or bacterial fragments, the media may be subject to sterilization. The media may be subject to concentration, such that the proportion of secreted material increases relative to the total volume of media. Concentration may be performed by any method known in the art, such as evaporation. Secreted material may be separated from the media. Any method of separating secreted material from a carrier solution may be used. For example, secreted material may be separated from the media by chromatography, crystallization, distillation, drying, electrophoresis, and/or precipitation. Once isolated from the media, or concentrated in the media, the secreted material may be dissolved or diluted in a carrier, or otherwise formulated into a composition according to embodiments of the present invention.

In another aspect, compositions administered according to methods of the present disclosure comprising *Bacillus subtilis* DE111, its mutants, and/or metabolites of *Bacillus subtilis* DE111 and/or its mutants may further include or be administered with other probiotics, such as other bacterial spore formers. Examples of probiotics are provided in H. A. Hong, et al., *The use of bacterial spore formers as probiotics,* 29 FEMS Microbiology Revs. 813 (2005), incorporated by reference herein in its entirety.

In yet another aspect, compositions administered according to methods of the present disclosure may include or be administered with (either at the same time or at different times) anti-diarrheal agents, anti-gas agents, dietary fibers, antibiotics, such as methotrexate, anti-inflammatory drugs, amino acids, electrolytes, vitamins, and minerals.

In embodiments in which the compositions administered according to methods of the present disclosure comprise *Bacillus subtilis* DE111 or its mutants, the bacteria should be administered in an amount that is effective to treat, remove, or prevent the accumulation of bacteria, fungus, and/or yeast on a surface, and/or treat or prevent fungal, bacterial, and/or yeast infections in a human subject. In embodiments in which the compositions are being administered to treat, remove, or prevent the accumulation of bacteria, fungus, and/or yeast on a surface, and/or treat or prevent fungal, bacterial, and/or yeast infections in a human subject, the compositions should be administered at effective total daily doses of from about $1 \cdot 10^3$ CFU *Bacillus subtilis* DE111 to about $1 \cdot 10^{15}$ CFU *Bacillus subtilis* DE111. In other embodiments in which the compositions are being administered to treat, remove, or prevent the accumulation of bacteria, fungus, and/or yeast on a surface, and/or treat or prevent fungal, bacterial, and/or yeast infections in a human subject, the compositions should be administered at effective total daily doses of from about $1 \cdot 10^4$ CFU *Bacillus subtilis* DE111 to about $1 \cdot 10^{14}$ CFU *Bacillus subtilis* DE111. In yet other embodiments in which the compositions are being administered to treat, remove, or prevent the accumulation of bacteria, fungus, and/or yeast on a surface, and/or treat or prevent fungal, bacterial, and/or yeast infections in a human subject, the compositions should be administered at effective total daily doses of from about $1 \cdot 10^5$ CFU *Bacillus subtilis* DE111 to about $1 \cdot 10^{13}$ CFU *Bacillus subtilis* DE111. In yet other embodiments in which the compositions are being administered to treat, remove, or prevent the accumulation of bacteria, fungus, and/or yeast on a surface, and/or treat or prevent fungal, bacterial, and/or yeast infections in a human subject, the compositions should be administered at effective total daily doses of from about $1 \cdot 10^{13}$ CFU *Bacillus subtilis* DE111 to about $1 \cdot 10^{12}$ CFU *Bacillus subtilis* DE111. In yet other embodiments in which the compositions are being administered to treat, remove, or prevent the accumulation of bacteria, fungus, and/or yeast on a surface, and/or treat or prevent fungal, bacterial, and/or yeast infections in a human subject, the compositions should be administered at effective total daily doses of from about $1 \cdot 10^8$ CFU *Bacillus subtilis* DE111 to about $1 \cdot 10^{11}$ CFU *Bacillus subtilis* DE111. In yet other embodiments, a preferred effective total daily dose range is from about $1 \cdot 10^9$ CFU *Bacillus subtilis* DE111 to about $1 \cdot 10^{10}$ CFU *Bacillus subtilis* DE111. In yet another embodiments, *Bacillus subtilis* DE111 can be provided in an effective total daily dose of about $5 \cdot 10^9$ CFU.

In certain embodiments, the compositions administered according to the methods of the present disclosure may also include one or more excipients, most preferably one or more nutraceutical or pharmaceutical excipients. Compositions containing one or more excipients and incorporating one or more probiotics can be prepared by procedures known in the art. Optionally, compositions can include one or more adjuvants, excipients, carriers, buffers, diluents, and/or other customary pharmaceutical auxiliaries. For example, probiotics can be formulated into tablets, capsules, powders, suspensions, solutions for oral administration, solutions for parenteral administration including intravenous, intradermal, intramuscular, and subcutaneous administration, and solutions for application onto patches for transdermal application with common and conventional barriers, binders, diluents, and excipients.

In certain embodiments, nutraceutical compositions administered according to the methods of the present disclosure may be administered in combination with a pharmaceutically acceptable ingredient. In certain embodiments, the active ingredients in such formulations may comprise from about 1% by weight to about 99% by weight. In other embodiments, the active ingredients in such formulations may comprise from about 0.1% by weight to about 99.9% by weight. "Pharmaceutically acceptable ingredient" means any carrier, diluent, or excipient that is compatible with the other ingredients of the formulation and not deleterious to the user. Useful excipients include, but are not limited to, microcrystalline cellulose, magnesium stearate, calcium stearate, any acceptable sugar (e.g., mannitol, xylitol), and the like, and for cosmetic use, an oil-base is preferred. Pharmaceutically acceptable ingredients are well known to those skilled in the art, and include, but are not limited to, pharmaceutically acceptable carriers, adjuvants, excipients, diluents, fillers, buffers, preservatives, antioxidants, lubricants, stabilizers, solubilizers, surfactants (e.g., wetting agents), masking agents, coloring agents, flavoring agents, and sweeting agents.

Though it is possible for the secreted material of the antibacterial and/or antifungal compositions of the present invention to be used alone, in certain embodiments, it is preferable to present the antibacterial and/or antifungal compositions of the present invention as formulations comprising secreted material and one or more carriers. In embodiments of the present invention, the secreted material of the antibacterial and/or antifungal compositions of the present invention may be dissolved in, suspended in, or admixed with one or more other ingredients. In some embodiments, the secreted material of the antibacterial and/or antifungal compositions of the present invention may be presented in liposomes or other microparticulates. Formulations described in certain embodiments of the present invention include, but are not limited to, skin care, wound care, respiratory care, and oral care formulations, including, but not limited to, medical, personal care, and consumer products.

Formulations described in certain embodiments of the present invention can be suitably provided in forms including, but not limited to, liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (e.g., coated tablets), granules, powders, lozenges, pastilles, capsules (e.g., hard and soft gelatin capsules), sachets, pills, ampoules, boluses, suppositories, pessaries, tinctures, gels, pastes, ointments, creams, lotions, oils, foams, sprays, mists, or aerosols.

Formulations described in certain embodiments of the present invention can be suitably provided in forms including, but not limited to, patches, adhesive plasters, bandages, dressings, or the like, which are impregnated with one or more active compounds, and, optionally, one or more pharmaceutically acceptable ingredients, including, but not limited to, penetration, permeation, and absorption enhancers. Formations disclosed in certain embodiments of the present invention can also be suitably provided in forms including, but not limited to, depots or reservoirs.

In some embodiments of the present invention, the secreted material of the antibacterial and/or antifungal compositions of the present invention is formulated with one or more pharmaceutically acceptable ingredients. Formulations disclosed in certain embodiments of the present invention can further comprise other active agents, including, but not limited to, other therapeutic or prophylactic agents.

In certain embodiments, products and formulations described in certain embodiments of the present invention can be suitable for skin care or wound care. In some embodiments of the present invention, the secreted material of the antibacterial and/or antifungal compositions of the present invention is formulated for topical administration, particularly for use or application to, or on, the skin. In other embodiments of the present invention, formulations suitable for topical administration include, but are not limited to, gels, pastes, ointments, creams, lotions, oils, patches, adhesive plasters, bandages, dressings, depots, cements, glues, and reservoirs.

The term "skin care," as used herein, unless stated otherwise, by itself or in combination with other terms, means topical personal care and/or health care, products of which are useful for the treatment of adult or infant skin, including human skin, to maintain or improve the health of the skin or to improve the appearance of the skin.

The term "wound care," as used herein, unless stated otherwise, by itself or in combination with other terms, includes, but is not limited to, treatment of a wound to assist in the closure or healing of the wound, and/or to reduce the pain or scarring associated with the wound, maintaining or improving the health of such tissue or skin, repairing such tissue or skin, and reducing irritation, itching, and/or redness of such tissue or skin.

In certain embodiments of the present invention, ointments are prepared from the secreted material of the antibacterial and/or antifungal compositions of the present invention and a paraffinic or water-miscible ointment base.

In certain embodiments of the present invention, creams are prepared from the probiotic compounds or lysates of the present invention and an oil-in-water cream base. In some embodiments of the present invention, the aqueous phase of the cream base can include, for example, at least about 30% w/w of a polyhydric alcohol, i.e., an alcohol having two or more hydroxyl groups, such as propylene glycol, butane-1, 3-diol, mannitol, sorbitol, glycerol, and polyethylene glycol, and mixtures thereof. In other embodiments, topical formulations in the form of creams may preferably include a compound that enhances absorption or penetration of the active compound through the skin or other affected areas. In certain embodiments, examples of such dermal penetration enhancers include, but are not limited to, dimethylsulfoxide and related analogues.

In certain embodiments of the present invention, emulsions are prepared from the probiotic compounds or lysates of the present invention and an oily phase, which can, optionally, comprise an emulsifier (i.e., an emulgent), or a mixture of at least one emulsifier with a fat and/or an oil. In preferable embodiments, a hydrophilic emulsifier is included together with a lipophilic emulsifier that acts as a stabilizer. In other preferable embodiments, a hydrophilic emulsifier is included tougher with a lipophilic emulsifier, an oil, and a fat. Without being bound by theory, it is thought that together, the emulsifier(s), with or without stabilizer(s), make up the so-called emulsifying wax, and the emulsifying wax together with the oil and/or fat constitute the so-called emulsifying ointment base that forms the oily dispersed phase of the emulsion formulations.

In certain embodiments of the present invention, suitable emulgents and emulsion stabilizers include, but are not limited to, Tween 60, Span 80, cetostearyl alcohol, myristyl alcohol, glyceryl monostearate, and sodium lauryl sulphate. Without being bound by theory, the choice of suitable oils or fats for the formulations of certain embodiments of the present invention is based upon achieving the desired cosmetic properties, because the solubility of the active compound(s) in most oils likely to be used in pharmaceutical emulsion formulations may be very low. Accordingly, in preferable embodiments of the present invention, creams should be non-greasy, non-staining, and washable with consistency suitable to avoid leakage from tubes or other containers. In other embodiments of the present invention, straight- or branched-chain, mono- or dibasic alkyl esters, including, but not limited to, di-isoadipate, isocetyl stearate, propylene glycol diesters of coconut fatty acids, isopropyl myristate, decyl oleate, isopropyl palmitate, butyl stearate, 2-ethylhexyl palmitate, or a blend of branched chain esters known as Crodamol CAP may be used. In preferred embodiments of the present invention, butyl stearate, 2-ethylhexyl palmitate, or Crodamol CAP may be used. In other embodiments, straight- or branched-chain, mono- or dibasic alkyl esters can be used alone or in combinations, depending upon the properties required. In yet other embodiments, high melting point lipids, such as white soft paraffin, and/or liquid paraffin, or other mineral oils, may be used.

Certain embodiments of the present invention are suitable for oral care. The term "oral care," as used herein, unless stated otherwise, by itself or in combination with other terms, means uses of materials in the oral cavity or any portion thereof, including, but not limited to, use on the teeth, mucosa, tongue, and the like. Products and uses in the field of oral care include, but are not limited to, those intended for tooth aesthetics including, but not limited to, tooth whitening, stain prevention, and the like, as well as anti-plaque, anti-gingivitis, anti-sensitivity, anti-caries, breath freshening, drymouth relief, erosion repair and prevention, active delivery and retention, sensory enhancement, and mouth feel alteration, and the like.

Formulations described in certain embodiments of the present invention that are suitable for oral care include, but are not limited to, dental sprays, mouthwashes, toothpastes, lozenges, antibacterial and/or antifungal washes, drinks (e.g., milk and/or yoghurt), food items (e.g., yoghurt, ice cream, candy bars), or powdered foods (e.g., powdered milk). Formulations described in certain embodiments of the present invention that are suitable for oral care include formulations suitable for oral and/or buccal administration.

Formulations described in certain embodiments of the present invention that are suitable for oral administration (e.g., by ingestion) include, but are not limited to, liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations described in certain embodiments of the present invention that are suitable for buccal administration include, but are not limited to, mouthwashes, losenges, pastilles, patches, adhesive plasters, depots, and reservoirs. In some embodiments of the present invention, losenges may include the active probiotic compound or lysate of the present invention in a flavored basis, usually sucrose and acacia or tragacanth. In other embodiments of the present invention, pastilles may include the active probiotic compound or lysate of the present invention in an inert matrix, such as gelatin or glycerin, or sucrose and acacia. In yet other embodiments of the present invention, mouthwashes may include the active probiotic compound or lysate of the present invention in a suitable liquid carrier.

Formulations described in certain embodiments of the present invention are suitably provided as patches, adhesive plasters, bandages, dressings, and the like, that are impregnated with, or coated with, one or more active probiotic compounds or lysates of the present invention and, optionally, one or more other pharmaceutically acceptable ingredients, including, but not limited to, penetration, permeation, and/or absorption enhancers. In other embodiments, one or more active probiotic compounds, lysates, or culture media of the present invention may also be provided in the form of coatings for medical devices, such as implants, prosthetics, surgical instruments, gloves, catheters, valves, pacemakers, and the like.

In certain embodiments, formulations described in embodiments of the present invention can include at least about 0.01%, about 0.05%, about 0.1%, about 0.2%, about 0.3%, about 0.4%, about 0.5%, about 0.6%, about 0.7%, about 0.8%, about 0.9%, about 1.0%, about 1.5%, about 2.0%, about 3.0%, about 4.0%, about 5.0%, about 6.0%, about 7.0%, about 8.0%, about 9.0%, about 10.0%, about 11.0%, about 12.0%, about 13.0%, about 14.0%, about 15.0%, about 16.0%, about 17.0%, about 18.0%, about 19.0%, about 20.0%, about 25.0%, about 30.0%, about 35.0%, about 40.0%, about 45.0%, or about 50.0% by weight of active probiotic compound or lysate. In other embodiments, formulations described in embodiments of the present invention can include at least about 0.01% to about 30%, about 0.01% to about 20%, about 0.01% to about 5%, about 0.1% to about 30%, about 0.1% to about 20%, about 0.1% to about 15%, about 0.1% to about 10%, about 0.1% to about 5%, about 0.2% to about 5%, about 0.3% to about 5%, about 0.4% to about 5%, about 0.5% to about 5%, about 1% to about 5% by weight of active probiotic compound or lysate.

Compositions for and Methods of Treating, Removing, or Preventing the Accumulation of Bacteria, Fungus, and/or Yeast on a Surface, and/or Treating or Preventing Fungal, Bacterial, and/or Yeast Infections in a Human Subject In an embodiment, a composition that repels, reduces, and/or removes plant fungal pathogens includes secreted material in a carrier.

In another embodiment, a composition that repels, reduces, and/or removes plant fungal pathogens includes secreted material in a carrier, wherein the composition is formulated for use as an anti-fungal composition.

In yet another embodiment, a composition that repels, reduces, and/or removes plant fungal pathogens includes secreted material in a carrier, wherein the composition is formulated for use as a cream, gel, or spray.

In yet another embodiment, a composition that repels, reduces, and/or removes plant fungal pathogens includes secreted material in a carrier, wherein the composition is a pharmaceutical composition.

In yet another embodiment, a composition that repels, reduces, and/or removes plant fungal pathogens includes secreted material in a carrier, wherein the composition is formulated for topical administration.

In yet another embodiment, a composition that repels, reduces, and/or removes plant fungal pathogens includes secreted material in a carrier, wherein the composition is formulated for use in medicine.

In yet another embodiment, a composition that repels, reduces, and/or removes plant fungal pathogens includes secreted material in a carrier, wherein the composition is formulated for use in a method of preventing, removing, reducing, or treating a bacterial or fungal infection.

In yet another embodiment, a composition that repels, reduces, and/or removes plant fungal pathogens includes secreted material in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes secreted material in a carrier, wherein the composition is formulated for use in a method of preventing, removing, reducing, or treating a bacterial, yeast, or fungal infection.

In yet another embodiment, a composition that repels, reduces, and/or removes plant fungal pathogens includes secreted material in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes secreted material in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes secreted material in a carrier, wherein the carrier is suitable for topical application to skin or a mucous membrane of a mammal.

In yet another embodiment, a composition that repels, reduces, and/or removes plant fungal pathogens includes secreted material in a carrier, wherein the composition can include from about 1% to about 75% emu oil by weight.

In yet another embodiment, a composition that repels, reduces, and/or removes plant fungal pathogens includes secreted material in a carrier, further including an effective amount of a fructooligosaccharide.

In yet another embodiment, a composition that repels, reduces, and/or removes plant fungal pathogens includes secreted material in a carrier, further including an effective amount of a fructooligosaccharide, wherein the fructooligosaccharide is present in an amount of from about 10 to about 1000 milligrams per gram of composition.

In yet another embodiment, a composition that repels, reduces, and/or removes plant fungal pathogens includes secreted material in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes plant fungal pathogens includes secreted material in a carrier, further including an effective amount of a fructoligosaccharide, wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria.

In yet another embodiment, a composition that repels, reduces, and/or removes plant fungal pathogens includes secreted material in a carrier, wherein the carrier can include media obtained from a culture containing a probiotic bacteria, further wherein the composition is formulated for use as an anti-fungal composition.

In yet another embodiment, a composition that repels, reduces, and/or removes plant fungal pathogens includes secreted material in a carrier, wherein the carrier can include media obtained from a culture containing a probiotic bacteria, further wherein the composition is formulated for use as a cream, gel, or spray.

In yet another embodiment, a composition that repels, reduces, and/or removes plant fungal pathogens includes secreted material in a carrier, wherein the carrier can include media obtained from a culture containing a probiotic bacteria, further wherein the composition is a pharmaceutical composition.

In yet another embodiment, a composition that repels, reduces, and/or removes plant fungal pathogens includes secreted material in a carrier, wherein the carrier can include media obtained from a culture containing a probiotic bacteria, further wherein the composition is formulated for topical administration.

In yet another embodiment, a composition that repels, reduces, and/or removes plant fungal pathogens includes secreted material in a carrier, wherein the carrier can include media obtained from a culture containing a probiotic bacteria, further wherein the composition is formulated for use in medicine.

In yet another embodiment, a composition that repels, reduces, and/or removes plant fungal pathogens includes secreted material in a carrier, wherein the carrier can include media obtained from a culture containing a probiotic bacteria, further wherein the composition is formulated for use in a method of preventing, removing, reducing, or treating a bacterial or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is cultured under aerobic conditions.

In yet another embodiment, a composition that repels, reduces, and/or removes plant fungal pathogens includes secreted material in a carrier, wherein the carrier can include media obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes plant fungal pathogens includes secreted material in a carrier, wherein the carrier can include media obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes secreted material in a carrier, wherein the carrier can include media obtained from a culture containing a probiotic bacteria, further wherein the carrier is suitable for topical application to skin or a mucous membrane of a mammal.

In yet another embodiment, a composition that repels, reduces, and/or removes plant fungal pathogens includes secreted material in a carrier, wherein the carrier can include media obtained from a culture containing a probiotic bacteria, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the carrier includes an effective amount of a fructooligosaccharide.

In yet another embodiment, a composition that repels, reduces, and/or removes plant fungal pathogens includes secreted material in a carrier, wherein the carrier can include media obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is included in the composition in the form of spores.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is included in the composition in the form of a dried cell mass.

In yet another embodiment, a composition that repels, reduces, and/or removes plant fungal pathogens includes secreted material in a carrier, wherein the carrier can include media obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria.

In yet another embodiment, a composition that repels, reduces, and/or removes plant fungal pathogens includes secreted material in a carrier, wherein the carrier includes substantially no intact probiotic bacteria, lysed bacteria, or bacterial fragments.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes secreted material in a carrier, wherein the carrier can include media obtained from a culture containing probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes plant fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use as an anti-fungal composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for topical administration.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is a supernatant or filtrate of a culture of the probiotic bacteria.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use as an anti-fungal composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the probiotic bacteria is included in the composition in the form of spores.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for topical administration.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use as an anti-fungal composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes plant fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes plant fungal pathogens includes surfactin in a carrier.

In yet another embodiment, a composition that repels, reduces, and/or removes plant fungal pathogens includes surfactin in a carrier, wherein the composition is formulated for use as an anti-fungal composition.

In yet another embodiment, a composition that repels, reduces, and/or removes plant fungal pathogens includes surfactin in a carrier, wherein the composition is formulated for use as a cream, gel, or spray.

In yet another embodiment, a composition that repels, reduces, and/or removes plant fungal pathogens includes surfactin in a carrier, wherein the composition is a pharmaceutical composition.

In yet another embodiment, a composition that repels, reduces, and/or removes plant fungal pathogens includes surfactin in a carrier, wherein the composition is formulated for topical administration.

In yet another embodiment, a composition that repels, reduces, and/or removes plant fungal pathogens includes surfactin in a carrier, wherein the composition is formulated for use in medicine.

In yet another embodiment, a composition that repels, reduces, and/or removes plant fungal pathogens includes surfactin in a carrier, wherein the composition is formulated for use in a method of preventing, removing, reducing, or treating a bacterial or fungal infection.

In yet another embodiment, a composition that repels, reduces, and/or removes plant fungal pathogens includes surfactin in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes surfactin in a carrier, wherein the composition is formulated for use in a method of preventing, removing, reducing, or treating a bacterial, yeast, or fungal infection.

In yet another embodiment, a composition that repels, reduces, and/or removes plant fungal pathogens includes surfactin in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes surfactin in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes surfactin in a carrier, wherein the carrier is suitable for topical application to skin or a mucous membrane of a mammal.

In yet another embodiment, a composition that repels, reduces, and/or removes plant fungal pathogens includes surfactin in a carrier, wherein the composition can include from about 1% to about 75% emu oil by weight.

In yet another embodiment, a composition that repels, reduces, and/or removes plant fungal pathogens includes surfactin in a carrier, further including an effective amount of a fructooligosaccharide.

In yet another embodiment, a composition that repels, reduces, and/or removes plant fungal pathogens includes surfactin in a carrier, further including an effective amount of a fructooligosaccharide, wherein the fructooligosaccharide is present in an amount of from about 10 to about 1000 milligrams per gram of composition.

In yet another embodiment, a composition that repels, reduces, and/or removes plant fungal pathogens includes surfactin in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes plant fungal pathogens includes surfactin in a carrier, further including an effective amount of a fructooligosaccharide, wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria.

In yet another embodiment, a composition that repels, reduces, and/or removes plant fungal pathogens includes surfactin in a carrier, wherein the surfactin is obtained from a culture containing a probiotic bacteria, further wherein the composition is formulated for use as an anti-fungal composition.

In yet another embodiment, a composition that repels, reduces, and/or removes plant fungal pathogens includes surfactin in a carrier, wherein the surfactin is obtained from a culture containing a probiotic bacteria, further wherein the composition is formulated for use as a cream, gel, or spray.

In yet another embodiment, a composition that repels, reduces, and/or removes plant fungal pathogens includes surfactin in a carrier, wherein the surfactin is obtained from a culture containing a probiotic bacteria, further wherein the composition is a pharmaceutical composition.

In yet another embodiment, a composition that repels, reduces, and/or removes plant fungal pathogens includes surfactin in a carrier, wherein the surfactin is obtained from a culture containing a probiotic bacteria, further wherein the composition is formulated for topical administration.

In yet another embodiment, a composition that repels, reduces, and/or removes plant fungal pathogens includes surfactin in a carrier, wherein the surfactin is obtained from a culture containing a probiotic bacteria, further wherein the composition is formulated for use in medicine.

In yet another embodiment, a composition that repels, reduces, and/or removes plant fungal pathogens includes surfactin in a carrier, wherein the surfactin is obtained from a culture containing a probiotic bacteria, further wherein the composition is formulated for use in a method of preventing, removing, reducing, or treating a bacterial or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is cultured under aerobic conditions.

In yet another embodiment, a composition that repels, reduces, and/or removes plant fungal pathogens includes surfactin in a carrier, wherein the surfactin is obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes plant fungal pathogens includes surfactin in a carrier, wherein the surfactin is obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the carrier is selected from the group consisting of an emulsion, cream, lotion, gel, oil, ointment, suspension, aerosol spray, powder, aerosol powder, and semi solid formulation.

In yet another embodiment, a composition that repels, reduces, and/or removes plant fungal pathogens includes surfactin in a carrier, wherein the surfactin is obtained from a culture containing a probiotic bacteria, further wherein the carrier is suitable for topical application to skin or a mucous membrane of a mammal.

In yet another embodiment, a composition that repels, reduces, and/or removes plant fungal pathogens includes surfactin in a carrier, wherein the surfactin is obtained from a culture containing a probiotic bacteria, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the carrier includes an effective amount of a fructooligosaccharide.

In yet another embodiment, a composition that repels, reduces, and/or removes plant fungal pathogens includes surfactin in a carrier, wherein the surfactin is obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is included in the composition in the form of spores.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is included in the composition in the form of a dried cell mass.

In yet another embodiment, a composition that repels, reduces, and/or removes plant fungal pathogens includes surfactin in a carrier, wherein the surfactin is obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the extracellular product is surfactin.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria, further wherein the extracellular product is surfactin.

In yet another embodiment, a composition that repels, reduces, and/or removes plant fungal pathogens includes surfactin in a carrier, wherein the carrier includes substantially no intact probiotic bacteria, lysed bacteria, or bacterial fragments.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes plant fungal pathogens includes surfactin in a carrier, wherein the surfactin is obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is surfactin.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is a supernatant or filtrate of a culture of the probiotic bacteria, further wherein the extracellular product is surfactin.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the composition is formulated for use as an anti-fungal composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the composition is formulated for topical administration.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is surfactin.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is a supernatant or filtrate of a culture of the probiotic bacteria, further wherein the extracellular product is surfactin.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is surfactin.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria, further wherein the extracellular product is surfactin.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the composition is formulated for use as an anti-fungal composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the probiotic bacteria is included in the composition in the form of spores.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is surfactin.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria, further wherein the extracellular product is surfactin.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an antifungal composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is surfactin.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of the probiotic bacteria, further wherein the extracellular product is surfactin.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the composition is formulated for use as an anti-fungal composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is surfactin.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria, further wherein the extracellular product is surfactin.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes plant fungal pathogens includes surfactin in a carrier, wherein the surfactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is surfactin.

In yet another embodiment, a composition that repels, reduces, and/or removes plant fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of the probiotic bacteria, further wherein the extracellular product is surfactin.

In an embodiment, a composition that repels, reduces, and/or removes fungal pathogens includes secreted material in a carrier.

In another embodiment, a composition that repels, reduces, and/or removes fungal pathogens includes secreted material in a carrier, wherein the composition is formulated for use as an anti-fungal composition.

In yet another embodiment, a composition that repels, reduces, and/or removes fungal pathogens includes secreted material in a carrier, wherein the composition is formulated for use as a cream, gel, or spray.

In yet another embodiment, a composition that repels, reduces, and/or removes fungal pathogens includes secreted material in a carrier, wherein the composition is a pharmaceutical composition.

In yet another embodiment, a composition that repels, reduces, and/or removes fungal pathogens includes secreted material in a carrier, wherein the composition is formulated for topical administration.

In yet another embodiment, a composition that repels, reduces, and/or removes fungal pathogens includes secreted material in a carrier, wherein the composition is formulated for use in medicine.

In yet another embodiment, a composition that repels, reduces, and/or removes fungal pathogens includes secreted material in a carrier, wherein the composition is formulated for use in a method of preventing, removing, reducing, or treating a bacterial or fungal infection.

In yet another embodiment, a composition that repels, reduces, and/or removes fungal pathogens includes secreted material in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes secreted material in a carrier, wherein the composition is formulated for use in a method of preventing, removing, reducing, or treating a bacterial, yeast, or fungal infection.

In yet another embodiment, a composition that repels, reduces, and/or removes fungal pathogens includes secreted material in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes secreted material in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes secreted material in a carrier, wherein the carrier is suitable for topical application to skin or a mucous membrane of a mammal.

In yet another embodiment, a composition that repels, reduces, and/or removes fungal pathogens includes secreted material in a carrier, wherein the composition can include from about 1% to about 75% emu oil by weight.

In yet another embodiment, a composition that repels, reduces, and/or removes fungal pathogens includes secreted material in a carrier, further including an effective amount of a fructooligosaccharide.

In yet another embodiment, a composition that repels, reduces, and/or removes fungal pathogens includes secreted material in a carrier, further including an effective amount of a fructooligosaccharide, wherein the fructooligosaccharide is present in an amount of from about 10 to about 1000 milligrams per gram of composition.

In yet another embodiment, a composition that repels, reduces, and/or removes fungal pathogens includes secreted material in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes fungal pathogens includes secreted material in a carrier, further including an effective amount of a fructooligosaccharide, wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria.

In yet another embodiment, a composition that repels, reduces, and/or removes fungal pathogens includes secreted material in a carrier, wherein the carrier can include media obtained from a culture containing a probiotic bacteria, further wherein the composition is formulated for use as an anti-fungal composition.

In yet another embodiment, a composition that repels, reduces, and/or removes fungal pathogens includes secreted material in a carrier, wherein the carrier can include media obtained from a culture containing a probiotic bacteria, further wherein the composition is formulated for use as a cream, gel, or spray.

In yet another embodiment, a composition that repels, reduces, and/or removes fungal pathogens includes secreted material in a carrier, wherein the carrier can include media obtained from a culture containing a probiotic bacteria, further wherein the composition is a pharmaceutical composition.

In yet another embodiment, a composition that repels, reduces, and/or removes fungal pathogens includes secreted material in a carrier, wherein the carrier can include media obtained from a culture containing a probiotic bacteria, further wherein the composition is formulated for topical administration.

In yet another embodiment, a composition that repels, reduces, and/or removes fungal pathogens includes secreted material in a carrier, wherein the carrier can include media obtained from a culture containing a probiotic bacteria, further wherein the composition is formulated for use in medicine.

In yet another embodiment, a composition that repels, reduces, and/or removes fungal pathogens includes secreted material in a carrier, wherein the carrier can include media obtained from a culture containing a probiotic bacteria, further wherein the composition is formulated for use in a method of preventing, removing, reducing, or treating a bacterial or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is cultured under aerobic conditions.

In yet another embodiment, a composition that repels, reduces, and/or removes fungal pathogens includes secreted material in a carrier, wherein the carrier can include media obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes fungal pathogens includes secreted material in a carrier, wherein the carrier can include media obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes secreted material in a carrier, wherein the carrier can include media obtained from a culture containing a probiotic bacteria, further wherein the carrier is suitable for topical application to skin or a mucous membrane of a mammal.

In yet another embodiment, a composition that repels, reduces, and/or removes fungal pathogens includes secreted material in a carrier, wherein the carrier can include media obtained from a culture containing a probiotic bacteria, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the carrier includes an effective amount of a fructooligosaccharide.

In yet another embodiment, a composition that repels, reduces, and/or removes fungal pathogens includes secreted material in a carrier, wherein the carrier can include media obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is included in the composition in the form of spores.

In yet another embodiment, a composition that repels, reduces, and/or removes fungal pathogens includes secreted material in a carrier, wherein the carrier can include media obtained from a culture containing a probiotic bacteria, further wherein the probiotic bacteria is included in the composition in the form of a dried cell mass.

In yet another embodiment, a composition that repels, reduces, and/or removes fungal pathogens includes secreted material in a carrier, wherein the carrier can include media obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria.

In yet another embodiment, a composition that repels, reduces, and/or removes fungal pathogens includes secreted material in a carrier, wherein the carrier includes substantially no intact probiotic bacteria, lysed bacteria, or bacterial fragments.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use as an anti-fungal composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for topical administration.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is a supernatant or filtrate of a culture of the probiotic bacteria.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use as an anti-fungal composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the probiotic bacteria is included in the composition in the form of spores.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use as an anti-fungal composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccahride is present in an amount of from about 10 to about 1000 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes fungal pathogens includes iturin in a carrier.

In yet another embodiment, a composition that repels, reduces, and/or removes fungal pathogens includes iturin in a carrier, wherein the composition is formulated for use as an anti-fungal composition.

In yet another embodiment, a composition that repels, reduces, and/or removes fungal pathogens includes iturin in a carrier, wherein the composition is formulated for use as a cream, gel, or spray.

In yet another embodiment, a composition that repels, reduces, and/or removes fungal pathogens includes iturin in a carrier, wherein the composition is a pharmaceutical composition.

In yet another embodiment, a composition that repels, reduces, and/or removes fungal pathogens includes iturin in a carrier, wherein the composition is formulated for topical administration.

In yet another embodiment, a composition that repels, reduces, and/or removes fungal pathogens includes iturin in a carrier, wherein the composition is formulated for use in medicine.

In yet another embodiment, a composition that repels, reduces, and/or removes fungal pathogens includes iturin in a carrier, wherein the composition is formulated for use in a method of preventing, removing, reducing, or treating a bacterial or fungal infection.

In yet another embodiment, a composition that repels, reduces, and/or removes fungal pathogens includes iturin in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin in a carrier, wherein the composition is formulated for use in a method of preventing, removing, reducing, or treating a bacterial, yeast, or fungal infection.

In yet another embodiment, a composition that repels, reduces, and/or removes fungal pathogens includes iturin in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin in a carrier, wherein the carrier is suitable for topical application to skin or a mucous membrane of a mammal.

In yet another embodiment, a composition that repels, reduces, and/or removes fungal pathogens includes iturin in a carrier, wherein the composition can include from about 1% to about 75% emu oil by weight.

In yet another embodiment, a composition that repels, reduces, and/or removes fungal pathogens includes iturin in a carrier, further including an effective amount of a fructooligosaccharide.

In yet another embodiment, a composition that repels, reduces, and/or removes fungal pathogens includes iturin in a carrier, further including an effective amount of a fructooligosaccharide, wherein the fructooligosaccharide is present in an amount of from about 10 to about 1000 milligrams per gram of composition.

In yet another embodiment, a composition that repels, reduces, and/or removes fungal pathogens includes iturin in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes fungal pathogens includes iturin in a carrier, further including an effective amount of a fructooligosaccharide, wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria.

In yet another embodiment, a composition that repels, reduces, and/or removes fungal pathogens includes iturin in a carrier, wherein the iturin is obtained from a culture containing a probiotic bacteria, further wherein the composition is formulated for use as an anti-fungal composition.

In yet another embodiment, a composition that repels, reduces, and/or removes fungal pathogens includes iturin in a carrier, wherein the iturin is obtained from a culture containing a probiotic bacteria, further wherein the composition is formulated for use as a cream, gel, or spray.

In yet another embodiment, a composition that repels, reduces, and/or removes fungal pathogens includes iturin in a carrier, wherein the iturin is obtained from a culture containing a probiotic bacteria, further wherein the composition is a pharmaceutical composition.

In yet another embodiment, a composition that repels, reduces, and/or removes fungal pathogens includes iturin in a carrier, wherein the iturin is obtained from a culture containing a probiotic bacteria, further wherein the composition is formulated for topical administration.

In yet another embodiment, a composition that repels, reduces, and/or removes fungal pathogens includes iturin in a carrier, wherein the iturin is obtained from a culture containing a probiotic bacteria, further wherein the composition is formulated for use in medicine.

In yet another embodiment, a composition that repels, reduces, and/or removes fungal pathogens includes iturin in a carrier, wherein the iturin is obtained from a culture containing a probiotic bacteria, further wherein the composition is formulated for use in a method of preventing, removing, reducing, or treating a bacterial or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is cultured under aerobic conditions.

In yet another embodiment, a composition that repels, reduces, and/or removes fungal pathogens includes iturin in a carrier, wherein the iturin is obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes fungal pathogens includes iturin in a carrier, wherein the iturin is obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin in a carrier, wherein the iturin is obtained from a culture containing a probiotic bacteria, further wherein the carrier is suitable for topical application to skin or a mucous membrane of a mammal.

In yet another embodiment, a composition that repels, reduces, and/or removes fungal pathogens includes iturin in a carrier, wherein the iturin is obtained from a culture containing a probiotic bacteria, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the carrier includes an effective amount of a fructooligosaccharide.

In yet another embodiment, a composition that repels, reduces, and/or removes fungal pathogens includes iturin in a carrier, wherein the iturin is obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin in a carrier, wherein the iturin is obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin in a carrier, wherein the iturin is obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is included in the composition in the form of spores.

In yet another embodiment, a composition that repels, reduces, and/or removes fungal pathogens includes iturin in a carrier, wherein the iturin is obtained from a culture containing a probiotic bacteria, further wherein the probiotic bacteria is included in the composition in the form of a dried cell mass.

In yet another embodiment, a composition that repels, reduces, and/or removes fungal pathogens includes iturin in a carrier, wherein the iturin is obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the extracellular product is iturin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria, further wherein the extracellular product is iturin.

In yet another embodiment, a composition that repels, reduces, and/or removes fungal pathogens includes iturin in a carrier, wherein the iturin includes substantially no intact probiotic bacteria, lysed bacteria, or bacterial fragments.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes iturin in a carrier, wherein the iturin is obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is iturin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is a supernatant or filtrate of a culture of the probiotic bacteria, further wherein the extracellular product is iturin.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the composition is formulated for use as an anti-fungal composition.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the composition is formulated for topical administration.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical application to skin or a mucous membrane of a mammal, wherein the probiotic bacteria is a *Bacillus* spp. bacteria, further wherein the extracellular product is iturin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is a supernatant or filtrate of a culture of the probiotic bacteria, further wherein the extracellular product is iturin.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes iturin in a carrier, wherein the iturin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is iturin.

In yet another embodiment, a composition that repels, reduces, and/or removes fungal pathogens includes an extracellular product of a probiotic bacteria in a pharmaceutically acceptable bacteria suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria, further wherein the extracellular product is iturin.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the composition is formulated for use as an anti-fungal composition.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the probiotic bacteria is included in the composition in the form of spores.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is iturin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria, further wherein the extracellular product is iturin.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes iturin in a carrier, wherein the iturin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is iturin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of the probiotic bacteria, further wherein the extracellular product is iturin.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the composition is formulated for use as an anti-fungal composition.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is iturin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria, further wherein the extracellular product is iturin.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes iturin in a carrier, wherein the iturin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is iturin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of the probiotic bacteria, further wherein the extracellular product is iturin.

In yet another embodiment, a composition that repels, reduces, and/or removes fungal pathogens includes bacillomycin in a carrier.

In yet another embodiment, a composition that repels, reduces, and/or removes fungal pathogens includes bacillomycin in a carrier, wherein the composition is formulated for use as an anti-fungal composition.

In yet another embodiment, a composition that repels, reduces, and/or removes fungal pathogens includes bacillomycin in a carrier, wherein the composition is formulated for use as a cream, gel, or spray.

In yet another embodiment, a composition that repels, reduces, and/or removes fungal pathogens includes bacillomycin in a carrier, wherein the composition is a pharmaceutical composition.

In yet another embodiment, a composition that repels, reduces, and/or removes fungal pathogens includes bacillomycin in a carrier, wherein the composition is formulated for topical administration.

In yet another embodiment, a composition that repels, reduces, and/or removes fungal pathogens includes bacillomycin in a carrier, wherein the composition is formulated for use in medicine.

In yet another embodiment, a composition that repels, reduces, and/or removes fungal pathogens includes bacillomycin in a carrier, wherein the composition is formulated for use in a method of preventing, removing, reducing, or treating a bacterial or fungal infection.

In yet another embodiment, a composition that repels, reduces, and/or removes fungal pathogens includes bacillomycin in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes bacillomycin in a carrier, wherein the composition is formulated for use in a method of preventing, removing, reducing, or treating a bacterial, yeast, or fungal infection.

In yet another embodiment, a composition that repels, reduces, and/or removes fungal pathogens includes bacillomycin in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes bacillomycin in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes bacillomycin in a carrier, wherein the carrier is suitable for topical application to skin or a mucous membrane of a mammal.

In yet another embodiment, a composition that repels, reduces, and/or removes fungal pathogens includes bacillomycin in a carrier, wherein the composition can include from about 1% to about 75% emu oil by weight.

In yet another embodiment, a composition that repels, reduces, and/or removes fungal pathogens includes bacillomycin in a carrier, further including an effective amount of a fructooligosaccharide.

In yet another embodiment, a composition that repels, reduces, and/or removes fungal pathogens includes bacillomycin in a carrier, further including an effective amount of a fructooligosaccharide, wherein the fructooligosaccahride is present in an amount of from about 10 to about 1000 milligrams per gram of composition.

In yet another embodiment, a composition that repels, reduces, and/or removes fungal pathogens includes bacillomycin in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes fungal pathogens includes bacillomycin in a carrier, further including an effective amount of a fructooligosaccahride, wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria.

In yet another embodiment, a composition that repels, reduces, and/or removes fungal pathogens includes bacillomycin in a carrier, wherein the bacillomycin is obtained from a culture containing a probiotic bacteria, further wherein the composition is formulated for use as an antifungal composition.

In yet another embodiment, a composition that repels, reduces, and/or removes fungal pathogens includes bacillomycin in a carrier, wherein the bacillomycin is obtained from a culture containing a probiotic bacteria, further wherein the composition is formulated for use as a cream, gel, or spray.

In yet another embodiment, a composition that repels, reduces, and/or removes fungal pathogens includes bacillomycin in a carrier, wherein the bacillomycin is obtained from a culture containing a probiotic bacteria, further wherein the composition is a pharmaceutical composition.

In yet another embodiment, a composition that repels, reduces, and/or removes fungal pathogens includes bacillomycin in a carrier, wherein the bacillomycin is obtained from a culture containing a probiotic bacteria, further wherein the composition is formulated for topical administration.

In yet another embodiment, a composition that repels, reduces, and/or removes fungal pathogens includes bacillomycin in a carrier, wherein the bacillomycin is obtained from a culture containing a probiotic bacteria, further wherein the composition is formulated for use in medicine.

In yet another embodiment, a composition that repels, reduces, and/or removes fungal pathogens includes bacillomycin in a carrier, wherein the bacillomycin is obtained from a culture containing a probiotic bacteria, further wherein the composition is formulated for use in a method of preventing, removing, reducing, or treating a bacterial or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is cultured under aerobic conditions.

In yet another embodiment, a composition that repels, reduces, and/or removes fungal pathogens includes bacillomycin in a carrier, wherein the bacillomycin is obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes fungal pathogens includes bacillomycin in a carrier, wherein the bacillomycin is obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes bacillomycin in a carrier, wherein the bacillomycin is obtained from a culture containing a probiotic bacteria, further wherein the carrier is suitable for topical application to skin or a mucous membrane of a mammal.

In yet another embodiment, a composition that repels, reduces, and/or removes fungal pathogens includes bacillomycin in a carrier, wherein the bacillomycin is obtained from a culture containing a probiotic bacteria, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the carrier includes an effective amount of a fructooligosaccharide.

In yet another embodiment, a composition that repels, reduces, and/or removes fungal pathogens includes bacillomycin in a carrier, wherein the bacillomycin is obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is included in the composition in the form of spores.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is included in the composition in the form of a dried cell mass.

In yet another embodiment, a composition that repels, reduces, and/or removes fungal pathogens includes bacillomycin in a carrier, wherein the bacillomycin is obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the extracellular product is bacillomycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria, further wherein the extracellular product is bacillomycin.

In yet another embodiment, a composition that repels, reduces, and/or removes fungal pathogens includes bacillomycin in a carrier, wherein the carrier includes substantially no intact probiotic bacteria, lysed bacteria, or bacterial fragments.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the composition is formulated for use as an antifungal composition.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes bacillomycin in a carrier, further the bacillomycin is obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes bacillomycin in a carrier, wherein the bacillomycin is obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is bacillomycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillomycin.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the composition is formulated for use as an anti-fungal composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the composition is formulated for topical administration.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or mucous membrane of a mammal, wherein the probiotic bacteria is a *Bacillus* spp. bacteria, further wherein the extracellular product is bacillomycin.

In yet another embodiment, a composition that repels, reduces, and/or removes fungal pathogens includes an extracellular product of a probiotic bacteria in a pharmaceutically acceptable carrier suitable for topical administration to skin or mucous membrane of a mammal, wherein the probiotic bacteria is a *Bacillus* spp. bacteria, further wherein the extracellular product is a supernatant or filtrate of a culture of the probiotic bacteria, further wherein the extracellular product is bacillomycin.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccahride, further wherein the fructooligosaccharide is present in an amount of from about 10 to about 1000 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is bacillomycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillomycin.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the composition is formulated for use as an anti-fungal composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the probiotic bacteria is included in the composition in the form of spores.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is bacillomycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria, further wherein the extracellular product is bacillomycin.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is bacillomycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillomycin.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the composition is formulated for use as an anti-fungal composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is bacillomycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria, further wherein the extracellular product is bacillomycin.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is a *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes bacillomycin in a carrier, wherein the bacillomycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is bacillomycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillomycin.

In yet another embodiment, a composition that repels, reduces, and/or removes fungal pathogens includes fengycin in a carrier.

In yet another embodiment, a composition that repels, reduces, and/or removes fungal pathogens includes fengycin in a carrier, wherein the composition is formulated for use as an anti-fungal composition.

In yet another embodiment, a composition that repels, reduces, and/or removes fungal pathogens includes fengycin in a carrier, wherein the composition is formulated for use as a cream, gel, or spray.

In yet another embodiment, a composition that repels, reduces, and/or removes fungal pathogens includes fengycin in a carrier, wherein the composition is a pharmaceutical composition.

In yet another embodiment, a composition that repels, reduces, and/or removes fungal pathogens includes fengycin in a carrier, wherein the composition is formulated for topical administration.

In yet another embodiment, a composition that repels, reduces, and/or removes fungal pathogens includes fengycin in a carrier, wherein the composition is formulated for use in medicine.

In yet another embodiment, a composition that repels, reduces, and/or removes fungal pathogens includes fengycin in a carrier, wherein the composition is formulated for use in a method of preventing, removing, reducing, or treating a bacterial or fungal infection.

In yet another embodiment, a composition that repels, reduces, and/or removes fungal pathogens includes fengycin in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes fengycin in a carrier, wherein the composition is formulated for use in a method of preventing, removing, reducing, or treating a bacterial, yeast, or fungal infection.

In yet another embodiment, a composition that repels, reduces, and/or removes fungal pathogens includes fengycin in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes fengycin in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes fengycin in a carrier, wherein the carrier is suitable for topical application to skin or a mucous membrane of a mammal.

In yet another embodiment, a composition that repels, reduces, and/or removes fungal pathogens includes fengycin in a carrier, wherein the composition can include from about 1% to about 75% emu oil by weight.

In yet another embodiment, a composition that repels, reduces, and/or removes fungal pathogens includes fengycin in a carrier, further including an effective amount of a fructooligosaccharide.

In yet another embodiment, a composition that repels, reduces, and/or removes fungal pathogens includes fengycin in a carrier, further including an effective amount of a fructooligosaccharide, wherein the fructooligosaccharide is present in an amount of from about 10 to about 1000 milligrams per gram of composition.

In yet another embodiment, a composition that repels, reduces, and/or removes fungal pathogens includes fengycin in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes fungal pathogens includes fengycin in a carrier, further including an effective amount of a fructooligosaccharide, wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria.

In yet another embodiment, a composition that repels, reduces, and/or removes fungal pathogens includes fengycin in a carrier, wherein the fengycin is obtained from a culture containing a probiotic bacteria, further wherein the composition is formulated for use as an anti-fungal composition.

In yet another embodiment, a composition that repels, reduces, and/or removes fungal pathogens includes fengycin in a carrier, wherein the fengycin is obtained from a culture containing a probiotic bacteria, further wherein the composition is formulated for use as a cream, gel, or spray.

In yet another embodiment, a composition that repels, reduces, and/or removes fungal pathogens includes fengycin in a carrier, wherein the fengycin is obtained from a culture containing a probiotic bacteria, further wherein the composition is a pharmaceutical composition.

In yet another embodiment, a composition that repels, reduces, and/or removes fungal pathogens includes fengycin in a carrier, wherein the fengycin is obtained from a culture containing a probiotic bacteria, further wherein the composition is formulated for topical administration.

In yet another embodiment, a composition that repels, reduces, and/or removes fungal pathogens includes fengycin in a carrier, wherein the fengycin is obtained from a culture containing a probiotic bacteria, further wherein the composition is formulated for use in medicine.

In yet another embodiment, a composition that repels, reduces, and/or removes fungal pathogens includes fengycin in a carrier, wherein the fengycin is obtained from a culture containing a probiotic bacteria, further wherein the composition is formulated for use in a method of preventing, removing, reducing, or treating a bacterial or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is cultured under aerobic conditions.

In yet another embodiment, a composition that repels, reduces, and/or removes fungal pathogens includes fengycin in a carrier, wherein the fengycin is obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes fungal pathogens includes fengycin in a carrier, wherein the fengycin is obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes fengycin in a carrier, wherein the fengycin is obtained from a culture containing a probiotic bacteria, further wherein the carrier is suitable for topical application to skin or a mucous membrane of a mammal.

In yet another embodiment, a composition that repels, reduces, and/or removes fungal pathogens includes fengycin in a carrier, wherein the fengycin is obtained from a culture containing a probiotic bacteria, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the carrier includes an effective amount of a fructooligosaccharide.

In yet another embodiment, a composition that repels, reduces, and/or removes fungal pathogens includes fengycin in a carrier, wherein the fengycin is obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is included in the composition in the form of spores.

In yet another embodiment, a composition that repels, reduces, and/or removes fungal pathogens includes fengycin in a carrier, wherein the fengycin is obtained from a culture containing a probiotic bacteria, further wherein the probiotic bacteria is included in the composition in the form of a dried cell mass.

In yet another embodiment, a composition that repels, reduces, and/or removes fungal pathogens includes fengycin in a carrier, wherein the fengycin is obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the extracellular product is fengycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria, further wherein the extracellular product is fengycin.

In yet another embodiment, a composition that repels, reduces, and/or removes fungal pathogens includes fengycin in a carrier, wherein the carrier includes substantially no intact probiotic bacteria, lysed bacteria, or bacterial fragments.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes fengycin in a carrier, wherein the fengycin is obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is fengycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is a supernatant or filtrate of a culture of the probiotic bacteria, further wherein the extracellular product is fengycin.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the composition is formulated for use as an anti-fungal composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the composition is formulated for topical administration.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is fengycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is a supernatant or filtrate of a culture of the probiotic bacteria, further wherein the extracellular product is fengycin.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes fengycin in a carrier, wherein the fengycin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is fengycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria, further wherein the extracellular product is fengycin.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the composition is formulated for use as an anti-fungal composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the composition is formulated for use in a method of preventing, removing reducing, or treating a bacterial or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the probiotic bacteria is included in the composition in the form of spores.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is fengycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria, further wherein the extracellular product is fengycin.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes fengycin in a carrier, wherein the fengycin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is fengycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of a probiotic bacteria, further wherein the extracellular product is fengycin.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the composition is formulated for use as an anti-fungal composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is fengycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria, further wherein the extracellular product is fengycin.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes fengycin in a carrier, wherein the fengycin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is fengycin.

In yet another embodiment, a composition that repels, reduces, and/or removes fungal pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of a probiotic bacteria, further wherein the extracellular product is fengycin.

In yet another embodiment, a composition that repels, reduces, and/or removes fungal pathogens includes iturin, bacillomycin, and/or fengycin in a carrier.

In yet another embodiment, a composition that repels, reduces, and/or removes fungal pathogens includes iturin, bacillomycin, and/or fengycin in a carrier, wherein the composition is formulated for use as an anti-fungal composition.

In yet another embodiment, a composition that repels, reduces, and/or removes fungal pathogens includes iturin, bacillomycin, and/or fengycin in a carrier, wherein the composition is formulated for use as a cream, gel, or spray.

In yet another embodiment, a composition that repels, reduces, and/or removes fungal pathogens includes iturin, bacillomycin, and/or fengycin in a carrier, wherein the composition is a pharmaceutical composition.

In yet another embodiment, a composition that repels, reduces, and/or removes fungal pathogens includes iturin, bacillomycin, and/or fengycin in a carrier, wherein the composition is formulated for topical administration.

In yet another embodiment, a composition that repels, reduces, and/or removes fungal pathogens includes iturin, bacillomycin, and/or fengycin in a carrier, wherein the composition is formulated for use in medicine.

In yet another embodiment, a composition that repels, reduces, and/or removes fungal pathogens includes iturin, bacillomycin, and/or fengycin in a carrier, wherein the composition is formulated for use in a method of preventing, removing, reducing, or treating a bacterial or fungal infection.

In yet another embodiment, a composition that repels, reduces, and/or removes fungal pathogens includes iturin, bacillomycin, and/or fengycin in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the composition is formulated for use in a method of preventing, removing, reducing, or treating a bacterial, yeast, or fungal infection.

In yet another embodiment, a composition that repels, reduces, and/or removes fungal pathogens includes iturin, bacillomycin, and/or fengycin in a carrier, wherein the composition is formulated for use in a method of preventing, removing, reducing, a treating a bacterial, yeast, or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin, bacillomycin, and/or fengycin in a carrier, wherein the carrier is suitable for topical application to skin or a mucous membrane of a mammal.

In yet another embodiment, a composition that repels, reduces, and/or removes fungal pathogens includes iturin, bacillomycin, and/or fengycin in a carrier, wherein the composition can include from about 1% to about 75% emu oil by weight.

In yet another embodiment, a composition that repels, reduces, and/or removes fungal pathogens includes iturin, bacillomycin, and/or fengycin in a carrier, further including an effective amount of a fructooligosaccharide.

In yet another embodiment, a composition that repels, reduces, and/or removes fungal pathogens includes iturin, bacillomycin, and/or fengycin in a carrier, further including an effective amount of a fructooligosaccharide, wherein the fructooligosaccharide is present in an amount of from about 10 to about 1000 milligrams per gram of composition.

In yet another embodiment, a composition that repels, reduces, and/or removes fungal pathogens includes iturin, bacillomycin, and/or fengycin in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes fungal pathogens includes iturin, bacillomycin, and/or fengycin in a carrier, further including an effective amount of a fructooligosaccharide, wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the composition is formulated for use as an anti-fungal composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the composition is formulated for use as a cream, gel, or spray.

Is yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the composition is a pharmaceutical composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the composition is formulated for topical administration.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the composition is formulated for use in medicine.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the composition is formulated for use in a method of preventing, removing, reducing, or treating a bacterial or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is cultured under aerobic conditions.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin, bacillomycin, and/or fengycin in a carrier, wherein the iturin, wherein the carrier is suitable for topical application to skin or a mucous membrane of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes an effective amount of a fructooligosaccharide.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is included in the composition in the form of spores.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is included in the composition in the form of a dried cell mass.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the one or more extracellular products are iturin, bacillomycin, and/or fengycin.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein one or more extracellular products are supernatant (s) or filtrate(s) of a culture of the probiotic bacteria, further wherein the one or more extracellular products are iturin, bacillomycin, and/or fengycin.

In yet another embodiment, a composition that repels, reduces, and/or removes fungal pathogens includes iturin, bacillomycin, and/or fengycin in a carrier, wherein the carrier includes substantially no intact probiotic bacteria, lysed bacteria, or bacterial fragments.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin, bacillomycin, and/or fengycin in a carrier, wherein the iturin, wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or a bacterial fragments, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin, bacillomycin, and/or fengycin in a carrier, wherein the iturin, wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the one or more extracellular products are iturin, bacillomycin, and/or fengycin.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the one or more extracellular products are supernatant(s) or filtrate(s) of a culture of the probiotic bacteria, further wherein the one or more extracellular products are iturin, bacillomycin, and/or fengycin.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the composition is formulated for use as an anti-fungal composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the composition is formulated for topical administration.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes fungal pathogens includes iturin, bacillomycin, and/or fengycin in a carrier, wherein the iturin, bacillomycin, and/or fengycin is obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is a *Bacillus* spp. bacteria, further wherein the one or more extracellular products are iturin, bacillomycin, and/or fengycin.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is a *Bacillus* spp. bacteria, further wherein the one or more extracellular products are supernatant(s) or filtrate(s) of a culture of the probiotic bacteria, further wherein the one or more extracellular products are iturin, bacillomycin, and/or fengycin.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the one or more extracellular products are iturin, bacillomycin, and/or fengycin.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the one or more extracellular products are supernatant(s) or filtrate(s) of a culture of the probiotic bacteria, further wherein the one or more extracellular products are iturin, bacillomycin, and/or fengycin.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the composition is formulated for use as an antifungal composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the probiotic bacteria is included in the composition in the form of spores.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is a strain of *Bacillus subtilis*, further wherein the one or more extracellular products are iturin, bacillomycin, and/or fengycin.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is a strain of *Bacillus subtilis*, further wherein the one or more extracellular products are supernatant(s) or filtrate(s) of a culture of the probiotic bacteria, further wherein the one or more extracellular products are iturin, bacillomycin, and/or fengycin.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an antifungal composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes iturin, bacillomycin, and/or fengyin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the one or more extracellular products are iturin, bacillomycin, and/or fengycin.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the one or more extracellular products are supernatant(s) or filtrate(s) of a culture of a probiotic bacteria, further wherein the one or more extracellular products are iturin, bacillomycin, and/or fengycin.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the composition is formulated for use as an anti-fungal composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes fungal pathogens includes iturin, bacillomycin, and/or fengycin in a carrier, wherein the iturin, wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin, bacillomycin, and/or fengycin in a carrier, wherein the iturin, wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is *Bacillus subtilis* DE111, further wherein the one or more extracellular products are iturin, bacillomycin, and/or fengycin.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is *Bacillus subtilis* DE111, further wherein the one or more extracellular products are supernatant(s) or filtrate(s) of a culture of the probiotic bacteria, further wherein the one or more extracellular products are iturin, bacillomycin, and/or fengycin.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-fungal composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes fungal pathogens includes iturin, bacillomycin, and/or fengycin in a carrier, wherein the iturin, wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the ituriin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 7% emu oil by weight.

In yet another embodiment, a composition that repels, reduces, and/or removes fungal pathogens includes iturin, bacillomycin, and/or fengycin in a carrier, wherein the iturin, wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes fungal pathogens includes iturin, bacillomycin, and/or fengycin in an carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes fungal pathogens includes iturin, bacillomycin, and/or fengycin in a carrier, wherein the iturin, bacillomycin, and/or fengycin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the one or more extracellular products are iturin, bacillomycin, and/or fengycin.

In yet another embodiment, a composition that repels, reduces, and/or removes fungal pathogens includes one or more extracellular products of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the one or more extracellular products are supernatant(s) or filtrate(s) of a culture of a probiotic bacteria, further wherein the one or more extracellular products are iturin, bacillomycin, and/or fengycin.

In an embodiment, a composition that transports iron across cell membranes includes secreted material in a carrier.

In another embodiment, a composition that transports iron across cell membranes includes secreted material in a carrier, wherein the composition is formulated for use as an anti-fungal composition.

In yet another embodiment, a composition that transports iron across cell membranes includes secreted material in a carrier, wherein the composition is formulated for use as an anti-bacterial composition.

In yet another embodiment, a composition that transports iron across cell membranes includes secreted material in a carrier, wherein the composition is formulated for use as a cream, gel, or spray.

In yet another embodiment, a composition that transports iron across cell membranes includes secreted material in a carrier, wherein the composition is a pharmaceutical composition.

In yet another embodiment, a composition that transports iron across cell membranes includes secreted material in a carrier, wherein the composition is formulated for topical administration.

In yet another embodiment, a composition that transports iron across cell membranes includes secreted material in a carrier, wherein the composition is formulated for use in medicine.

In yet another embodiment, a composition that transports iron across cell membranes includes secreted material in a carrier, wherein the composition is formulated for use in a method of preventing, removing, reducing, or treating a bacterial or fungal infection.

In yet another embodiment, a composition that transports iron across cell membranes includes secreted material in a carrier, wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes secreted material in a carrier, wherein the composition is formulated for use in a method of preventing, removing, reducing, or treating a bacterial, yeast, or fungal infection.

In yet another embodiment, a composition that transports iron across cell membranes includes secreted material in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes secreted material in a carrier, wherein the carrier is selected from the group consisting of an emulsion, cream, lotion, gel, oil, ointment, suspension, aerosol spray, powder, aerosol powder, and semi solid formulation.

In yet another embodiment, a composition that transports iron across cell membranes includes secreted material in a carrier, wherein the carrier is suitable for topical application to skin or a mucous membrane of a mammal.

In yet another embodiment, a composition that transports iron across cell membranes includes secreted material in a carrier, wherein the composition can include from about 1% to about 75% emu oil by weight.

In yet another embodiment, a composition that transports iron across cell membranes includes secreted material in a carrier, further including an effective amount of a fructooligosaccharide.

In yet another embodiment, a composition that transports iron across cell membranes includes secreted material in a carrier, further including an effective amount of a fructooligosaccharide, wherein the fructooligosaccharide is present in an amount of from about 10 to about 1000 milligrams per gram of composition.

In yet another embodiment, a composition that transports iron across cell membranes includes secreted material in a carrier, further including an effective amount of a fructooligosaccharide, wherein the fructooligosaccharide is present in an amount of from about 100 to about 500 milligrams per gram of composition.

In yet another embodiment, a composition that transports iron across cell membranes includes secreted material in a carrier, further including an effective amount of a fructooligosaccharide, wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria.

In yet another embodiment, a composition that transports iron across cell membranes includes secreted material in a carrier, wherein the carrier can include media obtained from a culture containing a probiotic bacteria, further wherein the composition is formulated for use as an anti-fungal composition.

In yet another embodiment, a composition that transports iron across cell membranes includes secreted material in a carrier, wherein the carrier can include media obtained from a culture containing a probiotic bacteria, further wherein the composition is formulated for use as an anti-bacterial composition.

In yet another embodiment, a composition that transports iron across cell membranes includes secreted material in a carrier, wherein the carrier can include media obtained from a culture containing a probiotic bacteria, further wherein the composition is formulated for use as a cream, gel, or spray.

In yet another embodiment, a composition that transports iron across cell membranes includes secreted material in a carrier, wherein the carrier can include media obtained from a culture containing a probiotic bacteria, further wherein the composition is a pharmaceutical composition.

In yet another embodiment, a composition that transports iron across cell membranes includes secreted material in a carrier, wherein the carrier can include media obtained from a culture containing a probiotic bacteria, further wherein the composition is formulated for topical administration.

In yet another embodiment, a composition that transports iron across cell membranes includes secreted material in a carrier, wherein the carrier can include media obtained from a culture containing a probiotic bacteria, further wherein the composition is formulated for use in medicine.

In yet another embodiment, a composition that transports iron across cell membranes includes secreted material in a carrier, wherein the carrier can include media obtained from a culture containing a probiotic bacteria, further wherein the composition is formulated for use in a method of preventing, removing, reducing, or treating a bacterial or fungal infection.

In yet another embodiment, a composition that transports iron across cell membranes includes secreted material in a carrier, wherein the carrier can include media obtained from a culture containing a probiotic bacteria, further wherein the probiotic bacteria is cultured under aerobic conditions.

In yet another embodiment, a composition that transports iron across cell membranes includes secreted material in a carrier, wherein the carrier can include media obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the composition is formulated for use in a method of preventing, removing, reducing, or treating a bacterial, yeast, or fungal infection.

In yet another embodiment, a composition that transports iron across cell membranes includes secreted material in a carrier, wherein the carrier can include media obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes secreted material in a carrier, wherein the carrier can include media obtained from a culture containing a probiotic bacteria, further wherein the carrier is suitable for topical application to skin or a mucous membrane of a mammal.

In yet another embodiment, a composition that transports iron across cell membranes includes secreted material in a carrier, wherein the carrier can include media obtained from a culture containing a probiotic bacteria, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the carrier includes an effective amount of a fructooligosaccharide.

In yet another embodiment, a composition that transports iron across cell membranes includes secreted material in a carrier, wherein the carrier can include media obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes secreted material in a carrier, wherein the carrier can include media obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes secreted material in a carrier, wherein the carrier can include media obtained from a culture containing a probiotic bacteria, further wherein the carrier includes an effective amount of a fructooligosaccharide, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is included in the composition in the form of spores.

In yet another embodiment, a composition that transports iron across cell membranes includes secreted material in a carrier, wherein the carrier can include media obtained from a culture containing a probiotic bacteria, further wherein the probiotic bacteria is included in the composition in the form of a dried cell mass.

In yet another embodiment, a composition that transports iron across cell membranes includes secreted material in a carrier, wherein the carrier can include media obtained from a culture containing a probiotic bacteria, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal.

In yet another embodiment, a composition that transports iron across cell membranes includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria.

In yet another embodiment, a composition that transports iron across cell membranes includes secreted material in a carrier, wherein the carrier includes substantially no intact probiotic bacteria, lysed bacteria, or bacterial fragments.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use as an anti-fungal composition.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use as an anti-bacterial composition.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that transports iron across cell membranes includes secreted material in a carrier, wherein the carrier can include media obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments.

In yet another embodiment, a composition that transports iron across cell membranes includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the composition is formulated for use as an anti-fungal composition.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the composition is formulated for use as an anti-bacterial composition.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the composition is formulated for use as a cream, gel, or spray.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the composition is a pharmaceutical composition.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the composition is formulated for topical administration.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the composition is formulated for use in medicine.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the probiotic bacteria is cultured under aerobic conditions.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the probiotic bacteria is formulated for use in a method of preventing, removing, reducing, or treating a bacterial or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the probiotic bacteria is formulated for use in a method of preventing, removing, reducing, or treating a bacterial, yeast, or fungal infection.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the probiotic bacteria is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the probiotic bacteria is included in the composition in the form of spores.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a *Bacillus* spp. bacteria.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is a supernatant or filtrate of a culture of the probiotic bacteria.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-fungal composition.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-bacterial composition.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial yeast, or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that transports iron across cell membranes includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the composition is formulated for use as an antifungal composition.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the composition is formulated for use as an antibacterial composition.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the composition is formulated for use as a cream, gel, or spray.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the composition is a pharmaceutical composition.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the composition is formulated for topical administration.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the composition is formulated for use in medicine.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the probiotic bacteria is cultured under aerobic conditions.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the probiotic bacteria is included in the composition in the form of spores.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a strain of *Bacillus subtilis*.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an antifungal composition.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an antibacterial composition.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for topical administration.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that transports iron across cell membranes, includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that transports iron across cell membranes includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the composition is formulated for use as an anti-fungal composition.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the composition is formulated for use as an anti-bacterial composition.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the composition is formulated for use as a cream, gel, or spray.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the composition is a pharmaceutical composition.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the composition is formulated for topical administration.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the composition is formulated for use in medicine.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the probiotic bacteria is cultured under aerobic conditions.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the probiotic bacteria is included in the composition in the form of spores.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is *Bacillus subtilis* DE111.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-fungal composition.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-bacterial composition.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis DE*111, further wherein the carrier includes substantially no intact probiotic bacteria, lysed bacteria, or bacterial fragments, further wherein the composition is a pharmaceutical composition.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that transports iron across cell membranes includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that transports iron across cell membranes includes bacillibactin in a carrier.

In yet another embodiment, a composition that transports iron across cell membranes includes bacillibactin in a carrier, wherein the composition is formulated for use as an anti-fungal composition.

In yet another embodiment, a composition that transports iron across cell membranes includes bacillibactin in a carrier, wherein the composition is formulated for use as an anti-bacterial composition.

In yet another embodiment, a composition that transports iron across cell membranes includes bacillibactin in a carrier, wherein the composition is formulated for use as a cream, gel, or spray.

In yet another embodiment, a composition that transports iron across cell membranes includes bacillibactin in a carrier, wherein the composition is a pharmaceutical composition.

In yet another embodiment, a composition that transports iron across cell membranes includes bacillibactin in a carrier, wherein the composition is formulated for topical administration.

In yet another embodiment, a composition that transports iron across cell membranes includes bacillibactin in a carrier, wherein the composition is formulated for use in medicine.

In yet another embodiment, a composition that transports iron across cell membranes includes bacillibactin in a carrier, wherein the composition is formulated for use in a method of preventing, removing, reducing, or treating a bacterial or fungal infection.

In yet another embodiment, a composition that transports iron across cell membranes includes bacillibactin in a carrier, wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes bacillibactin in a carrier, wherein the composition is formulated for use in a method of preventing, removing, reducing, or treating a bacterial, yeast, or fungal infection.

In yet another embodiment, a composition that transports iron across cell membranes includes bacillibactin in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes bacillibactin in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes bacillibactin in a carrier, wherein the carrier is suitable for topical application to skin or a mucous membrane of a mammal.

In yet another embodiment, a composition that transports iron across cell membranes includes bacillibactin in a carrier, wherein the composition can include from about 1% to about 75% emu oil by weight.

In yet another embodiment, a composition that transports iron across cell membranes includes bacillibactin in a carrier, further including an effective amount of a fructooligosaccharide.

In yet another embodiment, a composition that transports iron across cell membranes includes bacillibactin in a carrier, further including an effective amount of a fructooligosaccharide, wherein the fructooligosaccharide is present in an amount of from about 10 to about 1000 milligrams per gram of composition.

In yet another embodiment, a composition that transports iron across cell membranes includes bacillibactin in a carrier, further including an effective amount of a fructooligosaccharide, wherein the fructooligosaccharide is present in an amount of from about 100 to about 500 milligrams per gram of composition.

In yet another embodiment, a composition that transports iron across cell membranes includes bacillibactin in a carrier, further including an effective amount of a fructooligosaccharide, wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria.

In yet another embodiment, a composition that transports iron across cell membranes includes bacillibactin in a carrier, wherein the bacillibactin is obtained from a culture containing a probiotic bacteria, further wherein the composition is formulated for use as an anti-fungal composition.

In yet another embodiment, a composition that transports iron across cell membranes includes bacillibactin in a carrier, wherein the bacillibactin is obtained from a culture containing a probiotic bacteria, further wherein the composition is formulated for use as an anti-bacterial composition.

In yet another embodiment, a composition that transports iron across cell membranes includes bacillibactin in a carrier, wherein the bacillibactin is obtained from a culture containing a probiotic bacteria, further wherein the composition is formulated for use as a cream, gel, or spray.

In yet another embodiment, a composition that transports iron across cell membranes includes bacillibactin in a carrier, wherein the bacillibactin is obtained from a culture containing a probiotic bacteria, further wherein the composition is a pharmaceutical composition.

In yet another embodiment, a composition that transports iron across cell membranes includes bacillibactin in a carrier, wherein the bacillibactin is obtained from a culture containing a probiotic bacteria, further wherein the composition is formulated for topical administration.

In yet another embodiment, a composition that transports iron across cell membranes includes bacillibactin in a carrier, wherein the bacillibactin is obtained from a culture containing a probiotic bacteria, further wherein the composition is formulated for use in medicine.

In yet another embodiment, a composition that transports iron across cell membranes includes bacillibactin in a carrier, wherein the bacillibactin is obtained from a culture containing a probiotic bacteria, further wherein the composition is formulated for use in a method of preventing, removing, reducing, or treating a bacterial or fungal infection.

In yet another embodiment, a composition that transports iron across cell membranes includes bacillibactin in a carrier, wherein the bacillibactin is obtained from a culture containing a probiotic bacteria, further wherein the probiotic bacteria is cultured under aerobic conditions.

In yet another embodiment, a composition that transports iron across cell membranes includes bacillibactin in a carrier, wherein the bacillibactin is obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the composition is formulated for use in a method of preventing, removing, reducing, or treating a bacterial, yeast, or fungal infection.

In yet another embodiment, a composition that transports iron across cell membranes includes bacillibactin in a carrier, wherein the bacillibactin is obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes bacillibactin in a carrier, wherein the bacillibactin is obtained from a culture containing a probiotic bacteria, further wherein the carrier is suitable for topical administration to skin or a mucous membrane of a mammal.

In yet another embodiment, a composition that transports iron across cell membranes includes bacillibactin in a carrier, wherein the bacillibactin is obtained from a culture containing a probiotic bacteria, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the carrier includes an effective amount of a fructooligosaccharide.

In yet another embodiment, a composition that transports iron across cell membranes includes bacillibactin in a carrier, wherein the bacillibactin is obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes bacillibactin in a carrier, wherein the bacillibactin is obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes bacillibactin in a carrier, wherein the bacillibactin is obtained from a culture containing a probiotic bacteria, further wherein the carrier includes an effective amount of a fructooligosaccharide, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is included in the composition in the form of spores.

In yet another embodiment, a composition that transports iron across cell membranes includes bacillibactin in a carrier, wherein the bacillibactin is obtained from a culture containing a probiotic bacteria, further wherein the probiotic bacteria is included in the composition in the form of a dried cell mass.

In yet another embodiment, a composition that transports iron across cell membranes includes bacillibactin in a carrier, wherein the bacillibactin is obtained from a culture containing a probiotic bacteria, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the extracellular product is bacillibactin.

In yet another embodiment, a composition that transports iron across cell membranes includes an extracellular product a probiotic bacteria in a pharmaceutically acceptable carrier suitable for topical administration to skin or a mucous membrane of a mammal, wherein the extracellular product is a supernatant or filtrate of culture of the probiotic bacteria, further wherein the extracellular product is bacillibactin.

In yet another embodiment, a composition that transports iron across cell membranes includes bacillibactin in a carrier, wherein the carrier includes substantially no intact probiotic bacteria, lysed bacteria, or bacterial fragments.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the composition is formulated for use as an anti-fungal composition.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the composition is formulated for use as an anti-bacterial composition.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacteria fragments, further wherein the composition is formulated for topical administration.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lsyed bacteria, or bacterial fragments, further wherein the carrier includes an effective amount of a fructooligosaccharide, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that transports iron across cell membranes includes bacillibactin in a carrier, wherein the bacillibactin is obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is bacillibactin.

In yet another embodiment, a composition that transports iron across cell membranes includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillibactin.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the composition is formulated for use as an anti-fungal composition.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the composition is formulated for use as an anti-bacterial composition.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the composition is formulated for use as a cream, gel, or spray.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the composition is a pharmaceutical composition.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the composition is formulated for topical administration.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the composition is formulated for use in medicine.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the probiotic bacteria is cultured under aerobic conditions.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the composition is formulated for use in a method of preventing, removing, reducing or treating a bacterial, yeast, or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the probiotic bacteria is included in the composition in the form of spores.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is bacillibactin.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is a supernatant or filtrate of a culture of the probiotic bacteria, further wherein the extracellular product is bacillibactin.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-fungal composition.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-bacterial composition.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that transports iron across cell membranes includes bacillibactin in a carrier, wherein the bacillibactin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is bacillibactin.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillibactin.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition is formulated for use as an anti-fungal composition.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition is formulated for use as an anti-bacterial composition.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition is formulated for use as a cream, gel, or spray.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition is a pharmaceutical composition.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition is formulated for topical administration.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition is formulated for use in medicine.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the probiotic bacteria is cultured under aerobic conditions.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subitlis*, further wherein the carrier includes an effective amount of a fructooligosaccharide, further wherein the fructooligosacharide is present in an amount of from about 100 to about 500 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the probiotic bacteria is included in the composition in the form of spores.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is bacillibactin.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria, further wherein the extracellular product is bacillibactin.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an anti-fungal composition.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an anti-bacterial composition.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that transports iron across cell membranes includes bacillibactin in a carrier, wherein the bacillibactin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is bacillibactin.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillibactin.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the composition is formulated for use as an anti-fungal composition.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the composition is formulated for use as an anti-bacterial composition.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the composition is formulated for use as a cream, gel, or spray.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the composition is a pharmaceutical composition.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the composition is formulated for topical administration.

In yet another embodiment, composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the composition is formulated for use in medicine.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the probiotic bacteria is cultured under aerobic conditions.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes an effective amount of a fructooligosaccharide.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the probiotic bacteria is included in the composition in the form of spores.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is bacillibactin.

In yet another embodiment, a composition that transports iron across cell membranes includes an extracellular product of a probiotic bacteria is a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria, further wherein the extracellular product is bacillibactin.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-fungal composition.

In yet another embodiment, a composition that transports iron across cell membranes includes bacillibactin in a carrier, wherein the bacillibactin is obtained from a culture containing a probiotic bacteria, further wherein probiotic bacteria is *Bacillus subtilis* DE111, further wherein the carrier includes substantially no intact probiotic bacteria, lysed bacteria, or bacterial fragments, further wherein the composition is formulated for use as an anti-bacterial composition.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that transports iron across cell membranes includes bacillibactin in a carrier, wherein the bacillibactin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is bacillibactin.

In yet another embodiment, a composition that transports iron across cell membranes includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillibactin.

In an embodiment, a composition that repels, reduces, and/or removes bacterial pathogens includes secreted material in a carrier.

In another embodiment, a composition that repels, reduces, and/or removes bacterial pathogens includes secreted material in a carrier, wherein the composition is formulated for use as an anti-bacterial composition.

In yet another embodiment, a composition that repels, reduces, and/or removes bacterial pathogens includes secreted material in a carrier, wherein the composition is formulated for use as a cream, gel, or spray.

In yet another embodiment, a composition that repels, reduces, and/or removes bacterial pathogens includes secreted material in a carrier, wherein the composition is a pharmaceutical composition.

In yet another embodiment, a composition that repels, reduces, and/or removes bacterial pathogens includes secreted material in a carrier, wherein the composition is formulated for topical administration.

In yet another embodiment, a composition that repels, reduces, and/or removes bacterial pathogens includes secreted material in a carrier, wherein the composition is formulated for use in medicine.

In yet another embodiment, a composition that repels, reduces, and/or removes bacterial pathogens includes secreted material in a carrier, wherein the composition is formulated for use in a method of preventing, removing, reducing, or treating a bacterial or fungal infection.

In yet another embodiment, a composition that repels, reduces, and/or removes bacterial pathogens includes secreted material in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes secreted material in a carrier, wherein the composition is formulated for use in a method of preventing, removing, reducing, or treating a bacterial, yeast, or fungal infection.

In yet another embodiment, a composition that repels, reduces, and/or removes bacterial pathogens includes secreted material in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes secreted material in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes secreted material in a carrier, wherein the carrier is suitable for topical application to skin or a mucous membrane of a mammal.

In yet another embodiment, a composition that repels, reduces, and/or removes bacterial pathogens includes secreted material in a carrier, wherein the composition can include from about 1% to about 75% emu oil by weight.

In yet another embodiment, a composition that repels, reduces, and/or removes bacterial pathogens includes secreted material in a carrier, further including an effective amount of a fructooligosaccharide.

In yet another embodiment, a composition that repels, reduces, and/or removes bacterial pathogens includes secreted material in a carrier, further including an effective amount of a fructooligosaccharide, wherein the fructooligosaccharide is present in an amount of from about 10 to about 1000 milligrams per gram of composition.

In yet another embodiment, a composition that repels, reduces, and/or removes bacterial pathogens includes secreted material in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes bacterial pathogens includes secreted material in a carrier, further including an effective amount of a fructooligosaccharide, wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria.

In yet another embodiment, a composition that repels, reduces, and/or removes bacterial pathogens includes secreted material in a carrier, wherein the carrier can include media obtained from a culture containing a probiotic bacteria, further wherein the composition is formulated for use as an anti-bacterial composition.

In yet another embodiment, a composition that repels, reduces, and/or removes bacterial pathogens includes secreted material in a carrier, wherein the carrier can include media obtained from a culture containing a probiotic bacteria, further wherein the composition is formulated for use as a cream, gel, or spray.

In yet another embodiment, a composition that repels, reduces, and/or removes bacterial pathogens includes secreted material in a carrier, wherein the carrier can include media obtained from a culture containing a probiotic bacteria, further wherein the composition is a pharmaceutical composition.

In yet another embodiment, a composition that repels, reduces, and/or removes bacterial pathogens includes secreted material in a carrier, wherein the carrier can include media obtained from a culture containing a probiotic bacteria, further wherein the composition is formulated for topical administration.

In yet another embodiment, a composition that repels, reduces, and/or removes bacterial pathogens includes secreted material in a carrier, wherein the carrier can include media obtained from a culture containing a probiotic bacteria, further wherein the composition is formulated for use in medicine.

In yet another embodiment, a composition that repels, reduces, and/or removes bacterial pathogens includes secreted material in a carrier, wherein the carrier can include media obtained from a culture containing a probiotic bacteria, further wherein the composition is formulated for use in a method of preventing, removing, reducing, or treating a bacterial or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is cultured under aerobic conditions.

In yet another embodiment, a composition that repels, reduces, and/or removes bacterial pathogens includes secreted material in a carrier, wherein the carrier can include media obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes bacterial pathogens includes secreted material in a carrier, wherein the carrier can include media obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes secreted material in a carrier, wherein the carrier can include media obtained from a culture containing a probiotic bacteria, further wherein the carrier is suitable for topical application to skin or a mucous membrane of a mammal.

In yet another embodiment, a composition that repels, reduces, and/or removes bacterial pathogens includes secreted material in a carrier, wherein the carrier can include media obtained from a culture containing a probiotic bacteria, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the carrier includes an effective amount of a fructooligosaccharide.

In yet another embodiment, a composition that repels, reduces, and/or removes bacterial pathogens includes secreted material in a carrier, wherein the carrier can include media obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is included in the composition in the form of spores.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is included in the composition in the form of a dried cell mass.

In yet another embodiment, a composition that repels, reduces, and/or removes bacterial pathogens includes secreted material in a carrier, wherein the carrier can include media obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria.

In yet another embodiment, a composition that repels, reduces, and/or removes bacterial pathogens includes secreted material in a carrier, wherein the carrier includes substantially no intact probiotic bacteria, lysed bacteria, or bacterial fragments.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes secreted material in a carrier, wherein the carrier can include media obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the composition is formulated for use as an anti-bacterial composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the composition is formulated for topical administration.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp.

bacteria, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is a supernatant or filtrate of a culture of the probiotic bacteria.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing or treating a bacterial, yeast, or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the composition is formulated for use as an anti-bacterial composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of

*Bacillus subtilis*, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the probiotic bacteria is included in the composition in the form of spores.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of Bacillus subtilis, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the composition is formulated for use as an anti-bacterial composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes secreted material in a carrier, wherein the carrier can include e media obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes secreted material in a carrier, wherein the carrier can include media obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of the probiotic bacteria.

In yet another embodiment, a composition that repels, reduces, and/or removes bacterial pathogens includes bacillysin in a carrier.

In yet another embodiment, a composition that repels, reduces, and/or removes bacterial pathogens includes bacillysin in a carrier, wherein the composition is formulated for use as an anti-bacterial composition.

In yet another embodiment, a composition that repels, reduces, and/or removes bacterial pathogens includes bacillysin in a carrier, wherein the composition is formulated for use as a cream, gel, or spray.

In yet another embodiment, a composition that repels, reduces, and/or removes bacterial pathogens includes bacillysin in a carrier, wherein the composition is a pharmaceutical composition.

In yet another embodiment, a composition that repels, reduces, and/or removes bacterial pathogens includes bacillysin in a carrier, wherein the composition is formulated for topical administration.

In yet another embodiment, a composition that repels, reduces, and/or removes bacterial pathogens includes bacillysin in a carrier, wherein the composition is formulated for use in medicine.

In yet another embodiment, a composition that repels, reduces, and/or removes bacterial pathogens includes bacillysin in a carrier, wherein the composition is formulated for use in a method of preventing, removing, reducing, or treating a bacterial or fungal infection.

In yet another embodiment, a composition that repels, reduces, and/or removes bacterial pathogens includes bacillysin in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin in a carrier, wherein the composition is formulated for use in a method of preventing, removing, reducing, or treating a bacterial, yeast, or fungal infection.

In yet another embodiment, a composition that repels, reduces, and/or removes bacterial pathogens includes bacillysin in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin in a carrier, wherein the carrier is suitable for topical application to skin or a mucous membrane of a mammal.

In yet another embodiment, a composition that repels, reduces, and/or removes bacterial pathogens includes bacillysin in a carrier, wherein the composition can include from about 1% to about 75% emu oil by weight.

In yet another embodiment, a composition that repels, reduces, and/or removes bacterial pathogens includes bacillysin in a carrier, further including an effective amount of a fructooligosaccharide.

In yet another embodiment, a composition that repels, reduces, and/or removes bacterial pathogens includes bacillysin in a carrier, further including an effective amount of a fructooligosaccharide, wherein the fructooligosaccharide is present in an amount of from about 10 to about 1000 milligrams per gram of composition.

In yet another embodiment, a composition that repels, reduces, and/or removes bacterial pathogens includes bacillysin in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes bacterial pathogens includes bacillysin in a carrier, further including an effective amount of a fructooligosaccharide, wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria.

In yet another embodiment, a composition that repels, reduces, and/or removes bacterial pathogens includes bacillysin in a carrier, wherein the bacillysin is obtained from a culture containing a probiotic bacteria, further wherein the composition is formulated for use as an anti-bacterial composition.

In yet another embodiment, a composition that repels, reduces, and/or removes bacterial pathogens includes bacillysin in a carrier, wherein the bacillysin is obtained from a culture containing a probiotic bacteria, further wherein the composition is formulated for use as a cream, gel, or spray.

In yet another embodiment, a composition that repels, reduces, and/or removes bacterial pathogens includes bacillysin in a carrier, wherein the bacillysin is obtained from a culture containing a probiotic bacteria, further wherein the composition is a pharmaceutical composition.

In yet another embodiment, a composition that repels, reduces, and/or removes bacterial pathogens includes bacillysin in a carrier, wherein the bacillysin is obtained from a culture containing a probiotic bacteria, further wherein the composition is formulated for topical administration.

In yet another embodiment, a composition that repels, reduces, and/or removes bacterial pathogens includes bacillysin in a carrier, wherein the bacillysin is obtained from a culture containing a probiotic bacteria, further wherein the composition is formulated for use in medicine.

In yet another embodiment, a composition that repels, reduces, and/or removes bacterial pathogens includes bacillysin in a carrier, wherein the bacillysin is obtained from a culture containing a probiotic bacteria, further wherein the composition is formulated for use in a method of preventing, removing, reducing, or treating a bacterial or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is cultured under aerobic conditions.

In yet another embodiment, a composition that repels, reduces, and/or removes bacterial pathogens includes bacillysin in a carrier, wherein the bacillysin is obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin in a carrier, wherein the bacillysin is obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin in a carrier, wherein the bacillysin is obtained from a culture containing a probiotic bacteria, further wherein the carrier is suitable for topical application to skin or a mucous membrane of a mammal.

In yet another embodiment, a composition that repels, reduces, and/or removes bacterial pathogens includes bacillysin in a carrier, wherein the bacillysin is obtained from a culture containing a probiotic bacteria, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the carrier includes an effective amount of a fructooligosaccharide.

In yet another embodiment, a composition that repels, reduces, and/or removes bacterial pathogens includes bacillysin in a carrier, wherein the bacillysin is obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is included in the composition in the form of spores.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is included in the composition in the form of a dried cell mass.

In yet another embodiment, a composition that repels, reduces, and/or removes bacterial pathogens includes bacillysin in a carrier, wherein the bacillysin is obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the extracellular product is bacillysin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria, further wherein the extracellular product is bacillysin.

In yet another embodiment, a composition that repels, reduces, and/or removes bacterial pathogens includes bacillysin in a carrier, wherein the bacillysin includes substantially no intact probiotic bacteria, lysed bacteria, or bacterial fragments.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the composition is formulated for use as an antibacterial composition.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes bacillysin in a carrier, wherein the bacillysin is obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is bacillysin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillysin.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the composition is formulated for use as an anti-bacterial composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical application to skin or a mucous membrane of a mammal, wherein the probiotic bacteria is a *Bacillus* spp. bacteria, further wherein the extracellular product is bacillysin.

In yet another embodiment, a composition that repels, reduces, and/or removes bacterial pathogens includes an extracellular product of a probiotic bacteria in a pharmaceutically acceptable carrier suitable for topical application to skin or a mucous membrane of a mammal, wherein the probiotic bacteria is a *Bacillus* spp. bacteria, further wherein the extracellular product is a supernatant or filtrate of a culture of the probiotic bacteria, further wherein the extracellular product is bacillysin.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing a probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is bacillysin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillysin.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the composition is formulated for use as an anti-bacterial composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the probiotic bacteria is included in the composition in the form of spores.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is bacillysin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria, further wherein the extracellular product is bacillysin.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is bacillysin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillysin.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the composition is formulated for use as an anti-bacterial composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is bacillysin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria, further wherein the extracellular product is bacillysin.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes bacillysin in a carrier, wherein the bacillysin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is bacillysin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of the probiotic bacteria, further wherein the extracellular product is bacillysin.

In yet another embodiment, a composition that repels, reduces, and/or removes bacterial pathogens includes subtilosin in a carrier.

In yet another embodiment, a composition that repels, reduces, and/or removes bacterial pathogens includes subtilosin in a carrier, wherein the composition is formulated for use as an anti-bacterial composition.

In yet another embodiment, a composition that repels, reduces, and/or removes bacterial pathogens includes subtilosin in a carrier, wherein the composition is formulated for use as a cream, gel, or spray.

In yet another embodiment, a composition that repels, reduces, and/or removes bacterial pathogens includes subtilosin in a carrier, wherein the composition is a pharmaceutical composition.

In yet another embodiment, a composition that repels, reduces, and/or removes bacterial pathogens includes subtilosin in a carrier, wherein the composition is formulated for topical administration.

In yet another embodiment, a composition that repels, reduces, and/or removes bacterial pathogens includes subtilosin in a carrier, wherein the composition is formulated for use in medicine.

In yet another embodiment, a composition that repels, reduces, and/or removes bacterial pathogens includes subtilosin in a carrier, wherein the composition is formulated for use in a method of preventing, removing, reducing, or treating a bacterial or fungal infection.

In yet another embodiment, a composition that repels, reduces, and/or removes bacterial pathogens includes subtilosin in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes subtilosin in a carrier, wherein the composition is formulated for use in a method of preventing, removing, reducing, or treating a bacterial, yeast, or fungal infection.

In yet another embodiment, a composition that repels, reduces, and/or removes bacterial pathogens includes subtilosin in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes subtilosin in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes subtilosin in a carrier, wherein the carrier is suitable for topical application to skin or a mucous membrane of a mammal.

In yet another embodiment, a composition that repels, reduces, and/or removes bacterial pathogens includes subtilosin in a carrier, wherein the composition can include from about 1% to about 75% emu oil by weight.

In yet another embodiment, a composition that repels, reduces, and/or removes bacterial pathogens includes subtilosin in a carrier, further including an effective amount of a fructooligosaccharide.

In yet another embodiment, a composition that repels, reduces, and/or removes bacterial pathogens includes subtilosin in a carrier, further including an effective amount of a fructooligosaccharide, wherein the fructooligosaccharide is present in an amount of from about 10 to about 1000 milligrams per gram of composition.

In yet another embodiment, a composition that repels, reduces, and/or removes bacterial pathogens includes subtilosin in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes bacterial pathogens includes subtilosin in a carrier, further including an effective amount of a fructooligosaccharide, wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria.

In yet another embodiment, a composition that repels, reduces, and/or removes bacterial pathogens includes subtilosin in a carrier, wherein the subtilosin is obtained from a culture containing a probiotic bacteria, further wherein the composition is formulated for use as an anti-bacterial composition.

In yet another embodiment, a composition that repels, reduces, and/or removes bacterial pathogens includes subtilosin in a carrier, wherein the subtilosin is obtained from a culture containing a probiotic bacteria, further wherein the composition is formulated for use as a cream, gel, or spray.

In yet another embodiment, a composition that repels, reduces, and/or removes bacterial pathogens includes subtilosin in a carrier, wherein the subtilosin is obtained from a culture containing a probiotic bacteria, further wherein the composition is a pharmaceutical composition.

In yet another embodiment, a composition that repels, reduces, and/or removes bacterial pathogens includes subtilosin in a carrier, wherein the subtilosin is obtained from a culture containing a probiotic bacteria, further wherein the composition is formulated for topical administration.

In yet another embodiment, a composition that repels, reduces, and/or removes bacterial pathogens includes subtilosin in a carrier, wherein the subtilosin is obtained from a culture containing a probiotic bacteria, further wherein the composition is formulated for use in medicine.

In yet another embodiment, a composition that repels, reduces, and/or removes bacterial pathogens includes subtilosin in a carrier, wherein the subtilosin is obtained from a culture containing a probiotic bacteria, further wherein the composition is formulated for use in a method of preventing, removing, reducing, or treating a bacterial or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is cultured under aerobic conditions.

In yet another embodiment, a composition that repels, reduces, and/or removes bacterial pathogens includes subtilosin in a carrier, wherein the subtilosin is obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes bacterial pathogens includes subtilosin in a carrier, wherein the subtilosin is obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes subtilosin in a carrier, wherein the subtilosin is obtained from a culture containing a probiotic bacteria, further wherein the carrier is suitable for topical application to skin or a mucous membrane of a mammal.

In yet another embodiment, a composition that repels, reduces, and/or removes bacterial pathogens includes subtilosin in a carrier, wherein the subtilosin is obtained from a culture containing a probiotic bacteria, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the carrier includes an effective amount of a fructooligosaccharide.

In yet another embodiment, a composition that repels, reduces, and/or removes bacterial pathogens includes subtilosin in a carrier, wherein the subtilosin is obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is included in the composition in the form of spores.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is included in the composition in the form of a dried cell mass.

In yet another embodiment, a composition that repels, reduces, and/or removes bacterial pathogens includes subtilosin in a carrier, wherein the subtilosin is obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the extracellular product is subtilosin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria, further wherein the extracellular product is subtilosin.

In yet another embodiment, a composition that repels, reduces, and/or removes bacterial pathogens includes subtilosin in a carrier, wherein the carrier includes substantially no intact probiotic bacteria, lysed bacteria, or bacterial fragments.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is cultured under aerobic conditions.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes subtilosin in a carrier, wherein the subtilosin is obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is subtilosin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is a supernatant or filtrate of a culture of the probiotic bacteria, further wherein the extracellular product is subtilosin.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the composition is formulated for use as an anti-bacterial composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the composition is formulated for topical administration.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is subtilosin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is a supernatant or filtrate of a culture of the probiotic bacteria, further wherein the extracellular product is subtilosin.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is subtilosin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria, further wherein the extracellular product is subtilosin.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the composition is formulated for use as an antibacterial composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes bacterial pathogens include subtilosin in a carrier, wherein the subtilosin is obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes bacterial pathogens include subtilosin in a carrier, wherein the subtilosin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the probiotic bacteria is included in the composition in the form of spores.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is subtilosin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria, further wherein the extracellular product is subtilosin.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an antibacterial composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier include substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is subtilosin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of the probiotic bacteria, further wherein the extracellular product is subtilosin.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the composition is formulated for use as an anti-bacterial composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further where the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the culture containing a probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is subtilosin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria, further wherein the extracellular product is subtilosin.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes subtilosin in a carrier, wherein the subtilosin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is subtilosin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of the probiotic bacteria, further wherein the extracellular product is subtilosin.

In yet another embodiment, a composition that repels, reduces, and/or removes bacterial pathogens includes sublancin in a carrier.

In yet another embodiment, a composition that repels, reduces, and/or removes bacterial pathogens includes sublancin in a carrier, wherein the composition is formulated for use as an anti-bacterial composition.

In yet another embodiment, a composition that repels, reduces, and/or removes bacterial pathogens includes sublancin in a carrier, wherein the composition is formulated for use as a cream, gel, or spray.

In yet another embodiment, a composition that repels, reduces, and/or removes bacterial pathogens includes sublancin in a carrier, wherein the composition is a pharmaceutical composition.

In yet another embodiment, a composition that repels, reduces, and/or removes bacterial pathogens includes sublancin in a carrier, wherein the composition is formulated for topical administration.

In yet another embodiment, a composition that repels, reduces, and/or removes bacterial pathogens includes sublancin in a carrier, wherein the composition is formulated for use in medicine.

In yet another embodiment, a composition that repels, reduces, and/or removes bacterial pathogens includes sublancin in a carrier, wherein the composition is formulated for use in a method of preventing, removing, reducing, or treating a bacterial or fungal infection.

In yet another embodiment, a composition that repels, reduces, and/or removes bacterial pathogens includes sublancin in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes sublancin in a carrier, wherein the composition is formulated for use in a method of preventing, removing, reducing, or treating a bacterial, yeast, or fungal infection.

In yet another embodiment, a composition that repels, reduces, and/or removes bacterial pathogens includes sublancin in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes sublancin in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes sublancin in a carrier, wherein the carrier is suitable for topical application to skin or a mucous membrane of a mammal.

In yet another embodiment, a composition that repels, reduces, and/or removes bacterial pathogens includes sublancin in a carrier, wherein the composition can include from about 1% to about 75% emu oil by weight.

In yet another embodiment, a composition that repels, reduces, and/or removes bacterial pathogens includes sublancin in a carrier, further including an effective amount of a fructooligosaccharide.

In yet another embodiment, a composition that repels, reduces, and/or removes bacterial pathogens includes sublancin in a carrier, further including an effective amount of a fructooligosaccharide, wherein the fructooligosaccharide is present in an amount of from about 10 to about 1000 milligrams per gram of composition.

In yet another embodiment, a composition that repels, reduces, and/or removes bacterial pathogens includes sublancin in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes bacterial pathogens includes sublancin in a carrier, further including an effective amount of a fructooligosaccharide, wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria.

In yet another embodiment, a composition that repels, reduces, and/or removes bacterial pathogens includes sublancin in a carrier, wherein the sublancin is obtained from a culture containing a probiotic bacteria, further wherein the composition is formulated for use as an anti-bacterial composition.

In yet another embodiment, a composition that repels, reduces, and/or removes bacterial pathogens includes sublancin in a carrier, wherein the sublancin is obtained from a culture containing a probiotic bacteria, further wherein the composition is formulated for use as a cream, gel, or spray.

In yet another embodiment, a composition that repels, reduces, and/or removes bacterial pathogens includes sublancin in a carrier, wherein the sublancin is obtained from a culture containing a probiotic bacteria, further wherein the composition is a pharmaceutical composition.

In yet another embodiment, a composition that repels, reduces, and/or removes bacterial pathogens includes sublancin in a carrier, wherein the sublancin is obtained from a culture containing a probiotic bacteria, further wherein the composition is formulated for topical administration.

In yet another embodiment, a composition that repels, reduces, and/or removes bacterial pathogens includes sublancin in a carrier, wherein the sublancin is obtained from a culture containing a probiotic bacteria, further wherein the composition is formulated for use in medicine.

In yet another embodiment, a composition that repels, reduces, and/or removes bacterial pathogens includes sublancin in a carrier, wherein the sublancin is obtained from a culture containing a probiotic bacteria, further wherein the composition is formulated for use in a method of preventing, removing, reducing, or treating a bacterial or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is cultured under aerobic conditions.

In yet another embodiment, a composition that repels, reduces, and/or removes bacterial pathogens includes sublancin in a carrier, wherein the sublancin is obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes bacterial pathogens includes sublancin in a carrier, wherein the sublancin is obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes sublancin in a carrier, wherein the sublancin is obtained from a culture containing a probiotic bacteria, further wherein the carrier is suitable for topical administration to skin or a mucous membrane of a mammal.

In yet another embodiment, a composition that repels, reduces, and/or removes bacterial pathogens includes sublancin in a carrier, wherein the sublancin is obtained from a culture containing a probiotic bacteria, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the carrier includes an effective amount of a fructooligosaccharide.

In yet another embodiment, a composition that repels, reduces, and/or removes bacterial pathogens includes sublancin in a carrier, wherein the sublancin is obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is included in the composition in the form of spores.

In yet another embodiment, a composition that repels, reduces, and/or removes bacterial pathogens includes sublancin in a carrier, wherein the sublancin is obtained from a culture containing a probiotic bacteria, further wherein the probiotic bacteria is included in the composition in the form of a dried cell mass.

In yet another embodiment, a composition that repels, reduces, and/or removes bacterial pathogens includes sublancin in a carrier, further wherein the sublancin is obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the extracellular product is sublancin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the extracellular product is a supernatant or filtrate of a culture of the probiotic bacteria, further wherein the extracellular product is sublancin.

In yet another embodiment, a composition that repels, reduces, and/or removes bacterial pathogens includes sublancin in a carrier, wherein the carrier includes substantially no intact probiotic bacteria, lysed bacteria, or bacterial fragments.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments.

In yet another embodiment, a composition that repels, reduces, and/or removes bacterial pathogens includes sublancin in a carrier, wherein the sublancin is obtained from a culture containing probiotic bacteria, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes sublancin in a carrier, wherein the sublancin is obtained from a culture containing probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes sublancin in a carrier, wherein the sublancin is obtained from a culture containing probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes sublancin in a carrier, wherein the sublancin is obtained from a culture containing probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes sublancin in a carrier, wherein the sublancin is obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the extracellular product is sublancin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the composition includes substantially no intact probiotic bacteria, lysed bacteira, or bacterial fragments, further wherein the extracellular product is a supernatant or filtrate of a culture of the probiotic bacteria, further wherein the extracellular product is sublancin.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the composition is formulated for use as an anti-bacterial composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the composition is formulated for topical administration.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is sublancin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the extracellular product is a supernatant or filtrate of a culture of the probiotic bacteria, further wherein the extracellular product is sublancin.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method for preventing, removing, reducing, or treating a bacterial or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method for preventing, removing, reducing, or treating a bacterial, yeast, or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein carrier includes substantially no intact probiotic bacteria, lysed bacteria, or bacterial fragments, further wherein the composition is formulated for use in a method for preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is sublancin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the extracellular product is a supernatant or filtrate of a culture of the probiotic bacteria, further wherein the extracellular product is sublancin.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the composition is formulated for use as an antibacterial composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis* further wherein the composition is formulated for use in a method of preventing, removing, reducing, or treating a bacterial, yeast, or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the probiotic bacteria is included in the composition in the form of spores.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the probiotic bacteria is included in the composition in the form of a dried cell mass.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is sublancin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the extracellular product is a supernatant or filtrate of a culture of the probiotic bacteria, further wherein the extracellular product is sublancin.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an antibacterial composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a formulated for topical administration.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is sublancin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the extracellular product is a supernatant or filtrate of a culture of a probiotic bacteria, further wherein the extracellular product is sublancin.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the composition is formulated for use as an anti-bacterial composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is a *Bacillus subtilis* DE111, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is sublancin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the extracellular product is a supernatant or filtrate of a culture of the probiotic bacteria, further wherein the extracellular product is sublancin.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes sublancin in a carrier, wherein the sublancin is obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is sublancin.

In yet another embodiment, a composition that repels, reduces, and/or removes bacterial pathogens includes an extracellular product of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the extracellular product is a supernatant or filtrate of a culture of a probiotic bacteria, further wherein the extracellular product is sublancin.

In yet another embodiment, a composition that repels, reduces, and/or removes bacterial pathogens includes bacillysin, subtilosin, and/or sublancin in a carrier.

In yet another embodiment, a composition that repels, reduces, and/or removes bacterial pathogens includes bacillysin, subtilosin, and/or sublancin in a carrier, wherein the composition is formulated for use as an anti-bacterial composition.

In yet another embodiment, a composition that repels, reduces, and/or removes bacterial pathogens includes bacillysin, subtilosin, and/or sublancin in a carrier, wherein the composition is formulated for use as a cream, gel, or spray.

In yet another embodiment, a composition that repels, reduces, and/or removes bacterial pathogens includes bacillysin, subtilosin, and/or sublancin in a carrier, wherein the composition is a pharmaceutical composition.

In yet another embodiment, a composition that repels, reduces, and/or removes bacterial pathogens includes bacillysin, subtilosin, and/or sublancin in a carrier, wherein the composition is formulated for topical administration.

In yet another embodiment, a composition that repels, reduces, and/or removes bacterial pathogens includes bacillysin, subtilosin, and/or sublancin in a carrier, wherein the composition is formulated for use in medicine.

In yet another embodiment, a composition that repels, reduces, and/or removes bacterial pathogens includes bacillysin, subtilosin, and/or sublancin in a carrier, wherein the composition is formulated for use in a method of preventing, removing, reducing, or treating a bacterial or fungal infection.

In yet another embodiment, a composition that repels, reduces, and/or removes bacterial pathogens includes bacillysin, subtilosin, and/or sublancin in a carrier, wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the composition is formulated for use in a method of preventing, removing, reducing, or treating a bacterial, yeast, or fungal infection.

In yet another embodiment, a composition that repels, reduces, and/or removes bacterial pathogens includes bacillysin, subtilosin, and/or sublancin in a carrier, wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin, subtilosin, and/or sublancin in a carrier, wherein the carrier is suitable for topical application to skin or a mucous membrane of a mammal.

In yet another embodiment, a composition that repels, reduces, and/or removes bacterial pathogens includes bacillysin, subtilosin, and/or sublancin in a carrier, wherein the composition can include from about 1% to about 75% emu oil by weight.

In yet another embodiment, a composition that repels, reduces, and/or removes bacterial pathogens includes bacillysin, subtilosin, and/or sublancin in a carrier, further including an effective amount of a fructooligosaccharide.

In yet another embodiment, a composition that repels, reduces, and/or removes bacterial pathogens includes bacillysin, subtilosin, and/or sublancin in a carrier, further including an effective amount of a fructooligosaccharide, wherein the fructooligosaccharide is present in an amount of from about 10 to about 1000 milligrams per gram of composition.

In yet another embodiment, a composition that repels, reduces, and/or removes bacterial pathogens includes bacillysin, subtilosin, and/or sublancin in a carrier, further including an effective amount of a fructooligosaccharide, wherein the fructooligosaccharide is present in an amount of from about 100 to about 500 milligrams per gram of composition.

In yet another embodiment, a composition that repels, reduces, and/or removes bacterial pathogens includes bacillysin, subtilosin, and/or sublancin in a carrier, further including an effective amount of a fructooligosaccharide, wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the composition is formulated for use as an anti-bacterial composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the composition is formulated for use as a cream, gel, or spray.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the composition is a pharmaceutical composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the composition is formulated for topical administration.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the composition is formulated for use in medicine.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the composition is formulated for use in a method of preventing, removing, reducing, or treating a bacterial or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is cultured under aerobic conditions.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier is suitable for topical application to skin or a mucous membrane of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes an effective amount of a fructooligosaccharide.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is included in the composition in the form of spores.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is included in the composition in the form of a dried cell mass.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the culture containing probiotic bacteria contains $10^3$ to $10^{12}$ viable bacteria or spores per gram of composition.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the one or more extracellular products are bacillysin, subtilosin, and/or sublancin.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the one or more extracellular products are supernatant(s) or filtrate(s) of a culture of the probiotic bacteria, further wherein the one or more extracellular products are bacillysin, subtilosin, and/or sublancin.

In yet another embodiment, a composition that repels, reduces, and/or removes bacterial pathogens includes bacillysin, subtilosin, and/or sublancin in a carrier, wherein the carrier includes substantially no intact probiotic bacteria, lysed bacteria, or bacterial fragments.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the one or more extracellular products are bacillysin, subtilosin, and/or sublancin.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the composition includes substantially no intact probiotic bacteria, lysed bacteria, or bacterial fragments, further wherein the one or more extracellular products are supernatant(s) or filtrate(s) of a culture of the probiotic bacteria, further wherein the one or more extracellular products are bacillysin, subtilosin, and/or sublancin.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the composition is formulated for use as an anti-bacterial composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the composition is formulated for use as a cream, gel, or spray.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the composition is a pharmaceutical composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the composition is formulated for topical administration.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the composition is formulated for use in medicine.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the probiotic bacteria is cultured under aerobic conditions.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier is suitable for topical application to skin or a mucous membrane of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes an effective amount of a fructooligosaccharide.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the probiotic bacteria is included in the composition in the form of spores.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the probiotic bacteria is included in the composition in the form of a dried cell mass.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the culture containing probiotic bacteria contains $10^3$ to $10^{12}$ viable bacteria or spores per gram of composition.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is a *Bacillus* spp. bacteria, further wherein the one or more extracellular products are bacillysin, subtilosin, and/or sublancin.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is a *Bacillus* spp. bacteria, further wherein the one or more extracellular products are supernatant(s) or filtrate(s) of a culture of the probiotic bacteria, further wherein the one or more extracellular products are bacillysin, subtilosin, and/or sublancin.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a *Bacillus* spp. bacteria, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the one or more extracellular products are bacillysin, subtilosin, and/or sublancin.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is a *Bacillus* spp. bacteria, further wherein the composition includes substantially no intact probiotic bacteria, lysed bacteria, or bacterial fragments, further wherein the one or more extracellular products are supernatant(s) or filtrate(s) of a culture of the probiotic bacteria, further wherein the one or more extracellular products are bacillysin, subtilosin, and/or sublancin.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the composition is formulated for use as an antibacterial composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the composition is formulated for use as a cream, gel, or spray.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the composition is a pharmaceutical composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the composition is formulated for topical administration.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the composition is formulated for use in medicine.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the probiotic bacteria is cultured under aerobic conditions.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier is suitable for topical application to skin or a mucous membrane of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes an effective amount of a fructooligosaccharide.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria further wherein the probiotic bacteria is a strain of *Bacillus subtilis*, further wherein the probiotic bacteria is included in the composition in the form of spores.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria further wherein the probiotic bacteria is a strain of *Bacillus subtilis*, further wherein the probiotic bacteria is included in the composition in the form of a dried cell mass.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria further wherein the probiotic bacteria is a strain of *Bacillus subtilis*, further wherein the culture containing probiotic bacteria contains $10^3$ to $10^{12}$ viable bacteria or spores per gram of composition.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is a strain of *Bacillus subtilis*, further wherein the one or more extracellular products are bacillysin, subtilosin, and/or sublancin.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is a strain of *Bacillus subtilis*, further wherein the one or more extracellular products are supernatant(s) or filtrate(s) of a culture of the probiotic bacteria, further wherein the one or more extracellular products are bacillysin, subtilosin, and/or sublancin.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as an antibacterial composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is a strain of *Bacillus subtilis*, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the one or more extracellular products are bacillysin, subtilosin, and/or sublancin.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is a strain of *Bacillus subtilis*, further wherein the composition includes substantially no intact probiotic bacteria, lysed bacteria, or bacterial fragments, further wherein the one or more extracellular products are supernatant(s) or filtrate(s) of a culture of a probiotic bacteria, further wherein the one or more extracellular products are bacillysin, subtilosin, and/or sublancin.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the composition is formulated for use as an anti-bacterial composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the composition is formulated for use as a cream, gel, or spray.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the composition is a pharmaceutical composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the composition is formulated for topical administration.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the composition is formulated for use in medicine.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the composition is formulated for use in a method of preventing, removing, reducing, or treating a bacterial or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the probiotic bacteria is cultured under aerobic conditions.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the composition is formulated for use in a method of preventing, removing, reducing or treating a bacterial or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier is suitable for topical application to skin or a mucous membrane of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes an effective amount of a fructooligosaccharide.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the probiotic bacteria is included in the composition in the form of spores.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the probiotic bacteria is included in the composition in the form of a dried cell mass.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the culture containing probiotic bacteria contains $10^3$ to $10^{12}$ viable bacteria or spores per gram of composition.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is *Bacillus subtilis* DE111, further wherein the one or more extracellular products are bacillysin, subtilosin, and/or sublancin.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is *Bacillus subtilis* DE111, further wherein the one or more extracellular products are supernatant(s) or filtrate(s) of a culture of the probiotic bacteria, further wherein the one or more extracellular products are bacillysin, subtilosin, and/or sublancin.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as an anti-bacterial composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use as a cream, gel, or spray.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is a pharmaceutical composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for topical administration.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in medicine.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is cultured under aerobic conditions.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition is formulated for use in a method of preventing, removing, reducing, or treating a bacterial, yeast, or fungal infection, further wherein the infection is an infection of the epidermis of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is selected from the group consisting of an emulsion, cream, lotion, gel, oil, ointment, suspension, aerosol spray, powder, aerosol powder, and semisolid formulation.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier is suitable for topical application to skin or a mucous membrane of a mammal.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 10 to about 1000 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the fructooligosaccharide is present in an amount of from about 100 to about 500 milligrams per gram of composition.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the carrier includes an effective amount of a fructooligosaccharide, further wherein the composition can include from about 1% to about 75% emu oil by weight.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of spores.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the probiotic bacteria is included in the composition in the form of a dried cell mass.

In yet another embodiment, a composition that repels, reduces, and/or removes bacterial pathogens includes bacillysin, subtilosin, and/or sublancin in a carrier, wherein the bacillysin, subtilosin, and/or sublancin are obtained from a culture containing a probiotic bacteria, further wherein the probiotic bacteria is *Bacillus subtilis* DE111, further wherein the carrier includes substantially no intact probiotic bacteria, lysed bacteria, or bacterial fragments, further wherein the culture containing probiotic bacteria contains $10^3$ to $10^{12}$ viable bacteria or spores per gram of composition.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the one or more extracellular products are bacillysin, subtilosin, and/or sublancin.

In yet another embodiment, a composition that repels, reduces, and/or removes bacterial pathogens includes one or more extracellular products of a probiotic bacteria in a pharmaceutically acceptable carrier suitable for topical administration to skin or a mucous membrane of a mammal, wherein the probiotic bacteria is *Bacillus subtilis* DE111, further wherein the composition includes substantially no intact probiotic bacteria, lysed bacteria, or bacterial fragments, further wherein the one or more extracellular products are supernatant(s) or filtrate(s) of a culture of a probiotic bacteria, further wherein the one or more extracellular products are bacillysin, subtilosin, and/or sublancin.

In an embodiment, a method of preventing, removing, reducing, and/or treating a bacterial, yeast, and/or fungal infection in a mammal can include the steps of:

(a) providing a composition that repels, reduces, and/or removes plant fungal pathogens; and (b) administering the composition to the mammal.

The process described herein above provides a method of preventing, removing, reducing, and/or treating a bacterial, yeast, and/or fungal infection in a mammal.

In another embodiment, a method of preventing, removing, reducing, and/or treating a bacterial, yeast, and/or fungal infection in a mammal can include the steps of:

(a) providing a composition that repels, reduces, and/or removes fungal pathogens; and (b) administering the composition to the mammal.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that transports iron across cell membranes; and (b) administering the composition to the mammal.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes bacterial pathogens; and (b) administering the composition to the mammal.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes plant fungal pathogens;

(b) administering the composition to skin or a mucous membrane of the mammal; and (c) maintaining the composition on the skin or mucous membrane of the mammal for a duration of time sufficient to prevent, remove, reduce, and/or treat the bacterial, yeast, and/or fungal infection.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes fungal pathogens;

(b) administering the composition to skin or a mucous membrane of the mammal; and (c) maintaining the composition on the skin or mucous membrane of the mammal for a duration of time sufficient to prevent, remove, reduce, and/or treat the bacterial, yeast, and/or fungal infection.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that transports iron across cell membranes;

(b) administering the composition to skin or a mucous membrane of the mammal; and (c) maintaining the composition on the skin or mucous membrane of the mammal for a duration of time sufficient to prevent, remove, reduce, and/or treat the bacterial, yeast, and/or fungal infection.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes bacterial pathogens;

(b) administering the composition to skin or a mucous membrane of the mammal; and (c) maintaining the composition on the skin or mucous membrane of the mammal for a duration of time sufficient to prevent, remove, reduce, and/or treat the bacterial, yeast, and/or fungal infection.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes plant fungal pathogens, wherein the composition includes spores including a *Bacillus* spp bacteria;

(b) administering the composition to skin or a mucous membrane of the mammal; and (c) maintaining the composition on the skin or mucous membrane of the mammal for a duration of time sufficient for the spores to germinate.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes fungal pathogens, wherein the composition includes spores including a *Bacillus* spp bacteria;

(b) administering the composition to skin or a mucous membrane of a mammal; and (c) maintaining the composition on the skin or mucous membrane of the mammal for a duration of time sufficient for the spores to germinate.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that transports iron across cell membranes, wherein the composition includes spores including a *Bacillus* spp bacteria;

(b) administering the composition to skin or a mucous membrane of a mammal; and (c) maintaining the composition on the skin or mucous membrane of the mammal for a duration of time sufficient for the spores to germinate.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes bacterial pathogens, wherein the composition includes spores including a *Bacillus* spp bacteria;

(b) administering the composition to skin or a mucous membrane of a mammal; and (c) maintaining the composition on the skin or mucous membrane of the mammal for a duration of time sufficient for the spores to germinate.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes plant fungal pathogens, wherein the composition includes spores including a *Bacillus* spp bacteria;

(b) administering the composition to skin or a mucous membrane of a mammal; and (c) maintaining the composition on the skin or mucous membrane of the mammal for a duration of time sufficient for the spores to germinate;

wherein the maintaining step (c) inhibits growth of one or more microbes selected from the group consisting of *Escherichia coli, Candida* species, *Trichorphyton* species, and mixtures thereof.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes fungal pathogens, wherein the composition includes spores including a *Bacillus* spp bacteria;

(b) administering the composition to skin or a mucous membrane of a mammal; and (c) maintaining the composition on the skin or mucous membrane of the mammal for a duration of time sufficient for the spores to germinate;

wherein the maintaining step (c) inhibits growth of one or more microbes selected from the group consisting of *Escherichia coli, Candida* species, *Trichorphyton* species, and mixtures thereof.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that transports iron across cell membranes, wherein the composition includes spores including a *Bacillus* spp bacteria;

(b) administering the composition to skin or a mucous membrane of a mammal; and (c) maintaining the composition on the skin or mucous membrane of the mammal for a duration of time sufficient for the spores to germinate;

wherein the maintaining step (c) inhibits growth of one or more microbes selected from the group consisting of *Escherichia coli, Candida* species, *Trichlorphyton* species, and mixtures thereof.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes bacterial pathogens, wherein the composition includes spores including a *Bacillus* spp bacteria;

(b) administering the composition to skin or a mucous membrane of a mammal; and (c) maintaining the composition on the skin or mucous membrane of the mammal for a duration of time sufficient for the spores to germinate;

wherein the maintaining step (c) inhibits growth of one or more microbes selected from the group consisting of *Escherichia coli*, *Candida* species, *Trichlorphyton* species, and mixtures thereof.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes plant fungal pathogens, wherein the composition includes spores including a strain of *Bacillus subtilis*;

(b) administering the composition to skin or a mucous membrane of the mammal; and (c) maintaining the composition on the skin or mucous membrane of the mammal for a duration of time sufficient for the spores to germinate.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes fungal pathogens, wherein the composition includes spores including a strain of *Bacillus subtilis*;

(b) administering the composition to skin or a mucous membrane of the mammal; and (c) maintaining the composition on the skin or mucous membrane of the mammal for a duration of time sufficient for the spores to germinate.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that transports iron across cell membranes, wherein the composition includes spores including a strain of *Bacillus subtilis*;

(b) administering the composition to skin or a mucous membrane of the mammal; and (c) maintaining the composition on the skin or mucous membrane of the mammal for a duration of time sufficient for the spores to germinate.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes bacterial pathogens, wherein the composition includes spores including a strain of *Bacillus subtilis*;

(b) administering the composition to skin or a mucous membrane of the mammal; and (c) maintaining the composition on the skin or mucous membrane of the mammal for a duration of time sufficient for the spores to germinate.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes plant fungal pathogens, wherein the composition includes spores including a strain of *Bacillus subtilis*;

(b) administering the composition to skin or a mucous membrane of the mammal; and (c) maintaining the composition on the skin or mucous membrane of the mammal for a duration of time sufficient for the spores to germinate;

wherein the maintaining step (c) inhibits growth of one or more microbes selected from the group consisting of *Escherichia coli*, *Candida* species, *Trichlorphyton* species, and mixtures thereof.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes fungal pathogens, wherein the composition includes spores including a strain of *Bacillus subtilis*;

(b) administering the composition to skin or a mucous membrane of the mammal; and (c) maintaining the composition on the skin or mucous membrane of the mammal for a duration of time sufficient for the spores to germinate;

wherein the maintaining step (c) inhibits growth of one or more microbes selected from the group consisting of *Escherichia coli*, *Candida* species, *Trichlorphyton* species, and mixtures thereof.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that transports iron across cell membranes, wherein the composition includes spores including a strain of *Bacillus subtilis*;

(b) administering the composition to skin or a mucous membrane of the mammal; and (c) maintaining the composition on the skin or mucous membrane of the mammal for a duration of time sufficient for the spores to germinate;

wherein the maintaining step (c) inhibits growth of one or more microbes selected from the group consisting of *Escherichia coli*, *Candida* species, *Trichlorphyton* species, and mixtures thereof.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes bacterial pathogens, wherein the composition includes spores including a strain of *Bacillus subtilis*;

(b) administering the composition to skin or a mucous membrane of the mammal; and (c) maintaining the composition on the skin or mucous membrane of the mammal for a duration of time sufficient for the spores to germinate;

wherein the maintaining step (c) inhibits growth of one or more microbes selected from the group consisting of *Escherichia coli, Candida* species, *Trichlorphyton* species, and mixtures thereof.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes plant fungal pathogens, wherein the composition includes $10^3$ to $10^{12}$ viable *Bacillus* spp bacteria or spores including *Bacillus* spp bacteria per gram of composition; and (b) administering the composition to skin or a mucous membrane of the mammal.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes fungal pathogens, wherein the composition includes $10^3$ to $10^{12}$ viable *Bacillus* spp bacteria or spores including *Bacillus* spp bacteria per gram of composition; and (b) administering the composition to skin or a mucous membrane of the mammal.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that transports iron across cell membranes, wherein the composition includes $10^3$ to $10^{12}$ viable *Bacillus* spp bacteria or spores including *Bacillus* spp bacteria per gram of composition; and (b) administering the composition to skin or a mucous membrane of the mammal.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes bacterial pathogens, wherein the composition includes $10^3$ to $10^{12}$ viable *Bacillus* spp bacteria or spores including *Bacillus* spp bacteria per gram of composition; and (b) administering the composition to skin or a mucous membrane of the mammal.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes plant fungal pathogens, wherein the composition includes viable *Bacillus* spp bacteria or spores including *Bacillus* spp bacteria; and (b) administering from $10^8$ to $10^{10}$ viable *Bacillus* spp bacteria or spores including *Bacillus* spp bacteria per gram of composition per day.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes fungal pathogens, wherein the composition includes viable *Bacillus* spp bacteria or spores including *Bacillus* spp bacteria; and (b) administering from $10^8$ to $10^{10}$ viable *Bacillus* spp bacteria or spores including *Bacillus* spp bacteria per gram of composition per day.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that transports iron across cell membranes, wherein the composition includes viable *Bacillus* spp bacteria or spores including *Bacillus* spp bacteria; and (b) administering from $10^8$ to $10^{10}$ viable *Bacillus* spp bacteria or spores including *Bacillus* spp bacteria per gram of composition per day.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes bacterial pathogens, wherein the composition includes viable *Bacillus* spp bacteria or spores including *Bacillus* spp bacteria; and (b) administering from $10^8$ to $10^{10}$ viable *Bacillus* spp bacteria or spores including *Bacillus* spp bacteria per gram of composition per day.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes plant fungal pathogens, wherein the composition includes viable *Bacillus* spp bacteria or spores including *Bacillus* spp bacteria; and (b) administering from $5 \cdot 10^8$ to $10^9$ viable *Bacillus* spp bacteria or spores including *Bacillus* spp bacteria per gram of composition per day.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes fungal pathogens, wherein the composition includes viable *Bacillus* spp bacteria or spores including *Bacillus* spp bacteria; and (b) administering from 5·10⁸ to 10⁹ viable *Bacillus* spp bacteria or spores including *Bacillus* spp bacteria per gram of composition per day.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that transports iron across cell membranes, wherein the composition includes viable *Bacillus* spp bacteria or spores including *Bacillus* spp bacteria; and (b) administering from 5·10⁸ to 10⁹ viable *Bacillus* spp bacteria or spores including *Bacillus* spp bacteria per gram of composition per day.

The process described herein above provides a method of preventing, removing, reducing, and/or treating a bacterial, yeast, and/or fungal infection in a mammal.

In yet another embodiment, a method of preventing, removing, reducing, and/or treating a bacterial, yeast, and/or fungal infection in a mammal can include the steps of:

(a) providing a composition that repels, reduces, and/or removes bacterial pathogens, wherein the composition includes viable *Bacillus* spp bacteria or spores including *Bacillus* spp bacteria; and (b) administering from 5·10⁸ to 10⁹ viable *Bacillus* spp bacteria or spores including *Bacillus* spp bacteria per gram of composition per day.

The process described herein above provides a method of preventing, removing, reducing, and/or treating a bacterial, yeast, and/or fungal infection in a mammal.

In an embodiment, a method of preparing a surface can include the steps of:

(a) providing a composition that repels, reduces, and/or removes plant fungal pathogens; and (b) applying the composition to the surface.

The process described herein above provides a method of preparing a surface.

In another embodiment, a method of preparing a surface can include the steps of:

(a) providing a composition that repels, reduces, and/or removes fungal pathogens; and (b) applying the composition to the surface.

The process described herein above provides a method of preparing a surface.

In yet another embodiment, a method of preparing a surface can include the steps of:

(a) providing a composition that transports iron across cell membranes;

(b) applying the composition to the surface.

The process described herein above provides a method of preparing a surface.

In yet another embodiment, a method of preparing a surface can include the steps of:

(a) providing a composition that repels, reduces, and/or removes bacterial pathogens; and (b) applying the composition to the surface.

The process described herein above provides a method of preparing a surface.

In yet another embodiment, a method of preparing a surface can include the steps of:

(a) providing a composition that repels, reduces, and/or removes plant fungal pathogens, wherein the composition includes spores including a *Bacillus* spp bacteria;

(b) applying the composition to the surface; and (c) maintaining the composition on the surface for a duration of time sufficient for the spores to germinate.

The process described herein above provides a method of preparing a surface.

In yet another embodiment, a method of preparing a surface can include the steps of:

(a) providing a composition that repels, reduces, and/or removes fungal pathogens, wherein the composition includes spores including a *Bacillus* spp bacteria;

(b) applying the composition to the surface; and (c) maintaining the composition on the surface for a duration of time sufficient for the spores to germinate.

The process described herein above provides a method of preparing a surface.

In yet another embodiment, a method of preparing a surface can include the steps of:

(a) providing a composition that transports iron across cell membranes, wherein the composition includes spores including a *Bacillus* spp bacteria;

(b) applying the composition to the surface; and (c) maintaining the composition on the surface for a duration of time sufficient for the spores to germinate.

The process described herein above provides a method of preparing a surface.

In yet another embodiment, a method of preparing a surface can include the steps of:

(a) providing a composition that repels, reduces, and/or removes bacterial pathogens, wherein the composition includes spores including a *Bacillus* spp bacteria;

(b) applying the composition to the surface; and (c) maintaining the composition on the surface for a duration of time sufficient for the spores to germinate.

The process described herein above provides a method of preparing a surface.

In yet another embodiment, a method of preparing a surface can include the steps of:

(a) providing a composition that repels, reduces, and/or removes plant fungal pathogens, wherein the composition includes spores including a strain of *Bacillus subtilis;*

(b) applying the composition to the surface; and (c) maintaining the composition on the surface for a duration of time sufficient for the spores to germinate.

The process described herein above provides a method of preparing a surface.

In yet another embodiment, a method of preparing a surface can include the steps of:

(a) providing a composition that repels, reduces, and/or removes fungal pathogens, wherein the composition includes spores including a strain of *Bacillus subtilis;*

(b) applying the composition to the surface; and (c) maintaining the composition on the surface for a duration of time sufficient for the spores to germinate.

The process described herein above provides a method of preparing a surface.

In yet another embodiment, a method of preparing a surface can include the steps of:

(a) providing a composition that transports iron across cell membranes, wherein the composition includes spores including a strain of *Bacillus subtilis;*

(b) applying the composition to the surface; and (c) maintaining the composition on the surface for a duration of time sufficient for the spores to germinate.

The process described herein above provides a method of preparing a surface.

In yet another embodiment, a method of preparing a surface can include the steps of:

(a) providing a composition that repels, reduces, and/or removes bacterial pathogens, wherein the composition includes spores including a strain of *Bacillus subtilis;*

(b) applying the composition to the surface; and (c) maintaining the composition on the surface for a duration of time sufficient for the spores to germinate.

The process described herein above provides a method of preparing a surface.

In yet another embodiment, a method of preparing a surface can include the steps of:

(a) providing a composition that repels, reduces, and/or removes plant fungal pathogens, wherein the composition includes $10^3$ to $10^{12}$ viable *Bacillus* spp bacteria or spores including *Bacillus* spp bacteria per gram of composition; and (b) applying the composition to the surface.

The process described herein above provides a method of preparing a surface.

In yet another embodiment, a method of preparing a surface can include the steps of:

(a) providing a composition that repels, reduces, and/or removes fungal pathogens, wherein the composition includes $10^3$ to $10^{12}$ viable *Bacillus* spp bacteria or spores including *Bacillus* spp bacteria per gram of composition; and (b) applying the composition to the surface.

The process described herein above provides a method of preparing a surface.

In yet another embodiment, a method of preparing a surface can include the steps of:

(a) providing a composition that transports iron across cell membranes, wherein the composition includes $10^3$ to $10^{12}$ viable *Bacillus* spp bacteria or spores including *Bacillus* spp bacteria per gram of composition; and (b) applying the composition to the surface.

The process described herein above provides a method of preparing a surface.

In yet another embodiment, a method of preparing a surface can include the steps of:

(a) providing a composition that repels, reduces, and/or removes bacterial pathogens, wherein the composition includes $10^3$ to $10^{12}$ viable *Bacillus* spp bacteria or spores including *Bacillus* spp bacteria per gram of composition; and (b) applying the composition to the surface.

The process described herein above provides a method of preparing a surface.

In an embodiment, a method of inhibiting growth or activity of bacteria, yeast, and/or fungi on skin or a mucous membrane of a mammal can include the steps of:

(a) providing a composition that repels, reduces, and/or removes plant fungal pathogens, wherein the composition includes an extracellular product of a strain of *Bacillus subtilis;*

(b) administering the composition to the skin or mucous membrane of the mammal; and (c) maintaining the composition on the skin or mucous membrane of the mammal for sufficient time to inhibit the growth of the bacteria, yeast, and/or fungi.

The process described herein above provides a method of inhibiting growth or activity of bacteria, yeast, and/or fungi on skin or a mucous membrane of a mammal.

In another embodiment, a method of inhibiting growth or activity of bacteria, yeast, and/or fungi on skin or a mucous membrane of a mammal can include the steps of:

(a) providing a composition that repels, reduces, and/or removes fungal pathogens, wherein the composition includes an extracellular product of a strain of *Bacillus subtilis;*

(b) administering the composition to the skin or mucous membrane of the mammal; and (c) maintaining the composition on the skin or mucous membrane of the mammal for sufficient time to inhibit the growth of the bacteria, yeast, and/or fungi.

The process described herein above provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal can include the steps of:

(a) providing a composition that transports iron across cell membranes, wherein the composition includes an extracellular product of a strain of *Bacillus subtilis;*

(b) administering the composition to the skin or mucous membrane of the mammal; and (c) maintaining the composition on the skin or mucous membrane of the mammal for sufficient time to inhibit the growth of the bacteria, yeast, and/or fungi.

The process described herein above provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal can include the steps of:

(a) providing a composition that transports iron across cell membranes, wherein the composition includes an extracellular product of a strain of *Bacillus subtilis;*

(b) administering the composition to the skin or mucous membrane of the mammal; and (c) maintaining the composition on the skin or mucous membrane of the mammal for sufficient time to inhibit the growth of the bacteria, yeast, and/or fungi.

The process described herein above provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal can include the steps of:

(a) providing a composition that repels, reduces, and/or removes bacterial pathogens, wherein the composition includes an extracellular product of a strain of *Bacillus subtilis;*

(b) administering the composition to the skin or mucous membrane of the mammal; and (c) maintaining the composition on the skin or mucous membrane of the mammal for sufficient time to inhibit the growth of the bacteria, yeast, and/or fungi.

The process described herein above provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal can include the steps of:

(a) providing a composition that repels, reduces, and/or removes plant fungal pathogens, wherein the composition includes a *Bacillus* spp bacteria;

(b) applying the composition to a solid surface;

(c) contacting the solid surface with the composition applied thereto to skin or a mucous membrane of a mammal; and (d) maintaining contact between the solid surface with the composition applied thereto and the skin or mucous membrane of the mammal for a duration of time sufficient for inhibition of growth of bacteria, yeast, and/or fungi on the skin or mucous membrane of the mammal.

The process described herein above provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal can include the steps of:

(a) providing a composition that repels, reduces, and/or removes fungal pathogens, wherein the composition includes a *Bacillus* spp bacteria;

(b) applying the composition to a solid surface;

(c) contacting the solid surface with the composition applied thereto to skin or a mucous membrane of a mammal; and (d) maintaining contact between the solid surface with the composition applied thereto and the skin or mucous membrane of the mammal for a duration of time sufficient for inhibition of growth of bacteria, yeast, and/or fungi on the skin or mucous membrane of the mammal.

The process described herein above provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal can include the steps of:

(a) providing a composition that transports iron across cell membranes, wherein the composition includes a *Bacillus* spp bacteria;

(b) applying the composition to a solid surface;

(c) contacting the solid surface with the composition applied thereto to skin or a mucous membrane of a mammal; and (d) maintaining contact between the solid surface with the composition applied thereto and the skin or mucous membrane of the mammal for a duration of time sufficient for inhibition of growth of bacteria, yeast, and/or fungi on the skin or mucous membrane of the mammal.

The process described herein above provides a method of inhibiting growth or activity of bacteria, yeast, and/or fungi on skin or a mucous membrane of a mammal.

In yet another embodiment, a method of inhibiting growth or activity of bacteria, yeast, and/or fungi on skin or a mucous membrane of a mammal can include the steps of:

(a) providing a composition that repels, reduces, and/or removes bacterial pathogens, wherein the composition includes a *Bacillus* spp bacteria;

(b) applying the composition to a solid surface;

(c) contacting the solid surface with the composition applied thereto to skin or a mucous membrane of a mammal;

(d) maintaining contact between the solid surface with the composition applied thereto and the skin or mucous membrane of the mammal for a duration of time sufficient for inhibition of growth of bacteria, yeast, and/or fungi on the skin or mucous membrane of the mammal.

The process described herein above provides a method of inhibiting growth or activity of bacteria, yeast, and/or fungi on skin or a mucous membrane of a mammal.

In an embodiment, an article of manufacture that prevents, removes, reduces, and/or treats a bacterial, yeast, and/or fungal infection can include: a flexible article that can be affixed to skin or a mucous membrane of a mammal; and an effective amount of a *Bacillus* spp bacteria applied to the flexible article; wherein the *Bacillus* spp bacteria effects inhibitory activity on the bacterial, yeast, and/or fungal infection that occurs adjacent to or on the skin or mucous membrane of the mammal.

In another embodiment, an article of manufacture that prevents, removes, reduces, and/or treats a bacterial, yeast, and/or fungal infection can include: a flexible article that can be affixed to skin or a mucous membrane of a mammal; and an effective amount of a *Bacillus* spp bacteria applied to the flexible article; wherein the *Bacillus* spp bacteria effects inhibitory activity on the bacterial, yeast, and/or fungal infection that occurs adjacent to or on the skin or mucous membrane of the mammal; further wherein the *Bacillus* spp bacteria is a strain of *Bacillus subtilis*.

In yet another embodiment, an article of manufacture that prevents, removes, reduces, and/or treats a bacterial, yeast, and/or fungal infection can include: a flexible article that can be affixed to skin or a mucous membrane of a mammal; and an effective amount of a *Bacillus* spp bacteria applied to the flexible article; wherein the *Bacillus* spp bacteria effects inhibitory activity on the bacterial, yeast, and/or fungal infection that occurs adjacent to or on the skin or mucous membrane of the mammal; wherein the effective amount of *Bacillus* spp bacteria is $10^3$ to $10^{12}$ viable bacteria or spore per flexible article.

In yet another embodiment, an article of manufacture that prevents, removes, reduces, and/or treats a bacterial, yeast, and/or fungal infection can include: a flexible article that can be affixed to skin or a mucous membrane of a mammal; an effective amount of a *Bacillus* spp bacteria applied to the flexible article; and an effective amount of a fructooligosaccharide; wherein the *Bacillus* spp bacteria effects inhibitory activity on the bacterial, yeast, and/or fungal infection that occurs adjacent to or on the skin or mucous membrane of the mammal.

In yet another embodiment, an article of manufacture that prevents, removes, reduces, and/or treats a bacterial, yeast, and/or fungal infection can include: a flexible article that can be affixed to skin or a mucous membrane of a mammal; an effective amount of a *Bacillus* spp bacteria applied to the flexible article; and an effective amount of a fructooligosaccharide; wherein the *Bacillus* spp bacteria effects inhibitory activity on the bacterial, yeast, and/or fungal infection that occurs adjacent to or on the skin or mucous membrane of the mammal; further wherein the effective amount of the fructooligosaccharide is present in an amount of from about 10 to about 1000 milligrams per flexible article.

In an embodiment, a method of preparing a composition that prevents, removes, reduces, and/or treats a bacterial, yeast, and/or fungal infection can include the steps of:

(a) culturing *Bacillus subtilis* DE111 in media, so as to produce a composition that prevents, removes, reduces, and/or treats a bacterial, yeast, and/or fungal infection.

The process described herein above provides a method of preparing a composition that prevents, removes, reduces, and/or treats a bacterial, yeast, and/or fungal infection.

In another embodiment, a method of preparing a composition that prevents, removes, reduces, and/or treats a bacterial, yeast, and/or fungal infection can include the steps of:

(a) culturing *Bacillus subtilis* DE111 in media;

(b) separating the *Bacillus subtilis* DE111 from the media, so as to produce a composition that prevents, removes, reduces, and/or treats a bacterial, yeast, and/or fungal infection;

The process described herein above provides a method of preparing a composition that prevents, removes, reduces, and/or treats a bacterial, yeast, and/or fungal infection.

In yet another embodiment, a method of preparing a composition that prevents, removes, reduces, and/or treats a bacterial, yeast, and/or fungal infection can include the steps of:
 (a) culturing *Bacillus subtilis* DE111 in media;
 (b) separating the *Bacillus subtilis* DE111 from the media; and
 (c) combining the media with a carrier so as to produce a composition that prevents, removes, reduces, and/or treats a bacterial, yeast, and/or fungal infection.

The process described herein above provides a method of preparing a composition that prevents, removes, reduces, and/or treats a bacterial, yeast, and/or fungal infection.

In yet another embodiment, a method of preparing a composition that prevents, removes, reduces, and/or treats a bacterial, yeast, and/or fungal infection can include the steps of:
 (a) culturing *Bacillus subtilis* DE111 in media;
 (b) separating the *Bacillus subtilis* DE111 from the media;
 (c) sterilizing the media; and
 (d) combining the media with a carrier so as to produce a composition that prevents, removes, reduces, and/or treats a bacterial, yeast, and/or fungal infection.

The process described herein above provides a method of preparing a composition that prevents, removes, reduces, and/or treats a bacterial, yeast, and/or fungal infection.

In yet another embodiment, a method of preparing a composition that prevents, removes, reduces, and/or treats a bacterial, yeast, and/or fungal infection can include the steps of:
 (a) culturing *Bacillus subtilis* DE111 in media;
 (b) separating the *Bacillus subtilis* DE111 from the media;
 (c) concentrating the media; and
 (d) combining the media with a carrier so as to produce a composition that prevents, removes, reduces, and/or treats a bacterial, yeast, and/or fungal infection.

The process described herein above provides a method of preparing a composition that prevents, removes, reduces, and/or treats a bacterial, yeast, and/or fungal infection.

In yet another embodiment, a method of preparing a composition that prevents, removes, reduces, and/or treats a bacterial, yeast, and/or fungal infection can include the steps of:
 (a) culturing *Bacillus subtilis* DE111 in media;
 (b) separating the *Bacillus subtilis* DE111 from the media;
 (c) sterilizing the media;
 (d) concentrating the media; and
 (e) combining the media with a carrier so as to produce a composition that prevents, removes, reduces, and/or treats a bacterial, yeast, and/or fungal infection.

The process described herein above provides a method of preparing a composition that prevents, removes, reduces, and/or treats a bacterial, yeast, and/or fungal infection.

The compositions and methods described above may be further understood in connection with the following Examples. In addition, the following non-limiting examples are provided to illustrate the invention. However, the person skilled in the art will appreciate that it may be necessary to vary the procedures for any given embodiment of the invention, e.g., vary the order or steps.

Example 1

*Bacillus subtilis* DE111 Antifungal Properties
A. Methods and Materials
1. Bacterial and Fungal Strains

*Bacillus subtilis* DE111 was analyzed for its antifungal properties. To definitively characterize its antifungal nature, next generation sequencing and genome mining were incorporated. To determine inhibition of growth from a spectrum of fungi include those of agricultural importance, the following species of fungi have been utilized in this study: *Alternaria alternata, Sordaria fimicola, Aspergillus niger, Cladosporium* sp, *Fusarium* sp, *Geotrichum candidum, Rhodotorula* sp, *Trichoderma* sp, and *Zygorhynchus* sp. Test fungi used in the experiment were obtained from the Frederick stock culture collection (Tuskegee University, Alabama, USA) and identified using standard morphological techniques. See, e.g., H. L. BARNETT & B. B. HUNTER, ILLUSTRATED GENERA OF IMPERFECT FUNGI (Burgess Publ'g Co. 1972), incorporated by reference herein in its entirety.

2. In Vitro Antagonism Screening

Mycelial inhibition challenges were made on PDA plates by a streak method. For this method, new PDA bottle slants were inoculated with a spore suspension from a stock culture and incubated at 26° C. for three (3) days. Three milliliters (mL) of sterile water were added to the bottle slant to create a cell suspension. For the streak tests, single median streaks were made on PDA plates with a loopful of cell suspension from a 3-day-old PDA bottle slant culture. All plates were incubated for 3 days at 26° C. before being inoculated with a test fungus. A uniform-size plug of a PDA culture of each fungus was placed one centimeter on opposite sides of the streak. Each experiment was replicated ten times. Depending on the growth response of each fungus, all plates were incubated at 26° C. for 3 or more days.

3. Genome Sequencing and Phylogeny

The genome of *Bacillus subtilis* DE111 was sequenced previously. The sequence data was deposited in NCBI GenBank under accession number CP013984. Genome comparisons and alignments for phylogenetic trees were made using BIGSdb software. See, e.g., K. A. Jolley & M. C. Maiden, *BIGSdb: scalable analysis of bacterial genome variation at the population level*, 11 BMC BIOINFORMATICS 595 (2010), incorporated by reference herein in its entirety. Comparative genomics were based on gene annotations based on RAST server. See, e.g., R. Overbeek, et al., *The SEED and the Rapid Annotation of microbial genomes using Subsystems Technology (RAST)*, 42 NUCLEIC ACIDS RESEARCH D206 (2014), incorporated by reference herein in its entirety. Secondary metabolite clusters were identified with anti-SMASH 3.0 or direct blasting. See, e.g., T. Weber, et al., *antiSMASH 3.0—a comprehensive resource for the genome mining of biosynthetic gene clusters*, 43 NUCLEIC ACIDS RESEARCH W237 (2015), incorporated by reference herein in its entirety.

4. LC-MS/MS Analysis

Bacterial cultures were grown in 10 milliliters of tryptic soy broth at 37° C. and 200 rpm for 72 hours. The culture media was centrifuged at 13,000 g for 10 minutes and the supernatant removed. Mass spectrometry analysis of the supernatant samples (2 µL or 25 µL injection) was performed by LC-MS (Thermo Acella HPLC) through a narrow-bore (2.1 µm×150 mm, 3 µm particle size) C18 column (Inertsil, GL Sciences, Inc., Torrance, Calif.) running a gradient elution of 95% A: 5% B (eluant A 18 MΩ water/0.1% formic acid, eluant B 100% methanol/0.1% formic acid) to 5% A: 95% B over 65 minutes at a flow rate of 250 µL/min, followed by a 5 minute B washout and 10 minute re-equilibration, while maintaining a constant column temperature of 30° C. Electrospray positive mode ionization data were collected with a linear ion trap-Orbitrap mass spectrometer (Thermo LTQ-Orbitrap Discovery) under Xcalibur 2.1 control. Prior to LC-MS" experiments the instrument was tuned and calibrated using the LTQ tune mix. Tandem mass spectral data were collected using collision-induced dissociation ("CID," collision energy ("CE")=25 and 35) in the LTQ and Higher-energy collision dissociation (HCD, CE=35 and 45) in the Orbitrap analyzer.

B. Results

1. Isolation and Antifungal Activity

To understand the nature of the antifungal activity, in vitro antagonism was evaluated for a diverse group of fungi. The results showed the strain was an effective antagonist of all of the fungi tested. See Table 1.

TABLE 1

Summary of in vitro antagonism of selected fungi by *Bacillus subtilis* DE111

| Fungi | In vitro inhibition |
|---|---|
| *Alternaria alternate* | + |
| *Aspergillus niger* | + |
| *Cladosporium* sp. | + |
| *Fusarium* sp. | + |
| *Geotrichum candidum* | + |
| *Rhodotorula* sp. | + |
| *Sordaria fimicola* | + |
| *Trichoderma* sp. | + |
| *Zygorhynchus* sp. | + |
| *Penicillum* sp. | − |

2. Genome Sequencing and Phylogeny

The draft genome was used to accurately identify the strain using a MLSA phylogenetic approach. The results show the strain is a member of the *Bacillus subtilis* subspecies *inaquosorum*.

3. In Table 2, genome mining for potential secondary metabolites identified eight clusters. To confirm these clusters were functional, HPLC-MS/MS was conducted on culture supernatants in the early stationary phase. Except for sublancin and aurantinin, the analysis was able to confirm the presence of all of the predicted metabolites shown in FIG. 1.

TABLE 2

Biosynthetic clusters of secondary metabolites identified in *Bacillus subtilis* DE111

| Compound | Function |
|---|---|
| Surfactin | Multiple |
| Iturin/Bacillomycin | Antifungal |
| Fengycin | Antifungal |
| Bacillibactin | Siderophore |
| Bacilysin | Antibacterial |
| Subtilosin | Antibacterial |
| Aurantinin | Antibacterial |
| Sublancin | Antibacterial |

Shown in FIG. 1 are extracted ion-chromatograms of secondary metabolites of *Bacillus subtilis* DE111: A) m/z 1022-23, 1036-37, and 1044-45, corresponding to surfactin $[M+H]^+$ components; B) m/z 1085-86, 1099-100, corresponding to Bacillomycin F $[M+H]^+$; C) m/z 746-47, 753-54, 1491-92, 1506-07, corresponding to $[M+2H]^{2+}$ and $[M+H]^+$ fengycins; D) m/z 883-84, corresponding to Bacillibactin $[M+H]^+$; E) m/z 271-72, corresponding to Bacilysin $[M+H]^+$; F) m/z 1135-36, 1701-02, corresponding to Subtilosin $[M+3H]^{3+}$ and $[M+2H]^{2+}$.

C. Discussion

These experiments have further confirmed the identity of the strain DE111 as a strain of *Bacillus subtilis* subspecies *inaquosorum* based on MLSA and core genome phylogeny. *Bacillus subtilis* is divided into three subspecies, namely, *Bacillus subtilis* subspecies *subtilis*, *Bacillus subtilis* subspecies *spizizenii*, and *Bacillus subtilis* subspecies *inaquosorum*, based on multi-gene phylogeny and comparative genomics. See, e.g., L. K. Nakamura, et al., *Relationship of Bacillus subtilis clades associated with strains 168 and W23: a proposal for Bacillus subtilis subsp. subtilis subsp. nov. and Bacillus subtilis subsp. spizizenii subsp. nov.*, 49 INT'L J. SYSTEMATIC BACTERIOLOGY 1211 (1999); A. P. Rooney, et al., *Phylogeny and molecular taxonomy of the Bacillus subtilis species complex and description of Bacillus subtilis subsp. inaquosorum subsp. nov.*, 59 INT'L J. SYSTEMATIC & EVOLUTIONARY MICROBIOLOGY 2429 (2009); H. Yi, et al., *Genomic insights into the taxonomic status of the three subspecies of Bacillus subtilis*, 37 SYSTEMATIC & APPLIED MICROBIOLOGY 95 (2014); each of which is incorporated by reference herein in its entirety. Rooney et al. identified *Bacillus subtilis* subspecies *inaquosorum* using multi-locus phylogenetic analysis from 16S rRNA gene and protein coding gene sequences (gyrA, rpoB, purH, polC, and groEL). Recent studies based on whole genome comparisons and average nucleotide identity ("ANI") suggest *Bacillus subtilis* subspecies *spizizenii* and *Bacillus subtilis* subspecies *inaquosorum* should be promoted to species status based on established ANI guidelines of species delineation. See, e.g., Yi, et al., 2014; P. H. Brito, et al., *Genetic competence drives genome diversity in Bacillus subtilis*, 10 GENOME BIOLOGY & EVOLUTION 108 (2018); each of which is incorporated by reference herein in its entirety.

Furthermore, *Bacillus subtilis* DE111 can produce at least 7 secondary metabolites with known biological activity. See Table 2. These results are consistent with the strong antifungal properties of *Bacillus subtilis* DE111. The fengycin and iturin-family compound reported are well known antifungals produced by members of the *Bacillus subtilis* species complex. See, e.g., C. A. Dunlap, et al., *Genomic analysis and secondary metabolite production in Bacillus amyloliquefaciens AS 43.3: a biocontrol antagonist of Fusarium Head Blight*, 64 BIOLOGICAL CONTROL 166 (2013); C. A. Dunlap, et al., *Genomic analysis of Bacillus subtilis OH 131.1 and coculturing with Cryptococcus flavescens for control of fusarium head blight*, 2 PLANT GENE 1 (2015); each of which is incorporated by reference herein in its entirety. However, this is the first report of these antifungal lipopeptides being produced by a *Bacillus subtilis* DE111. Rooney et al. reported the *Bacillus subtilis* subspecies *inaquosorum* type strain produced surfactin based on MALDI mass spectroscopy but did not report a fengycin or an iturin family compound. Ruiz-Sánchez et al. recently reported on an antifungal-producing *Bacillus subtilis* subspecies *inaquosorum* strain but did not identify the active compounds. See, e.g., E. Ruiz-Sánchez, et al., *Antifungal activity and molecular identification of native strains of Bacillus subtilis*, 50 AGROCIENCIA 133 (2016), incorporated by reference herein in its entirety.

These experiments establish *Bacillus subtilis* DE111 as a producer of bacillomycin F. Bacillomycin F is a rare cyclic lipopeptide that has only been identified in one other strain, since its original description in 1985. Bacillomycin F is much less common than the other iturin family compounds, such as iturin A and bacillomycin D. Only two definitive reports of bacillomycin F producers were found in literature, the original report, and from bacteria isolated from honey.

See, e.g., F. Peypoux, et al., *Structure of bacillomycin F, a new peptidolipid antibiotic of the iturin group*, 153 EUR. J. BIOCHEMISTRY 335 (1985); H. Lee, et al., *Purification and structural characterization of bacillomycin F produced by a bacterial honey isolate active against Byssochlamys fulva H25*, 105 J. APPLIED MICROBIOLOGY 663 (2008); each of which is incorporated by reference herein in its entirety. In comparison, a literature search of "iturin" yields 547 references, and a search of "bacillomycin D" yields 108 references. Both bacillomycin F producer strains were ported to be *Bacillus subtilis* strains, but their specific taxonomic placement remains uncertain. The original report describing bacillomycin F used *Bacillus subtilis* 1164 and how its taxonomic assignment was determined is unclear. See, e.g., F. Peypoux, et al., 1985. There is also no sequence data available for this strain in GenBank. The other known producer was only identified using 16S rRNA sequencing, which is not always reliable for taxonomic assignment within the *Bacillus subtilis* group. See, e.g., A. P. Rooney, et al., 2009. While it is likely that the two previously known producers were *Bacillus subtilis* strains, it is unclear what subspecies they would belong to.

This study also establishes *Bacillus subtilis* DE111 as a producer of fengycins. Fengycins, also known as plipastatins, have been reported in many strains of *Bacillus* spp. See, e.g., H. Fan, et al., *Fengycin produced by Bacillus subtilis 9407 plays a major role in the biocontrol of apple ring rot disease*, 199 MICROBIOLOGICAL RESEARCH 89 (2017), incorporated by reference herein in its entirety. Fengycins are often reported in strains isolated as antagonists of plant pathogenic fungi and have also been identified in strains that have other biotechnical applications, such as enhanced oil recovery and bioremediation. See, e.g., F. Cheng, et al., *Characterization of a blend-biosurfactant of glycolipid and lipopeptide produced by Bacillus subtilis TU2 isolated from underground oil-extraction wastewater*, 3 J. MICROBIOLOGY & BIOTECHNOLOGY 115 (2008), incorporated by reference herein in its entirety. In addition to the antifungal metabolites, *Bacillus subtilis* DE111 produced several known antibacterials. The strain was found to contain four antibacterial clusters: bacilysin, subtilosin, aurantinin, and sublancin. See Table 2. Except for sublancin and aurantinin, HPLC-MS was able to confirm the production of antibacterial clusters. See FIG. 1. Bacilysin is a non-ribosomally produced dipeptide-based antibacterial with activity against a wide range of bacteria and some yeasts. See, e.g., G. Özcengiz & İ. Öğülür, *Biochemistry, genetics and regulation of bacilysin biosynthesis and its significance more than an antibiotic*, 32 NEW BIOTECHNOLOGY 612 (2015), incorporated by reference herein in its entirety. The production of bacilysin is commonly reported among strains from the *Bacillus subtilis* group that have been identified as having biocontrol activities. See, e.g., Dunlap et al., 2013; S. Chung, et al., *Isolation and partial characterization of Bacillus subtilis ME488 for suppression of soilborne pathogens of cucumber and pepper*, 80 APPLIED MICROBIOLOGY & BIOTECHNOLOGY 115 (2008); K. Kobayashi, *Plant methyl salicylate induces defense responses in the rhizobacterium Bacillus subtilis*, 17 ENVIRONMENTAL MICROBIOLOGY 1365 (2015); L. Wu, et al., *Difficidin and bacilysin from Bacillus amyloliquefaciens FZB42 have antibacterial activity against Xanthomonasoryzae rice pathogens*, 5 SCIENTIFIC REPORTS 12975 (2015); each of which is incorporated by reference herein in its entirety. Subtilosin belongs to the class of antibacterials known as bacteriocins, which comprise one of the most common classes of antibacterials reported. See, e.g., M. A. Riley & J. E. Wertz, *Bacteriocin diversity: ecological and evolutionary perspectives*, 84 BIOCHIMIE 357 (2002), incorporated by reference herein in its entirety. Bacteriocins are thought to play an important role in microbial communities that overlap ecological niches. See, e.g., H. Hawlena, et al., *Bacteriocin-mediated interactions within and between coexisting species*, 2 ECOLOGY & EVOLUTION 2516 (2012), incorporated by reference herein in its entirety. This is based, in part, on bacteriocins often having activity against closely related members of the population (e.g., other *Bacillus* spp.) that would likely occupy the same ecological niche. See, e.g., M. A. Riley & J. E. Wertz, 2002.

Interestingly, sublancin was also identified. However, the cluster was not observed as a metabolite in the supernatant. Sublancin belongs to a class of antibacterials known as glycocins (glycosylated bacteriocins) that are ribosomally produced peptides that undergo a series of post-translational modifications that include an S-linked glycosylation of a cysteine side chain. See, e.g., G. E. Norris & M. L. Patchett, *The glycocins: in a class of their own*, 40 CURRENT OPINION IN STRUCTURAL BIOLOGY 112 (2016), incorporated by reference herein in its entirety. Because the peptide is ribosomally produced, the cluster contains no mutations in the parent peptide sequence. This suggests that the cluster is likely functional and just not expressed under the conditions of the experiments performed. It has been previously reported for other *Bacillus subtilis* strains that sublancin is poorly expressed in standard culture conditions. See, e.g., S. Ji, et al., *Improved production of sublancin via introduction of three characteristic promoters into operon clusters responsible for this novel distinct glycopeptide biosynthesis*, MICROBIAL CELL FACTORIES 14 (2015), incorporated by reference herein in its entirety. On the other hand, it may also be expressed, but contains post translational modifications that result in changes in the anticipated molecular weight of the parent ion of the compound. This would prevent identification in the supernatant, because the parent ion mass is the goal of detection. The problem is compounded by the parent ion likely having multiple charges under these conditions, which may make some mass changes to the parent ion difficult to observe or accurately predict.

Only one study that reported lipopeptide production by a known probiotic strain was identified. *Bacillus subtilis* strain PB6 was shown to secrete surfactins, which can inhibit phospholipase A2, a key enzyme in inflammation response in humans. The authors speculated this inhibition is responsible for the subsequent downregulation of pro-inflammatory cytokines and upregulation of anti-inflammatory cytokines in humans receiving the probiotic strain. See, e.g., R. Selvam, et al., *Effect of Bacillus subtilis PB6, a natural probiotic on colon mucosal inflammation and plasma cytokines levels in inflammatory bowel disease*, 46 INDIAN J. BIOCHEMISTRY & BIOPHYSICS 79 (2009), incorporated by reference herein in its entirety. If this is an important mode of action for probiotics, *Bacillus subtilis* DE111 may also be able to mediate these interactions through lipopeptide secretion. In the current study, we show the *Bacillus subtilis* DE111 also makes fengycins, which are also known inhibitors of phospholipase A2. See, e.g., L. Volpon, et al., *NMR structure of antibiotics plipastatins A and B from Bacillus subtilis inhibitors of phospholipase A2*, 485 FEBS LETTERS 76 (2000), incorporated by reference herein in its entirety. These findings support approaches that have been used to characterize *Bacillus* strains as potent and efficacious probiotics.

Example 2

Bacillus subtilis DE111 Microbial Inhibition

Introduction

The purpose of this study was to determine the antimicrobial properties of Bacillus subtilis DE111 on Escherichia coli (E. coli). See, e.g., Magdalena Moryl, et al., Antimicrobial, antiadhesive and antibiofilm potential of lipopeptides synthesized by Bacillus subtilis, on uropathogenic bacteria, 62 ACTA BIOCHIMICA POLONICA 725 (2015), incorporated by reference herein in its entirety.

Method

An E. coli isolate was streaked onto two nutrient agar plates. 1 milliliter of a Bacillus subtilis DE111 bacterial suspension was deposited onto the surface of one of the streaked plates. The plates were then incubated for 24 hours at 37° C. and growth of E. coli and Bacillus subtilis DE11 was observed in order to determine bacterial growth of Bacillus subtilis DE111 and inhibition of E. coli.

Results

Figure 2:
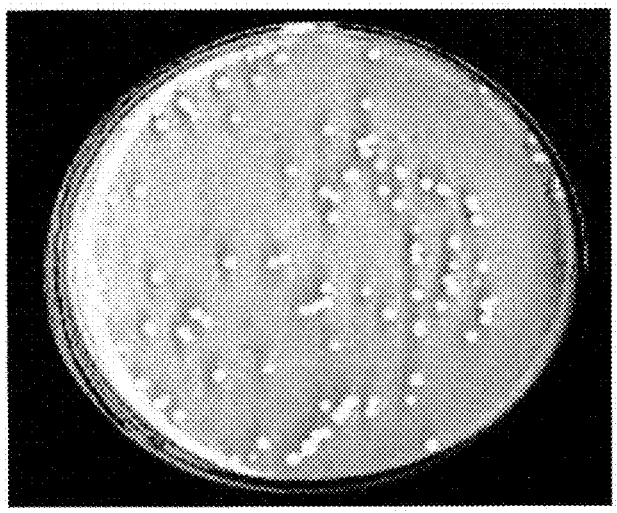
FIG. 2 depicts pictures of a nutrient plate (left); *E. coli* lawn on a nutrient plate (center); and *Bacillus subtilis* DE111 culture growing on the *E. coli* lawn on a nutrient plate (right).
Figure 2:
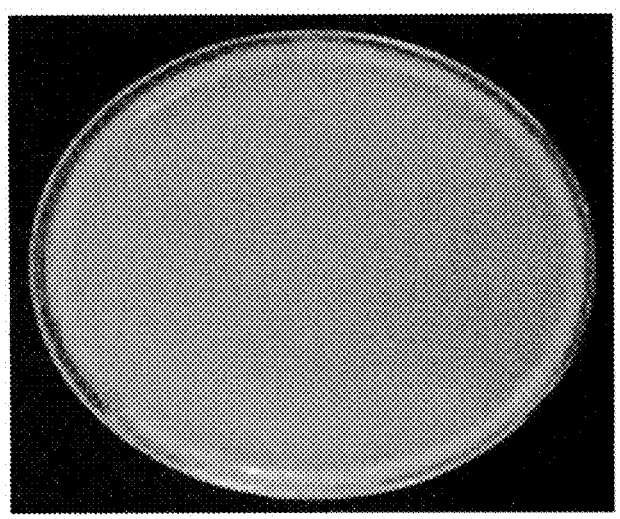
Figure 2:
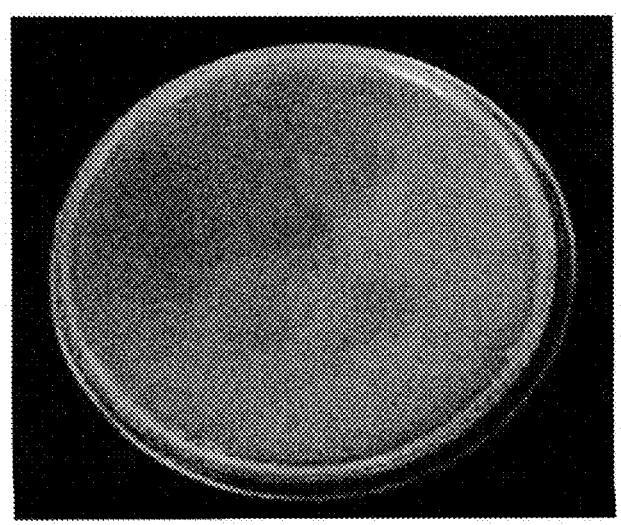

After 24 hours E. coli growth was reduced, as the growth of Bacillus subtilis DE111 was observed, as shown in FIG. 2 below. FIG. 2, left panel, shows the nutrient plate. FIG. 2, center panel, shows the E. coli lawn. Finally, FIG. 2, right panel, shows Bacillus subtilis DE111 growing on the E. coli lawn.

Conclusion

The in vitro study performed confirmed the hypothesis that Bacillus subtilis DE111 contains antimicrobial properties against bacteria, specifically E. coli. Additional studies to confirm the amount of inhibition from Bacillus subtilis DE111 on E. coli are recommended for further research.

Example 3

Profiling of Bacillus Strains' Antimicrobial Activity

Study Objectives

First, Bacillus strains were grown in a panel of media for comparison.

Screen Bacillus strains antimicrobial activity against pathogen strains Escherichia coli 25922, Salmonella enteritidis 13076, Staphylococcus aureus RF122, P. aeruginosa DSM3227, and C. acnes DSM1897.

Bacillus strains to be tested: Bacillus subtilis DE111, Bacillus coagulans CGI314, Bacillus clausii CSI08, and Bacillus megaterium MIT411.

Without intending to be bound by any theory, the following background theory is described.

Increased levels of multidrug-resistant bacteria observed in the last decades has resulted in an urgent need for new antimicrobial agents. For this reason, discovery of new antibiotics or natural alternative products such as probiotics is an important objective. Natural products are still one of the major sources of new drug molecules today, deriving from prokaryotic bacteria, eukaryotic microorganisms, plants and various animal organisms. Microbial and plant products provide the majority of the antimicrobial compounds discovered until now. A variety of laboratory methods can be used to evaluate or screen the in vitro antimicrobial activity of an extract, a pure compound, or a microorganism.

The most well-known and basic methods for that are the disk-diffusion and broth or agar dilution methods.

Agar disk-diffusion testing was developed in 1940, and still remains as the official method for many clinical microbiology laboratories for routine antimicrobial susceptibility testing. For this procedure, agar plates are inoculated with a standardized inoculum of the test microorganism. Then, filter paper discs (about 6 mm in diameter), containing the test compound at a desired concentration, are placed on the agar surface. The Petri dishes are incubated under suitable conditions. Generally, antimicrobial agent diffuses into the agar and inhibits germination and growth of the test microorganism and then the diameters of inhibition growth zones are measured.

Figure 3:
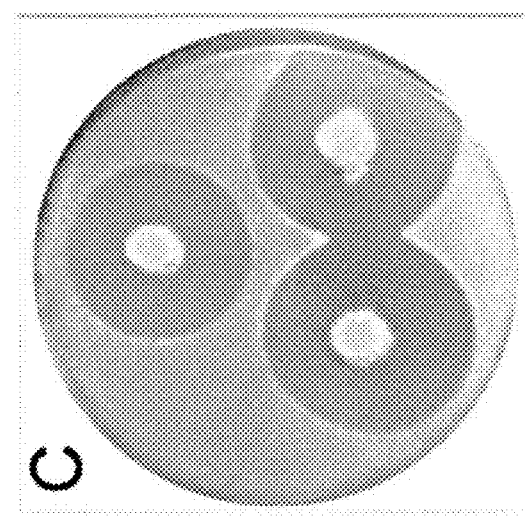
FIG. 3 depicts a modified agar disk-diffusion test for microbial antagonism where a test strain is inoculated in the centre of the plate (C) and challenged with a pathogen, as a control. After incubation, the antimicrobial activity of the microbial secreted molecules is detected by the appearance of the inhibition zone around the area were the test bacteria grew.

This method can be modified to test microbial antagonism where a test strain is inoculated in the centre of the plate (C) and challenged with a pathogen. During their growth, the test strains will secrete molecules which diffuse in the agar medium around them. After incubation, the antimicrobial activity of the microbial secreted molecules is detected by the appearance of the inhibition zone around the area were the test bacteria grew (FIG. 3).

Comparison of Bacillus Strains Growth in a Panel of Growth Media

Figure 4:
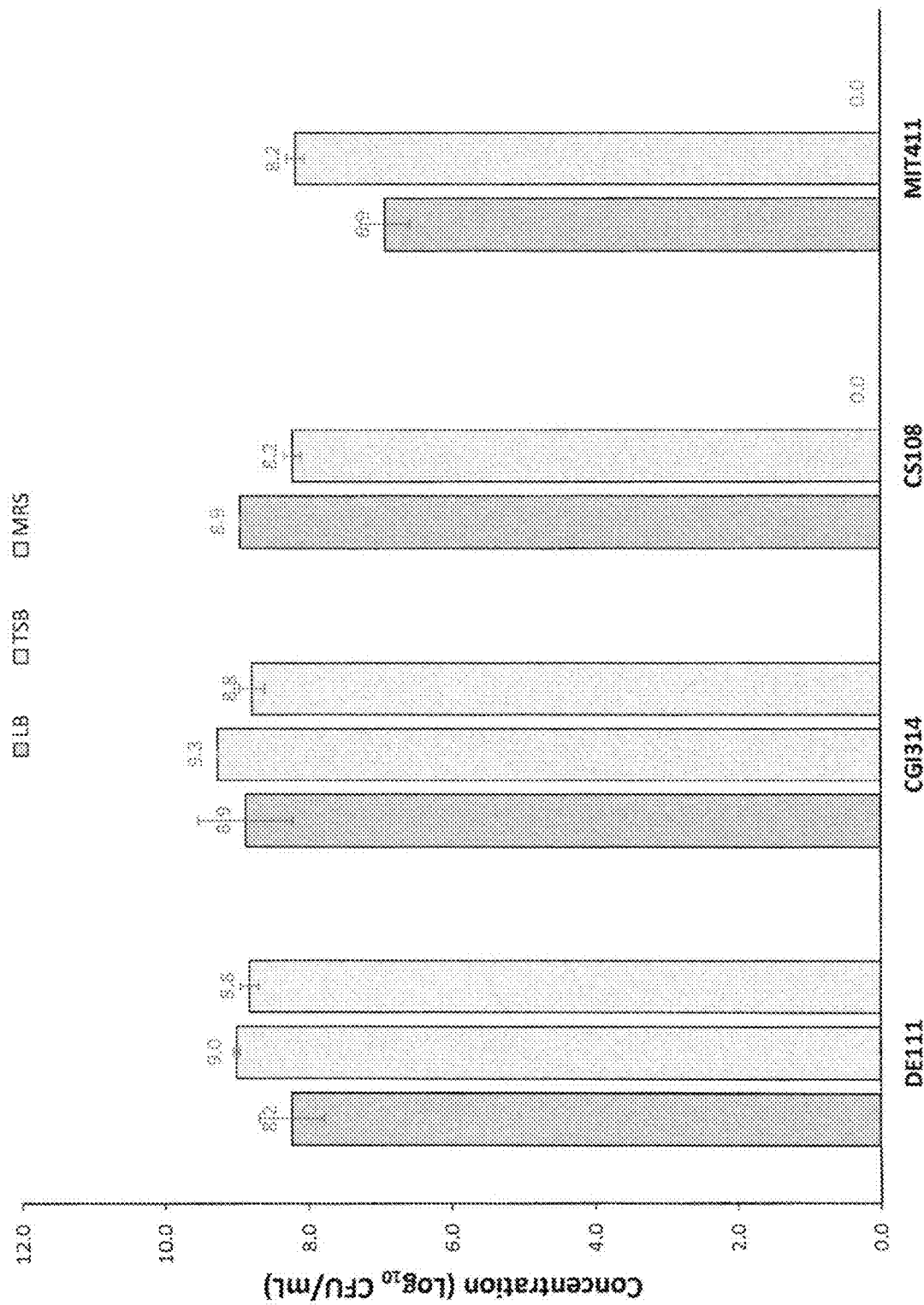
FIG. 4 depicts concentration (in $\log_{10}$ CFU/mL) of *Bacillus subtilis* DE111 (bars left to right: LB, TSB and MRS), *Bacillus coagulans* CGI314 (bars left to right: LB, TSB and MRS), *Bacillus clausii* CSI08 and *Bacillus megaterium* MIT411 (bars left to right: LB and TSB) after 24 h growth in LB, TSB or MRS broth respectively (n=3±standard deviation).

As shown in FIG. 4, several different strains of Bacillus, namely Bacillus subtilis DE111 (LB, TSB, and MRS), Bacillus coagulans CGI314 (LB, TSB, and MRS), Bacillus clausii CSI08 and Bacillus megaterium MIT411 (both LB and TSB), were grown in three different types of agar (LB, TSB, and MRS) for 24 hours.

1. Antimicrobial testing of Bacillus strains in MRS Agar

Figure 5:
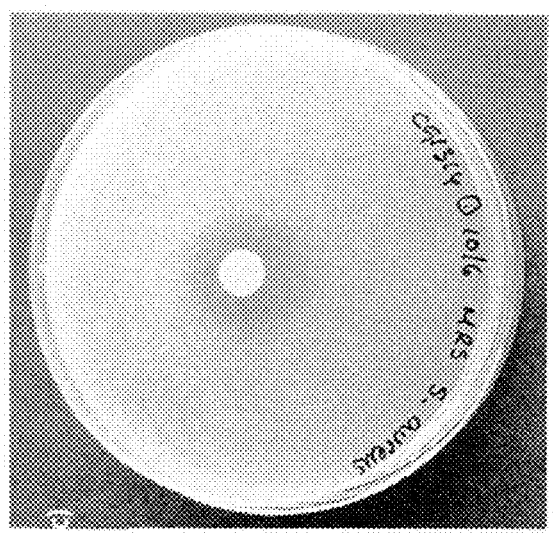
FIG. 5 depicts antimicrobial activity of CG314 inoculated on MRS agar against (a) *E. coli*, (b) *S. enteritidis* and (c) *S. aureus* 0.8% LB agar overlay plates in a photograph.
Figure 5:
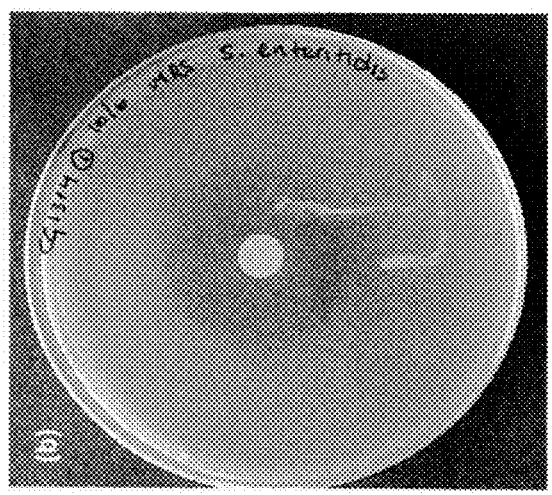
Figure 5:
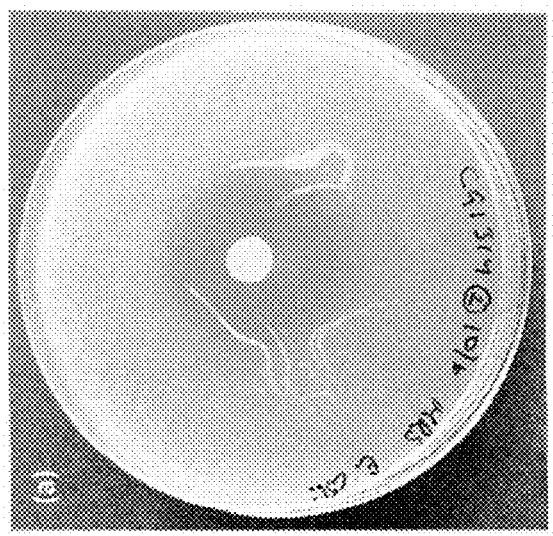

As shown in FIG. 5, CGI314 had strong antimicrobial activity against all pathogen strains tested using MRS agar (FIG. 5 and Table 3). CSI08, DE111 and MIT411 had no detectable antimicrobial activity when tested using MRS agar.

TABLE 3

| Probiotic strain | Zone of inhibition diameter (mm) | | |
|---|---|---|---|
| | E. coli | S. enteritidis | S. aureus |
| DE111 | — | — | — |
| CGI314 | 28.60 ± 4.10 | 33.40 ± 4.28 | 20.67 ± 0.58 |
| CSI08 | — | — | — |
| MIT411 | — | — | — |

Table 3 above shows probiotic strains' antimicrobial activity against E. coli, S. enteritidis and S. aureus. Values represent average inhibition±standard deviation (E. coli and S. enteritidis n=5, S. aureus n=3).

It was not possible to tests antimicrobial activity against P. aeruginosa and C. acnes using MRS broth as these strains do not grow in this medium.

2. Antimicrobial Testing of Bacillus Strains in LB Agar

Using LB agar there was no evidence of antimicrobial activity by Bacillus strains against the panel of pathogens tested. Poor growth of CGI314, CSI08 and MIT411 on the LB agar plates was observed.

3. Antimicrobial Testing of Bacillus Strains in TSB Agar

CGI314 had no antimicrobial activity against the panel of pathogens when tested using TSB.

Figure 6:
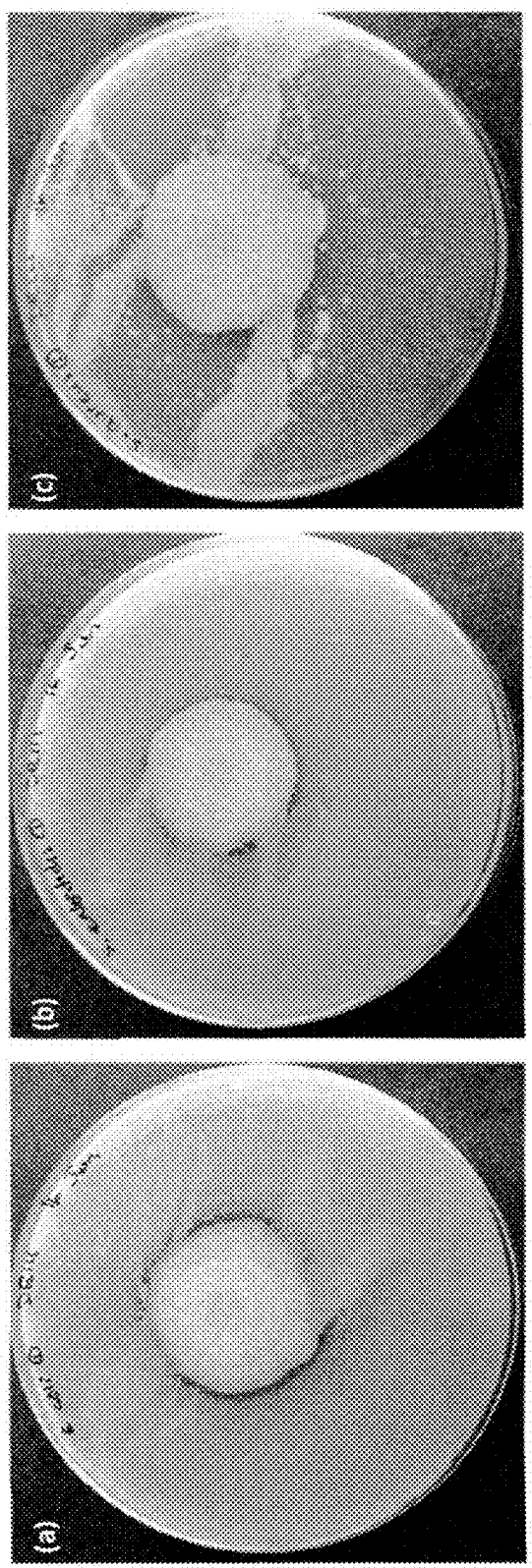
FIG. 6 depicts antimicrobial activity of DE111 inoculated on TSB agar against (a) *E. coli*, (b) *S. enteritidis* and (c) *S. aureus*.
Figure 9:
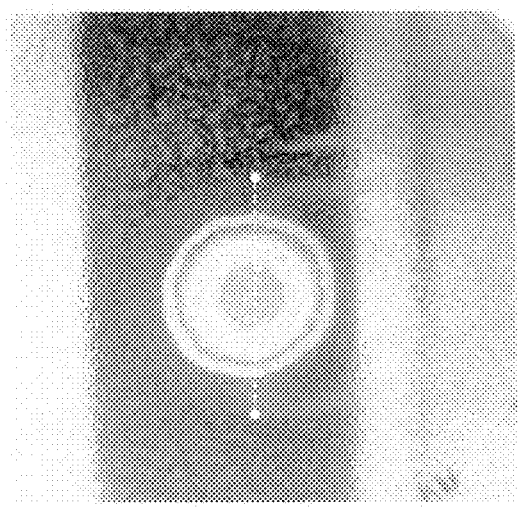
FIG. 9 depicts *B. subtilis* DE111 antimicrobial activity inoculated on TSB agar against *P. aeruginosa* DSM3227.

DE111 had potent antimicrobial activity against the pathogen strains tested, with a clearance zone seen around the rapidly expanding area of DE111 growth (FIG. 6). In addition, DE111 showed activity against P. aeruginosa (DSM3227) and C. acnes (DSM1897) using this medium (Table 4 and FIG. 9).

Figure 7:
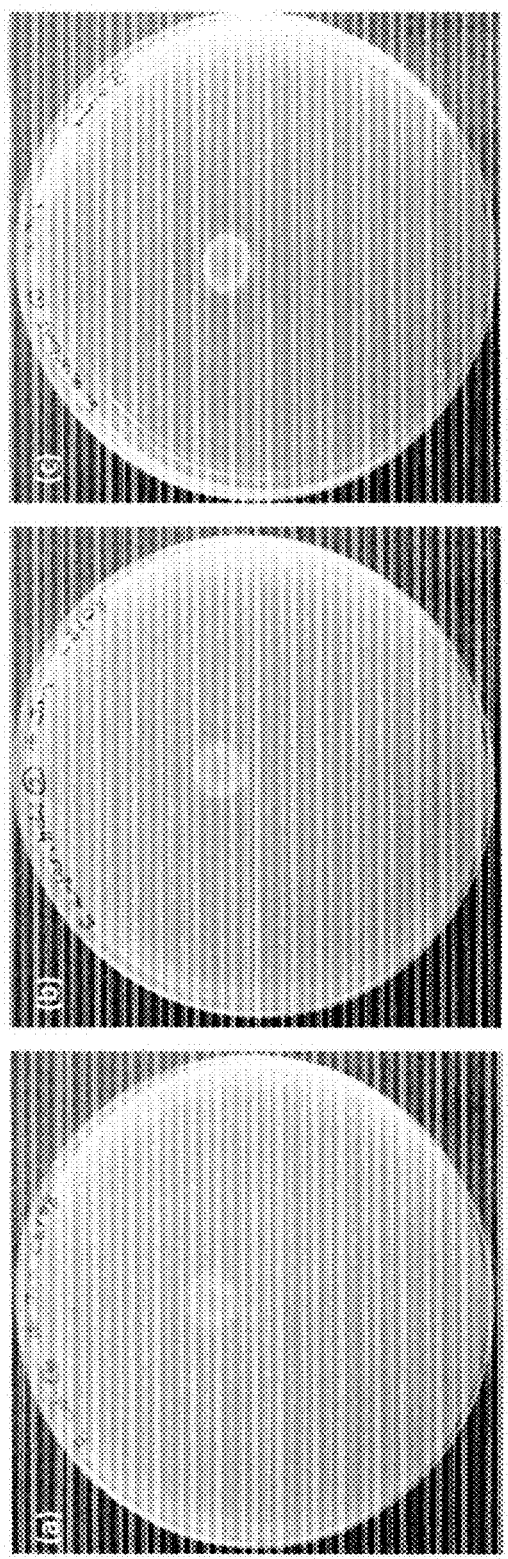
FIG. 7 depicts antimicrobial activity of CSI08 inoculated on TSB agar against (a) *E. coli*, (b) *S. enteritidis* and (c) *S. aureus*.

CSI08 had weak antimicrobial activity, with an inhibition of S. enteritidis and S. aureus growth seen in a hazy zone (FIG. 7).

Figure 8:
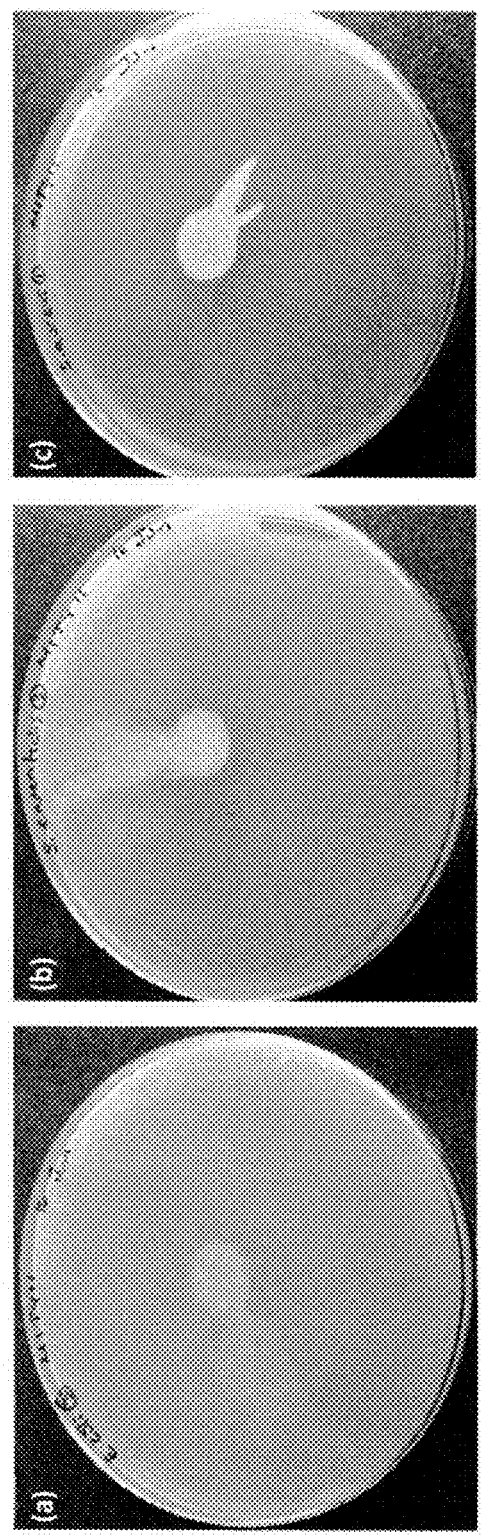
FIG. 8 depicts antimicrobial activity of MIT411 inoculated on TSB agar against (a) *E. coli*, (b) *S. enteritidis* and (c) *S. aureus*.

MIT411 had weak antimicrobial activity, with an inhibition of pathogen growth seen in a hazy zone (FIG. 8).

Table 4 below summarizes the antimicrobial activity of the strains tested.

TABLE 4

| Probiotic strain | Zone of inhibition diameter (mm) | | | | |
| --- | --- | --- | --- | --- | --- |
| | E. coli | S. enteritidis | S. aureus | P. aeruginosa | C. acnes |
| DE111 | 40.7 ± 3.3 | 35.7 ± 1.5 | 37.25 ± 0.5 | 30.6 ± 0.6 | 28 ± 1.0 |
| CGI314 | — | — | — | — | — |
| CSI08 | — | 15 ± 0.00 | 14.7 ± 0.58 | — | — |
| MIT411 | 18.9 ± 0.9 | 18.7 ± 1.2 | 18.67 ± 0.58 | — | — |

Table 4 above shows probiotic strains' antimicrobial activity against *E. coli, S. enteritidis, S. aureus* and *P. aeruginosa*. Values represent average inhibition±standard deviation (n=3).

4. Antimicrobial Testing of *Bacillus* Strains in BHI Agar

Figure 10:
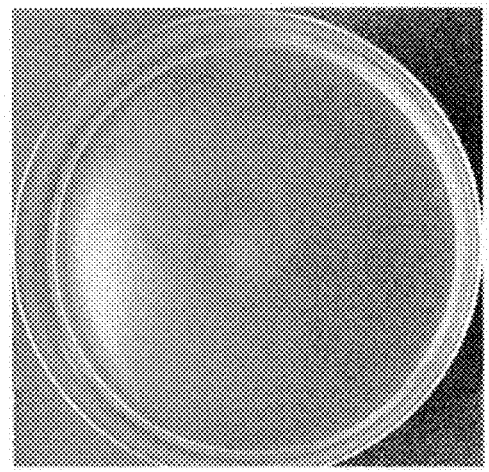
FIG. 10 depicts *B. subtilis* DE111 antimicrobial activity inoculated on BHI agar against *C. acnes* DSM1897.

Antimicrobial activity against *C. acnes* had to be tested in its optimal growth media (BHI). In these conditions, only DE111 showed antimicrobial activity against it (Table 5 and FIG. 10).

TABLE 5

| Probiotic strain | Zone of inhibition diameter (mm) C. acnes |
| --- | --- |
| DE111 | 28 ± 1.0 |
| CGI314 | — |
| CSI08 | — |
| MIT411 | — |

Table 5 above shows probiotic strains' antimicrobial activity against *C. acnes*. Values represent average inhibition±standard deviation (n=3).

In conclusion, MIT411 grew poorly in LB broth. When compared to LB broth, DE111, CGI314 and MIT411 had improved growth in TSB broth. CSI08 and MIT411 did not grow in MRS broth. *Bacillus* strains inoculated on LB agar had no antimicrobial activity against the pathogens tested.

CGI314 showed antimicrobial activity against all pathogens tested when inoculated on MRS agar. However, the other *Bacillus* strains did not demonstrate antimicrobial activity on MRS agar.

DE111, CSI08 and MIT411 demonstrated differential antimicrobial activity against the pathogens tested when inoculated on TSB agar. CGI314 had no antimicrobial activity on TSB agar.

Only DE111 had antimicrobial activity against *P. aeruginosa* and *C. acnes*.

These results show that CGI314 requires MRS agar to produce its antimicrobial activity. Whereas DE111, MIT411 and CSI08 require TSB agar to produce antimicrobials. This suggests that the antimicrobial activity of each *Bacillus* strain is driven by the presence of particular nutrients.

The differential growth of the strains in the media panel suggests that different nutrient backgrounds will be necessary for efficient growth and antimicrobial production.

Example 4

Antimicrobial Activity—Anti-Adherence

Study Objectives

This study was conducted to test *Bacillus subtilis* DE111, *B. coagulans* CGI314, *B. clausii* CSI08 and *B. megaterium* MIT411 cell-free suspensions for surface anti-adherence properties against *Escherichia coli* 25922, *Salmonella enteritidis* 13076, *Staphylococcus aureus* RF122, and *Pseudomonas aeruginosa* DSMZ 3227.

Without intending to be bound by any theory, the following background theory is described.

Biofilms are formed when microorganisms attach to wet surfaces, start multiplying and embed themselves in matrix composed of extracellular polymeric substances (EPS). A biofilm serves as a protection mechanism from hostile environments, and this often means that microorganisms will form them to combat, starvation, preservatives, disinfectants, antibiotics, or biocides. Therefore, biofilms are problematic for food industry and hospitals, where they may cause recurrent contaminations and chronic infections.

In one scenario, biofilms may form and develop in the following manner, proceeding from one stage to the next: 1. single floating planktonic cells, 2. cell-cell aggregation, 3. adhesion to a matrix or surface, 4. growth and maturation, and 5. detachment and dispersion. A matrix may comprise one or more components including polysaccharides, proteins, DNA, ergosterol, lipid membranes, and the like.

Probiotic strains can produce various molecules to effectively reduce biofilm formation and/or adherence on surfaces. Some of these mechanisms include the secretion of antagonistic substances (e.g., surfactants, bacteriocins, exopolysaccharides), anti-adhesion factors, organic acids, lactic acid, fatty acids, enzymes (amylase, lipase) and hydrogen peroxide. These probiotics can also control the presence of biofilms by pH alteration or competitive exclusion, giving unfavourable environmental conditions for pathogens (e.g., pH alteration as well as competition for surface and nutrients).

In short, probiotic species and the molecules they produce can be used to interfere with the adherence of pathogenic bacteria to surfaces. Furthermore, it has been shown herein that probiotics were effective to prevent adherence.

1. *Bacillus* Spores Anti-Adherence Activity Against *E. coli*

A. Adherence Prevention Properties

Figure 11:
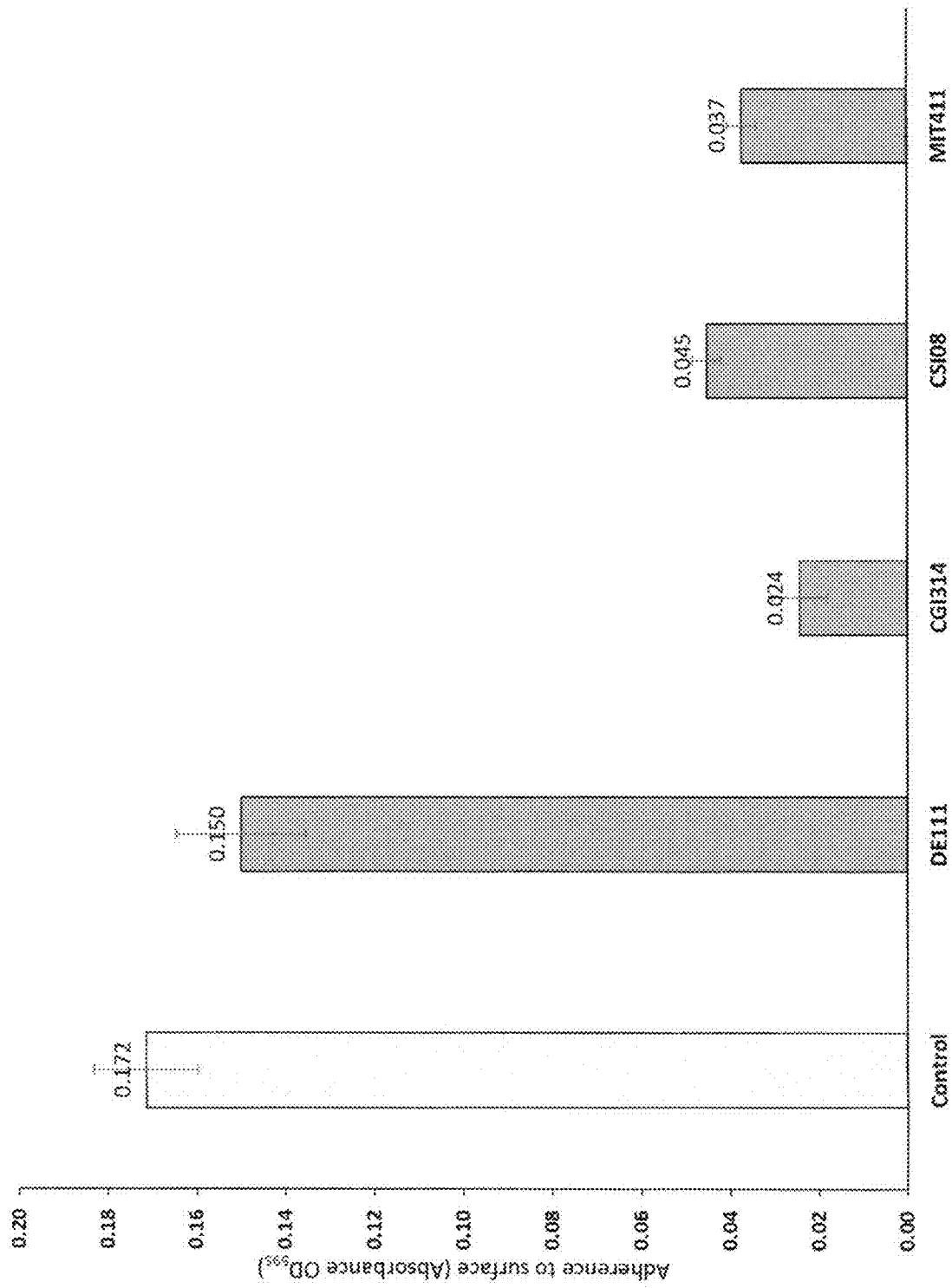
FIG. 11 depicts anti-adherence properties, specifically adherence prevention, of *Bacillus subtilis* DE111, *Bacillus coagulans* CGI314, *Bacillus clausii* CSI08 and *Bacillus megaterium* MIT411 against *E. coli*. Values represent average adherence n=9±standard error. ***P<0.001. Adherance to surfaces was measured as Absorbance $OD_{595}$.

As shown in FIG. 11, CGI314, CSI08 and MIT411 were significantly active in the prevention of *E. coli* adherence. DE111 did not show significant anti-adherence properties against *E. coli*.

B. Adherence Disruption Properties

Figure 12:
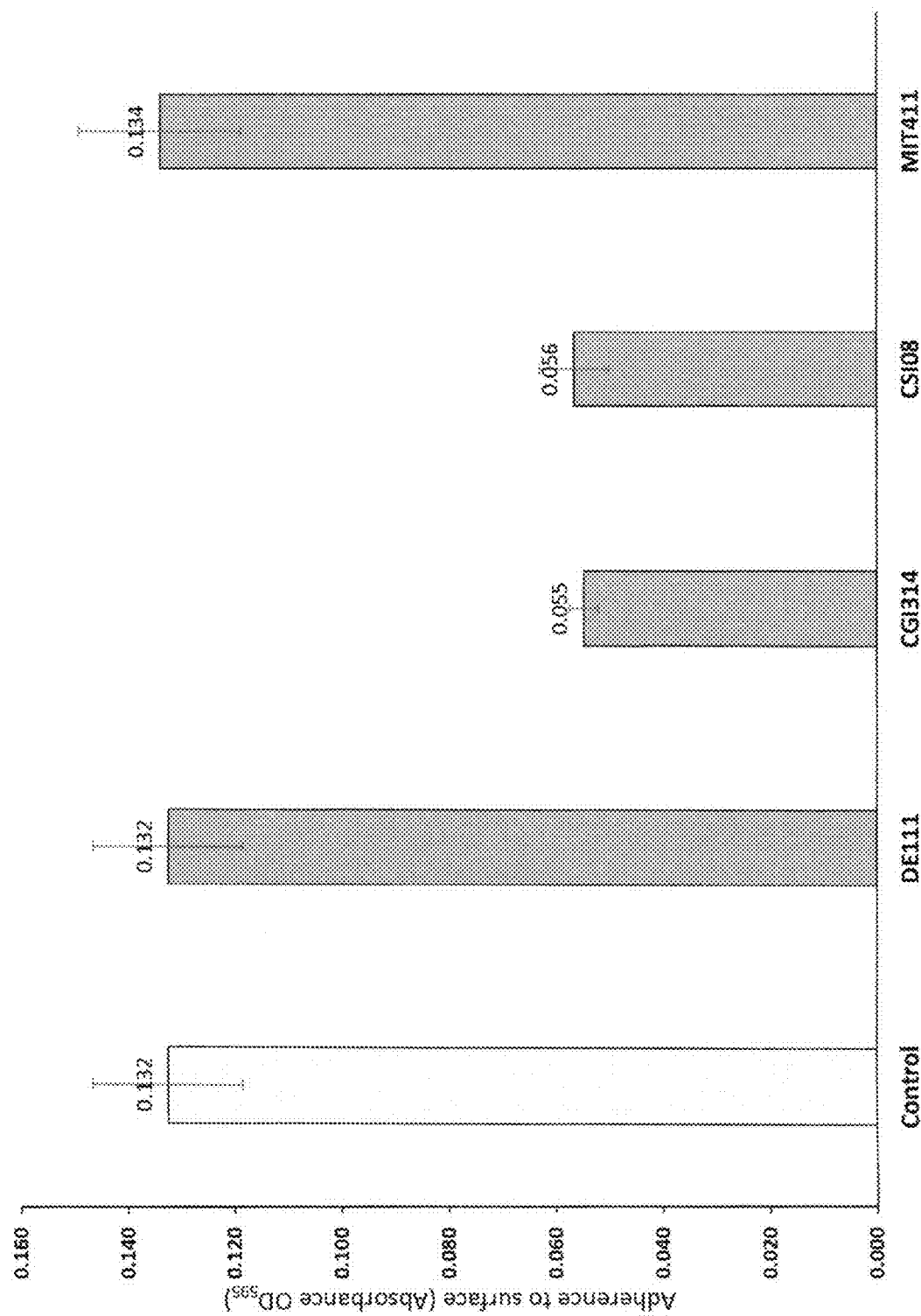
FIG. 12 depicts anti-adherence properties, specifically adherence disruption, of *Bacillus subtilis* DE111, *Bacillus coagulans* CGI314, *Bacillus clausii* CSI08 and *Bacillus megaterium* MIT411 against *E. coli*. Values represent average adherence n=9±standard error. **P<0.01. Adherance to surfaces was measured as Absorbance $OD_{595}$.

As shown in FIG. 12, only the strains CGI314 and CSI08 were able to disrupt the *E. coli* cells adhered to the surfaces.

2. *Bacillus* Spores Anti-Adherence Activity Against *Salmonella*

A. Adherence Prevention Properties

Figure 13:
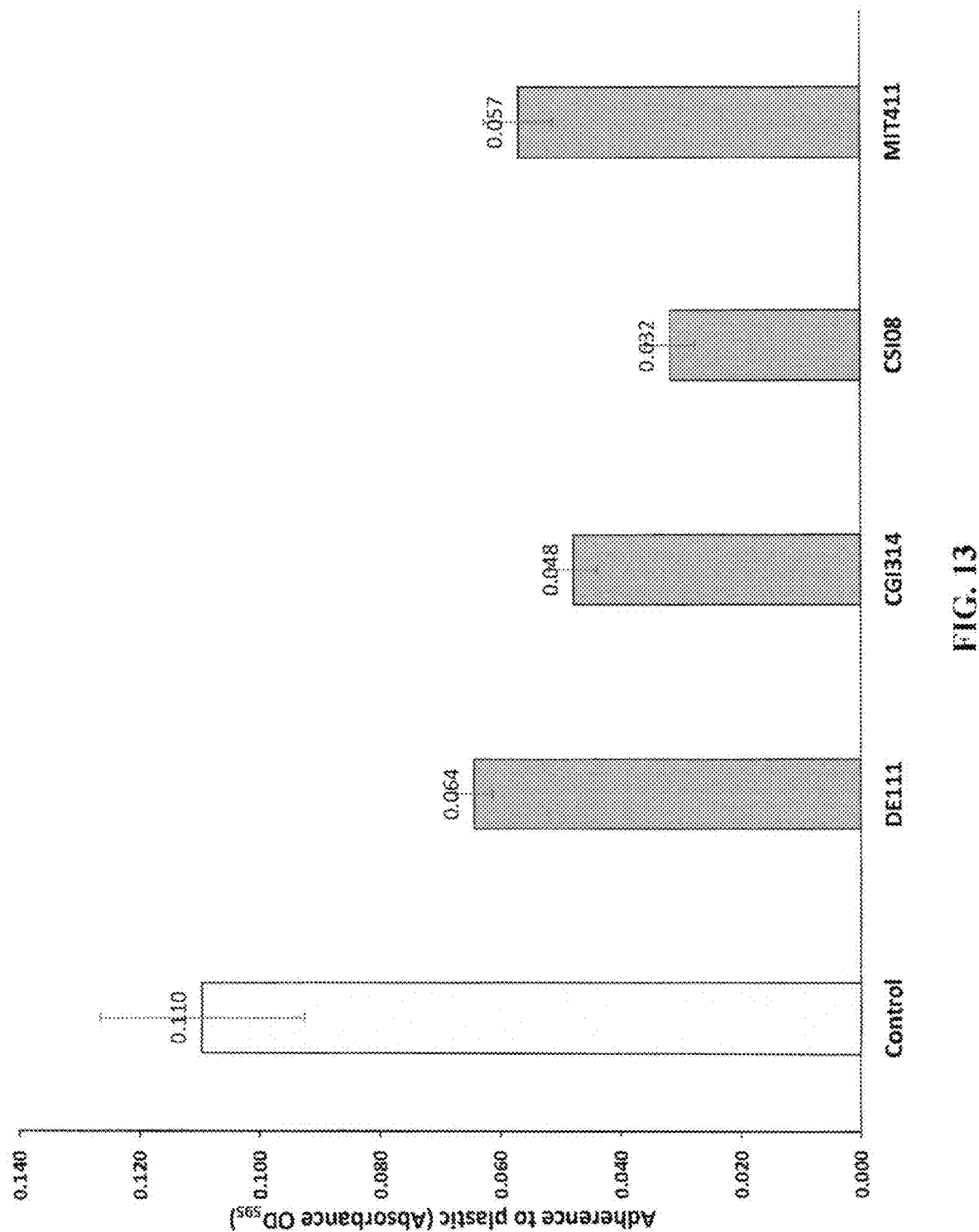
FIG. 13 depicts anti-adherence properties, specifically adherence prevention, of *Bacillus subtilis* DE111, *Bacillus coagulans* CGI314, *Bacillus clausii* CSI08 and *Bacillus megaterium* MIT411 against *Salmonella*. Values represent average adherence n=9±standard error. **P<0.01, *P<0.05. Adherance to surfaces was measured as Absorbance $OD_{595}$.

As shown in FIG. 13, all probiotic strains tested were effective in reducing *Salmonella* adherence, including DE111.

B. Adherence Disruption Properties

Figure 14:
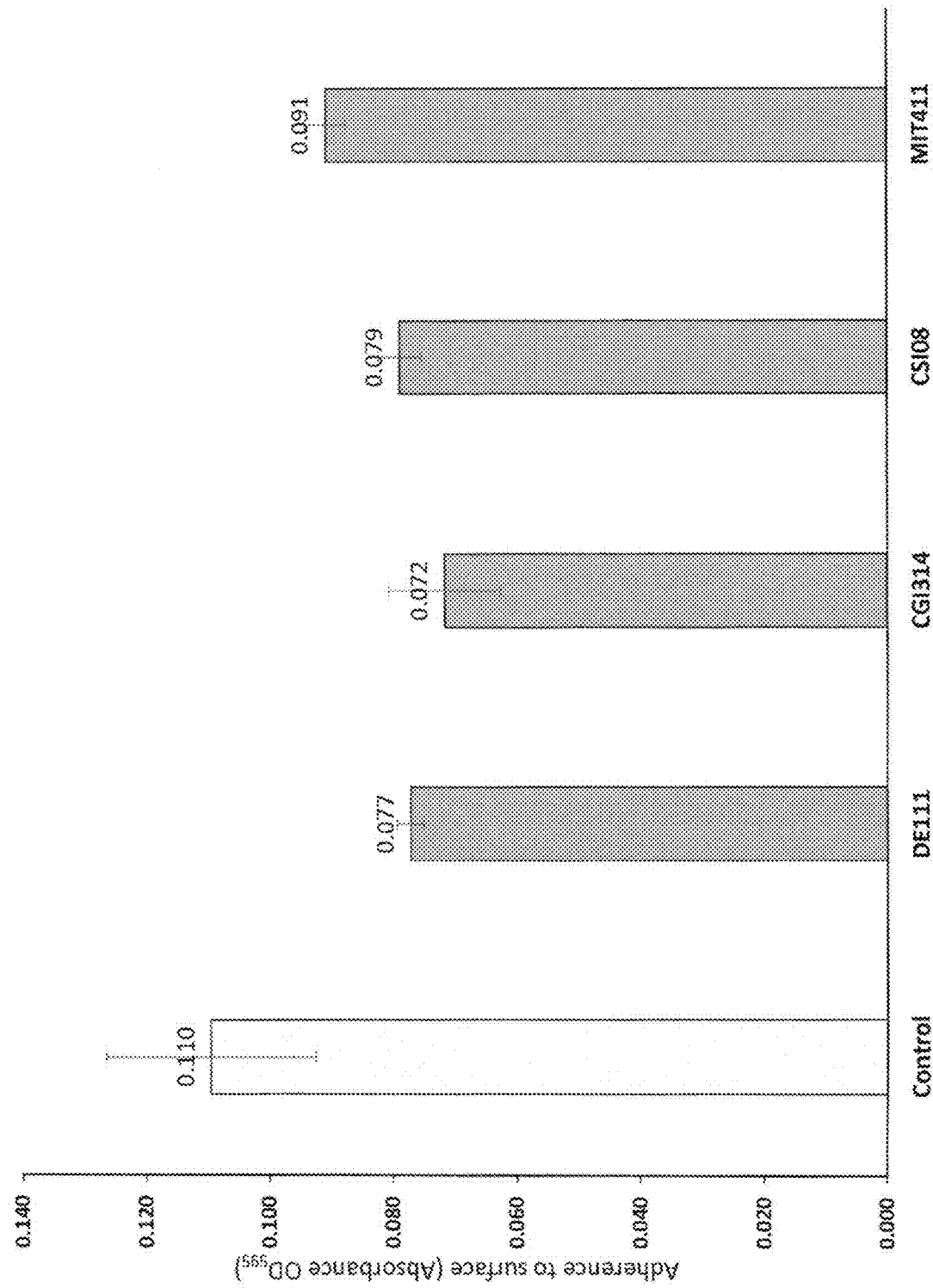
FIG. 14 depicts anti-adherence properties, specifically adherence disruption, of *Bacillus subtilis* DE111, *Bacillus coagulans* CGI314, *Bacillus clausii* CSI08 and *Bacillus megaterium* MIT411 against *Salmonella*. Values represent average adherence n=9±standard error. *P<0.001, P<0.01, *P<0.05. Adherance to surfaces was measured as Absorbance $OD_{595}$.

As shown in FIG. 14, all of the strains except for MIT411 disrupted the biofilms formed by *Salmonella*.

3. *Bacillus* Spores Anti-Adherence Activity Against *Pseudomonas aeruginosa*

A. Adherence Prevention Properties

Figure 15:
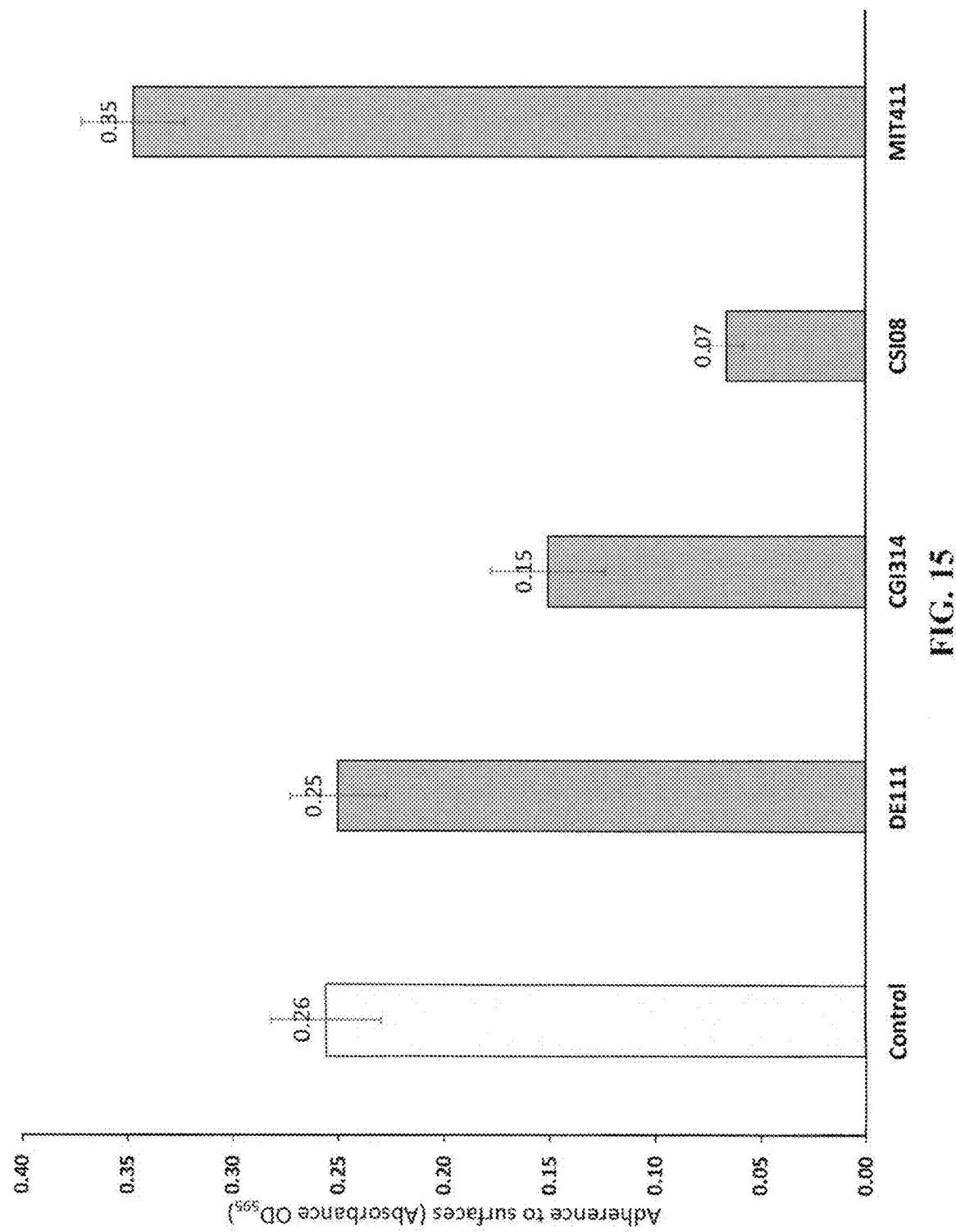
FIG. 15 depicts depicts anti-adherence properties, specifically adherence prevention, of *Bacillus subtilis* DE111, *Bacillus coagulans* CGI314, *Bacillus clausii* CSI08 and *Bacillus megaterium* MIT411 against *P. aeruginosa*. Values represent average adherence n=9±standard error. **P<0.01, *P<0.05. Adherance to surfaces was measured as Absorbance $OD_{595}$.

As shown in FIG. 15, CGI314 and CSI08 were able to prevent the adherence of *P. aeruginosa* to surfaces. Conversely, DE111 and MIT411 did not have any effect.

B. Adherence Disruption Properties

Figure 16:
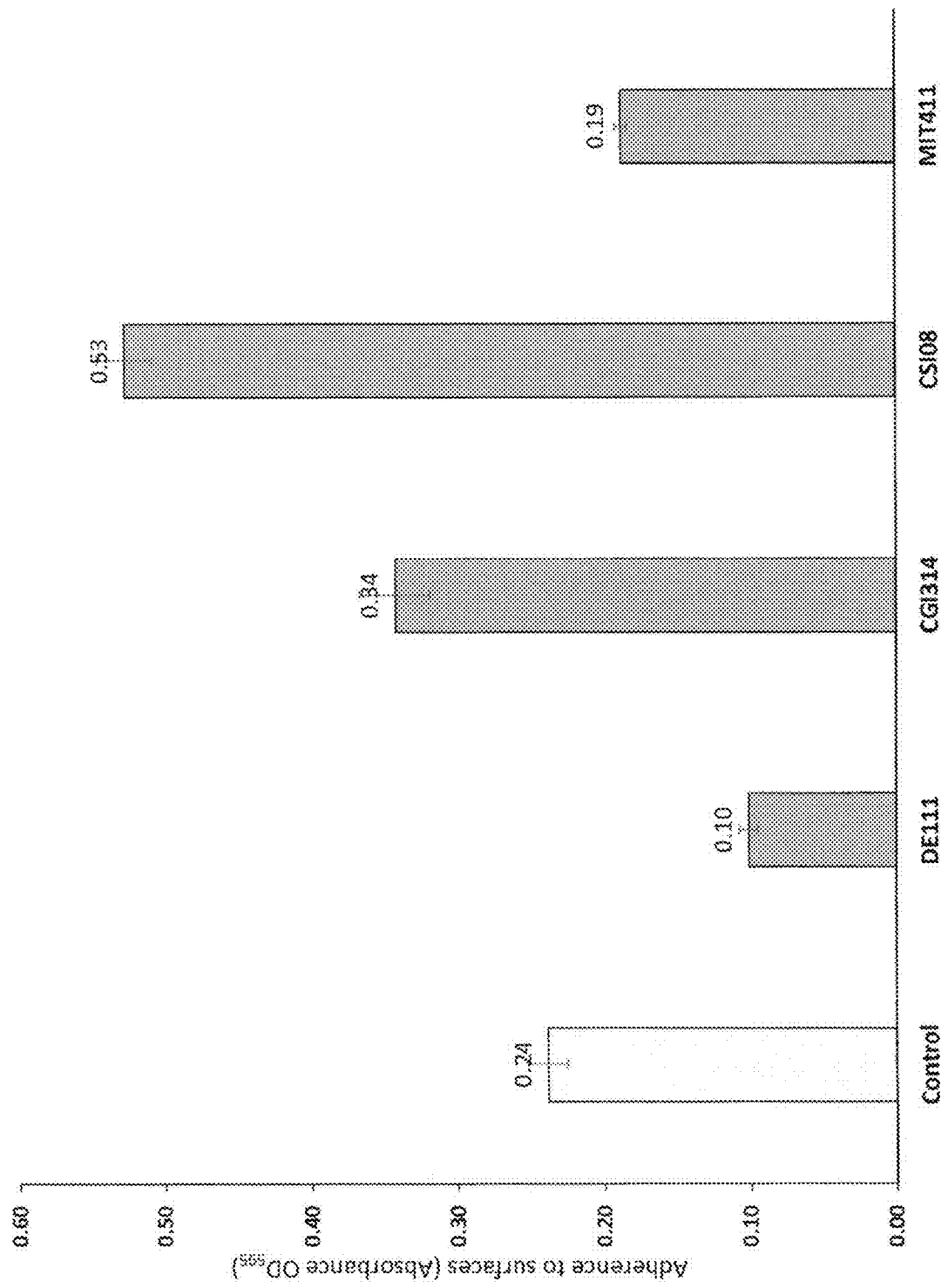
FIG. 16 depicts anti-adherence properties, specifically adherence disruption, of *Bacillus subtilis* DE111, *Bacillus coagulans* CGI314, *Bacillus clausii* CSI08 and *Bacillus megaterium* MIT411 against *P. aeruginosa*. Values represent average adherence n=9±standard error. *P<0.01, P<0.01. Adherance to surfaces was measured as Absorbance $OD_{595}$.

As shown in FIG. 16, DE111 and MIT411 disrupted already formed *P. aeruginosa* biofilms. Conversely, CGI314 and CSI08 did not have any effect in this case.

4. *Bacillus* Spores Anti-Adherence Activity Against *Staphylococcus aureus*

The *Staphylococcus aureus* strain available did not form biofilms under any of the tested conditions. Therefore, tests against this pathogen were not conducted.

In conclusion, *B. subtilis* DE111 has antimicrobial properties against biofilms formed by *Salmonella* and *P. aeruginosa*. In the latter, DE111 was only effective against already adhered *P. aeruginosa*.

*B. coagulans* CGI314 has antimicrobial properties against biofilms formed by *E. coli, Salmonella* and *P. aeruginosa*. CGI314 was only able to prevent the adherence of *P. aeruginosa* but not disrupt established biofilms.

*Bacillus clausii* CSI08 was effective at controlling the adherence of *E. coli, Salmonella* and *P. aeruginosa*. Despite its activity, CSI08 was only able to prevent the formation of *P. aeruginosa* biofilms but not disrupt them.

*Bacillus megaterium* MIT411 was active against biofilms formed by the three pathogens tested. The strain displayed prevention properties against and *Salmonella*, and disruption effectiveness against *P. aeruginosa* established biofilms.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All methods described herein can be performed with the steps performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entireties. The present invention may be embodied in other specific forms without departing from the spirit or essential attributes thereof, and, according, reference should be made to the appended claims, rather than tot the foregoing specification, as indicating the scope of the invention.

We claim:

1. A method of inhibiting growth or activity of bacteria on skin or a mucous membrane in a mammal, comprising the steps of:
    (a) providing a composition comprising Accession no. NRRL B-67989, which is an isolated strain of *Bacillus subtilis* subspecies *inaquosorum* that repels, reduces, inhibits and/or removes a bacterial pathogen; and
    (b) administering the composition to the skin or mucous membrane of the mammal in an amount effective to remove, reduce and/or treat a bacterial infection.

2. The method of claim 1, wherein the pathogen is selected from the group consisting of *E. coli, S. enteritidis, S. aureus, P. aeruginosa*, and *C. acnes*.

* * * * *